United States Patent
Costa et al.

(10) Patent No.: US 10,632,072 B2
(45) Date of Patent: Apr. 28, 2020

(54) SYSTEMS AND METHODS FOR CONTINUOUS MANUFACTURING OF LIPOSOMAL DRUG FORMULATIONS

(71) Applicant: UNIVERSITY OF CONNECTICUT, Farmington, CT (US)

(72) Inventors: Antonio Costa, Farmington, CT (US); Diane J. Burgess, Farmington, CT (US)

(73) Assignee: University of Connecticut, Farmington, CT (US)

( * ) Notice: Subject to any disclaimer, the term of this patent is extended or adjusted under 35 U.S.C. 154(b) by 141 days.

(21) Appl. No.: 15/557,575

(22) PCT Filed: Mar. 18, 2016

(86) PCT No.: PCT/US2016/023156
§ 371 (c)(1),
(2) Date: Sep. 13, 2017

(87) PCT Pub. No.: WO2016/149625
PCT Pub. Date: Sep. 22, 2016

(65) Prior Publication Data
US 2019/0029959 A1    Jan. 31, 2019

Related U.S. Application Data

(60) Provisional application No. 62/135,237, filed on Mar. 19, 2015.

(51) Int. Cl.
*A61K 9/127* (2006.01)
*B01F 5/04* (2006.01)
(Continued)

(52) U.S. Cl.
CPC .......... *A61K 9/1277* (2013.01); *B01F 3/0807* (2013.01); *B01F 5/045* (2013.01);
(Continued)

(58) Field of Classification Search
CPC ..................................................... A61K 9/127
See application file for complete search history.

(56) References Cited

U.S. PATENT DOCUMENTS 4,532,130 A * 7/1985 Djordjevich ......... A61K 9/1277
424/450
4,752,425 A 6/1988 Martin et al.
(Continued)

FOREIGN PATENT DOCUMENTS

CN       101267805 A       7/2006
CN       102307557 A       12/2008
WO    WO-2013059922 A1 *  5/2013  ........... A61K 9/1075

OTHER PUBLICATIONS

The International Search Report (ISR) for PCT/US2016/023156 dated Jun. 21, 2016, pp. 1-4.
(Continued)

*Primary Examiner* — Matthew D Krcha
(74) *Attorney, Agent, or Firm* — McDonnell Boehnen Hulbert & Berghoff LLP

(57) ABSTRACT

The present disclosure provides systems and methods for the continuous production of liposomes. An example method includes (a) mixing a solution of lipid and organic solvent from one or more containers to create an organic solvent-lipid solution, (b) providing the organic solvent-lipid solution to a first inlet of an injection port at a first flow rate, wherein the first inlet is in fluid communication with a first conduit, (c) providing an aqueous solution to a second inlet of the injection port at a second flow rate, wherein the second inlet is in fluid communication with a second conduit, wherein the first conduit is positioned concentrically within the second conduit at an outlet of the injection port, and wherein the first conduit extends through the outlet of the
(Continued)

injection port, and (d) mixing the organic lipid solution and the aqueous solution to create a plurality of liposomes.

19 Claims, 43 Drawing Sheets

(51) Int. Cl.
  *B01J 13/04* (2006.01)
  *B01F 3/08* (2006.01)
  *B01F 15/00* (2006.01)
(52) U.S. Cl.
  CPC ......... *B01F 15/00149* (2013.01); *B01J 13/04* (2013.01); *B01F 2215/0032* (2013.01)

(56) References Cited

U.S. PATENT DOCUMENTS

| | | | |
|---|---|---|---|
| 4,781,871 A | 11/1988 | West, III et al. | |
| 4,885,084 A * | 12/1989 | Doyle | B01F 3/0446 210/132 |
| 5,013,497 A | 5/1991 | Yioumas et al. | |
| 5,077,057 A | 12/1991 | Szoka, Jr. | |
| 5,277,914 A | 1/1994 | Szoka, Jr. | |
| 5,316,771 A | 5/1994 | Barenholz et al. | |
| 5,413,804 A * | 5/1995 | Rhodes | A23C 19/063 426/583 |
| 5,549,910 A | 8/1996 | Szoka, Jr. | |
| 5,567,434 A | 10/1996 | Szoka et al. | |
| 5,653,996 A | 8/1997 | Hsu | |
| 6,120,795 A | 9/2000 | Klimchak et al. | |
| 6,534,018 B1 * | 3/2003 | Baker | A61K 9/1277 264/4.3 |
| 6,855,296 B1 | 2/2005 | Baker et al. | |
| 8,329,070 B2 | 12/2012 | MacLachlan et al. | |
| 8,715,591 B2 | 5/2014 | Gaitan et al. | |
| 2003/0180950 A1 * | 9/2003 | Smyth Templeton | A61K 9/1271 435/458 |
| 2004/0032037 A1 * | 2/2004 | Katinger | A61K 9/1277 264/4.1 |
| 2005/0112184 A1 | 5/2005 | Jahn et al. | |
| 2007/0042031 A1 * | 2/2007 | MacLachlan | A61K 9/127 424/450 |
| 2011/0250264 A1 * | 10/2011 | Schutt | A61K 31/4458 424/450 |
| 2012/0034294 A1 * | 2/2012 | Dupuit | A61K 9/1277 424/450 |
| 2013/0136687 A1 | 5/2013 | Darr et al. | |
| 2013/0168885 A1 * | 7/2013 | Omiatek | A61K 9/1277 264/4.1 |
| 2014/0220111 A1 | 8/2014 | Hayes et al. | |

OTHER PUBLICATIONS

Written Opinion of the International Searching Authority for PCT/US2016/023156 dated Jun. 21, 2016, pp. 1-7.
Balbino TA, Aoki NT, Gasperini AAM, Oliveira CLP, Azzoni AR, Cavalcanti LP, et al. Continuous flow production of cationic liposomes at high lipid concentration in microfluidic devices for gene delivery applications. Chemical Engineering Journal 2013 Jun. 15, 2013;226:423-433.
D'Addio SM, Prud'homme RK. Controlling drug nanoparticle formation by rapid precipitation. Advanced Drug Delivery Reviews 2011 May 30, 2011;63(6):417-426.
Domazou AS, Luigi Luisi P. Size Distribution of Spontaneously Formed Liposomes by the Alcohol Injection Method. J Liposome Res 2002 01/01;12(3):205-220.
Hood RR, DeVoe DL, Atencia J, Vreeland WN, Omiatek DM. A facile route to the synthesis of monodisperse nanoscale liposomes using 3D microfluidic hydrodynamic focusing in a concentric capillary array. Lab Chip 2014;14(14):2403-2409.
Jaafar-Maalej C, Charcosset C, Fessi H. A new method for liposome preparation using a membrane contactor. J Liposome Res 2011 09/01;21(3):213-220.
Jaafar-Maalej C, Diab R, Andrieu V, Elaissari A, Fessi H. Ethanol injection method for hydrophilic and lipophilic drug-loaded liposome preparation. J Liposome Res 2010 09/01;20(3):228-243.
Jahn A, Reiner JE, Vreeland WN, DeVoe DL, Locascio LE, Gaitan M. Preparation of nanoparticles by continuous-flow microfluidics. Journal of Nanoparticle Research 2008 08/01;10(6):925-934.
Jahn A, Stavis SM, Hong JS, Vreeland WN, DeVoe DL, Gaitan M. Microfluidic Mixing and the Formation of Nanoscale Lipid Vesicles. ACS Nano 2010 04/27;4(4):2077-2087.
Jahn A, Vreeland WN, DeVoe DL, Locascio LE, Gaitan M. Microfluidic Directed Formation of Liposomes of Controlled Size. Langmuir 2007 05/01;23(11):6289-6293.
Justo OR, Moraes ÂM. Analysis of process parameters on the characteristics of liposomes prepared by ethanol injection with a view to process scale-up: Effect of temperature and batch volume. Chemical Engineering Research and Design 2011 Jun. 2011;89(6):785-792.
Kastner E, Kaur R, Lowry D, Moghaddam B, Wilkinson A, Perrie Y. High-throughput manufacturing of size-tuned liposomes by a new microfluidics method using enhanced statistical tools for characterization. International Journal of Pharmaceutics 2014 Dec. 30, 2014;477(1):361-368.
Laouini A, Jaafar-Maalej C, Limayem-Blouza I, Sfar S, Charcosset C, Fessi H. Preparation, Characterization and Applications of Liposomes: State of the Art. Journal of Colloid Science and Biotechnology 2012-12-01T00:00:00;1(2):147-168.
Lim J, Swami A, Gilson LM, Chopra S, Choi S, Wu J, et al. Ultra-High Throughput Synthesis of Nanoparticles with Homogeneous Size Distribution Using a Coaxial Turbulent Jet Mixer. ACS Nano 2014 06/24;8(6):6056-6065.
Maitani Y, Igarashi S, Sato M, Hattori Y. Cationic liposome (DC-Chol/DOPE=1:2) and a modified ethanol injection method to prepare liposomes, increased gene expression. International Journal of Pharmaceutics 2007 Sep. 5, 2007;342(1):33-39.
Maitani Y, Soeda H, Junping W, Takayama K. Modified Ethanol Injection Method for Liposomes Containing β-Sitosterol β-D-Glucoside. J Liposome Res 2001 01/01;11(1):115-125.
Peschka R, Purmann T, Schubert R. Cross-flow filtration—an improved detergent removal technique for the preparation of liposomes. International Journal of Pharmaceutics 1998 Mar. 20, 1998;162(1):177-183.
Phapal SM, Sunthar P. Influence of micro-mixing on the size of liposomes self-assembled from miscible liquid phases. Chemistry and Physics of Lipids 2013 Jul.-Aug. 2013;172-173:20-30.
Pons M, Foradada M, Estelrich J. Liposomes obtained by the ethanol injection method. International Journal of Pharmaceutics 1993 Jun. 30, 1993;95(1):51-56.
Schubert MA, Muller-Goymann CC. Solvent injection as a new approach for manufacturing lipid nanoparticles—evaluation of the method and process parameters. European Journal of Pharmaceutics and Biopharmaceutics 2003 Jan. 2003;55(1):125-131.
Stano P, Bufali S, Pisano C, Bucci F, Barbarino M, Santaniello M, et al. Novel Camptothecin Analogue (Gimatecan)—Containing Liposomes Prepared by the Ethanol Injection Method. J Liposome Res 2004 01/01;4(1-2):87-109.
Wagner A, Vorauer-Uhl K, Kreismayr G, Katinger H. Enhanced Protein Loading Into Liposomes by the Multiple Crossflow Injection Technique. J Liposome Res 2002 01/01;12(3)271-283.
Zook JM, Vreeland WN. Effects of temperature, acyl chain length, and flow-rate ratio on liposome formation and size in a microfluidic hydrodynamic focusing device. Soft Matter 2010;6(6):1352-1360.
Zhdanov, et al., "Mixing of confined coaxial flows," International Journal of Heat Transfer, 49(2006):3942-3956.
Balarac, et al., "mixing and coherent vortices in turbulent coaxial jets," C.R. Mecanique 333 (2005) 622-627.
Mortensen, et al., "Mixing of a jet in a pipe," Chemical Engineering Research and Design, Mar. 2004, 82(A3): 357-363.

(56) References Cited

OTHER PUBLICATIONS

Koynova, et al., "Recent Progress in Liposome Production, Relevance to Drug Delivery and Nanomedicine," Recent Patents on Nanotechnology—Aug. 2015, 9, 000-000.

* cited by examiner

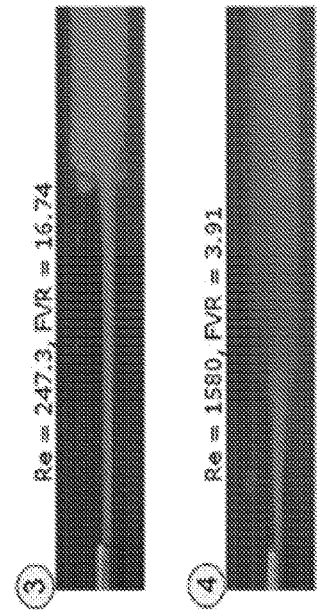
FIG. 16C
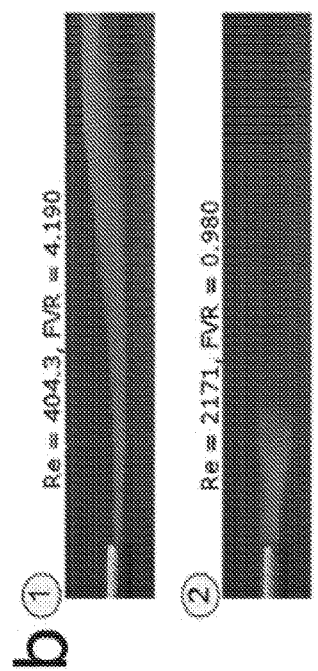
FIG. 16B
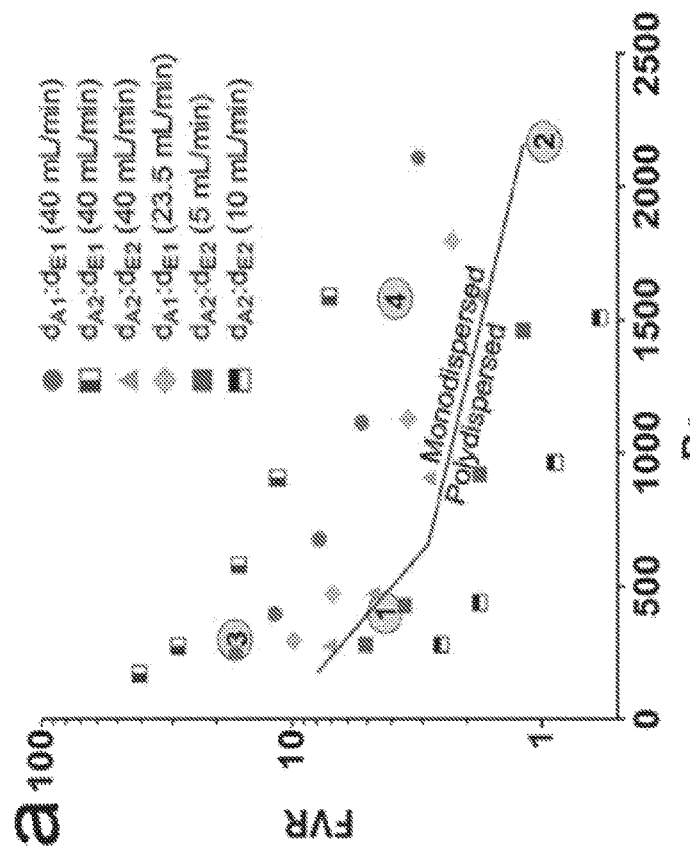
FIG. 16A
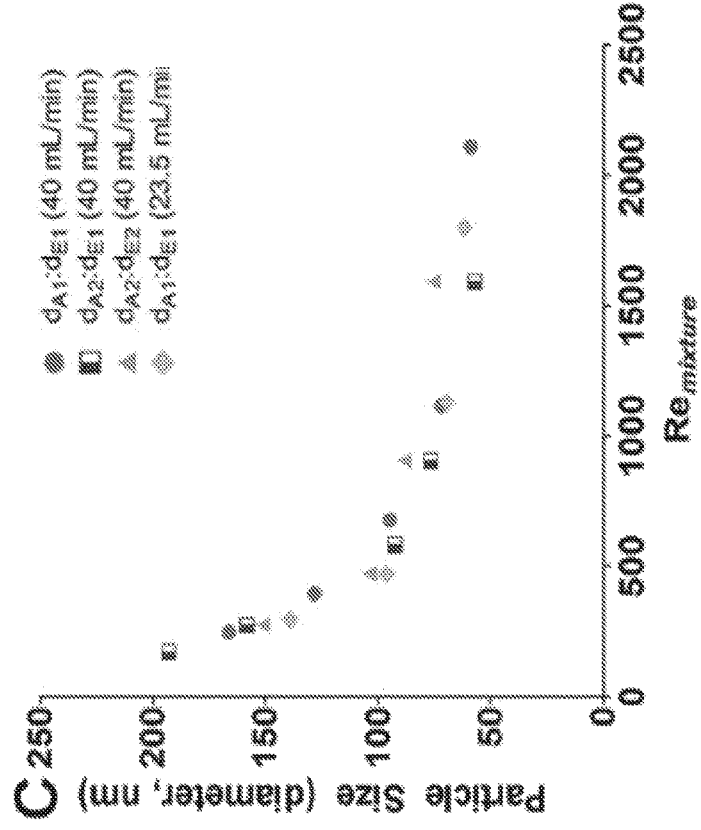

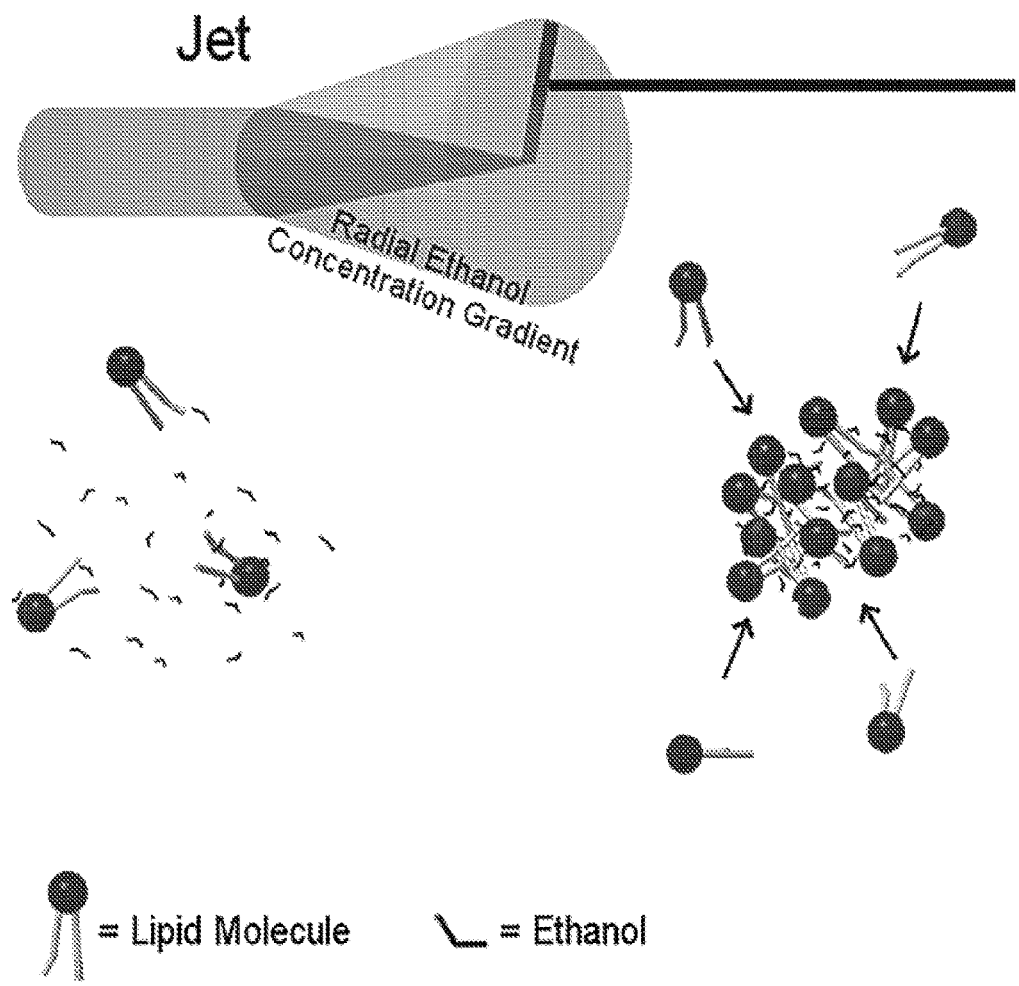
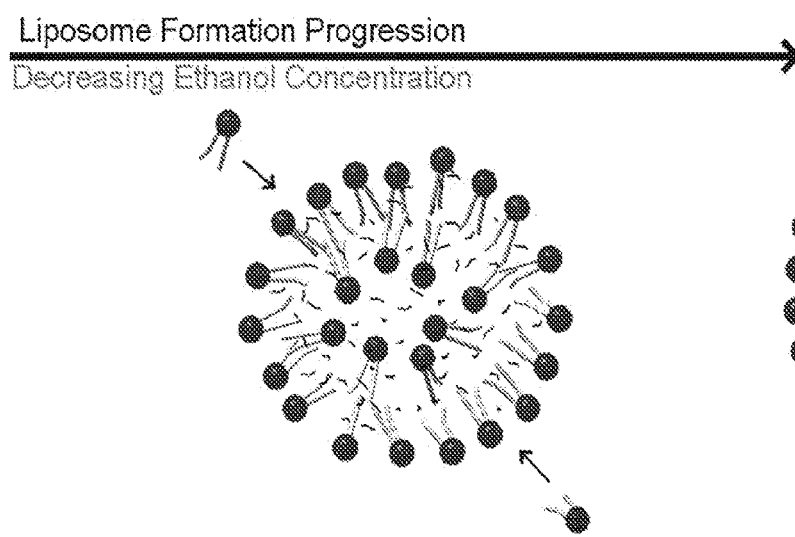
FIG. 24

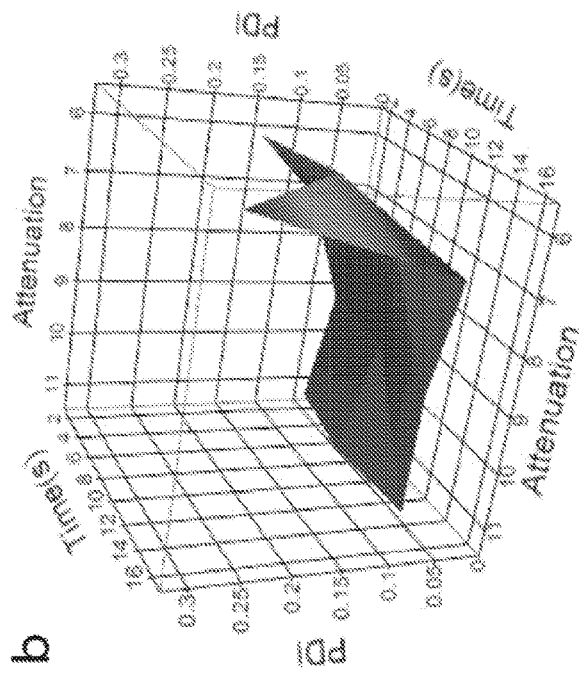
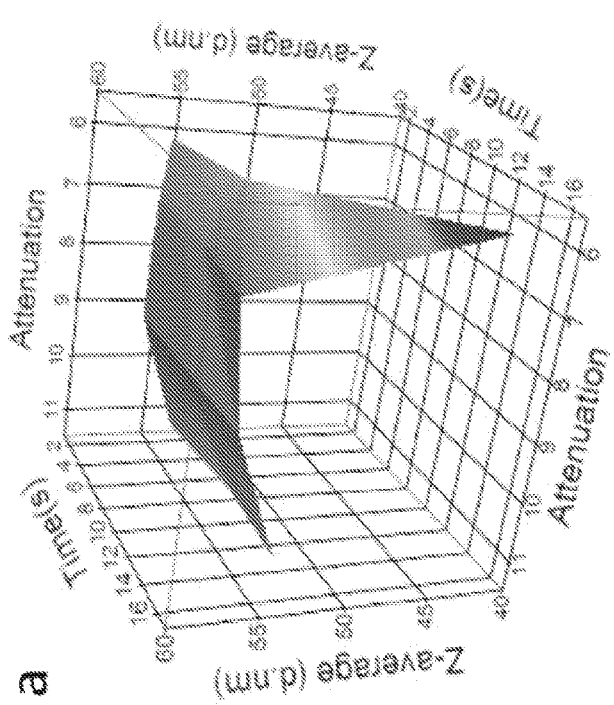
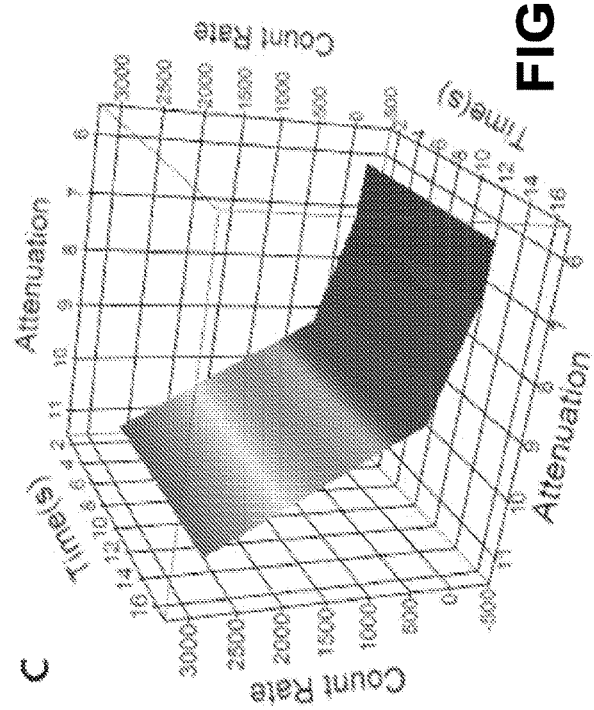
FIG. 28A
FIG. 28B
FIG. 28C

| Term | Estimate | Std Error | t Ratio | | Prob>|t| |
|---|---|---|---|---|---|
| AFR*AFR | 43.5 | 4.22 | 10.3 | | <.0001* |
| Aqueous Phase Flow Rate (AFR) | -45.6 | 9.16 | -4.98 | | 0.0001* |
| Lipid-Concentration | 8.31 | 2.09 | 3.98 | | 0.0011* |
| AFR*AFR*AFR | -24.2 | 10.2 | -2.37 | | 0.0308* |
| Lipid-Concentration*AFR | -2.60 | 2.55 | -1.02 | | 0.323 |

FIG. 42

| Processing Variable | DLS Measurement Variables |
|---|---|
| Total Dead Volume | Measurement Duration |
| Process Stream to Flow Cell Velocity Ratio | Attenuation Factor |
| Laminar Flow Rates[a] | Sample Temperature |
| | Air Bubble Presence | a = applicable only for constant flow approach

FIG. 43

| Spray Voltage | 4000 |
|---|---|
| Sheath Gas Pressure | 20 |
| Ion Sweep Gas Pressure | 8 |
| Aux. Gas Pressure | 5 |
| Capillary Temperature | 350 |
| Tube Lense Offset | 131 |
| Skimmer Offset | 0 |

FIG. 44

| Term | Estimate | Std Error | t Ratio | Prob>|t| |
|---|---|---|---|---|
| Particle Size (d.nm) | -49.1 | 11.2 | -4.4 | 0.0011* |
| Particle Size (d.nm)*ppm | -46.9 | 11.9 | -3.9 | 0.0023* |
| ppm | 10.7 | 6.0 | 1.8 | 0.1046 |

FIG. 45

| Term | Estimate | Std Error | t Ratio | Prob>|t| |
|---|---|---|---|---|
| Particle Size (d.nm)*ppm | -97.0 | 9.6 | -10.2 | <.0001* |
| ppm | -66.0 | 7.9 | -8.4 | <.0001* |
| Particle Size (d.nm)*Particle Size (d.nm) | 29.9 | 4.6 | 6.6 | <.0001* |
| Particle Size (d.nm) | -58.7 | 9.4 | -6.3 | <.0001* |
| Particle Size (d.nm)*(PDI-0.102) | 86.0 | 14.6 | 5.9 | <.0001* |
| CU | 53.5 | 12.0 | 4.5 | 0.0002* |
| PDI | 76.0 | 26.5 | 2.9 | 0.0087* |
| CU*(PDI-0.102)*(PDI-0.102) | 1285.5 | 673.8 | 1.9 | 0.069 |
| (PDI-0.102)*(PDI-0.102) | 1071.4 | 608.5 | 1.8 | 0.0916 |
| ppm*CU | 11.6 | 9.1 | 1.3 | 0.2141 |
| CU*(PDI-0.102) | 22.0 | 29.5 | 0.8 | 0.4638 |

FIG. 46

| Measured Value | Model Factors | | | | Model 1 Prediction | | Model 2 Prediction | |
|---|---|---|---|---|---|---|---|---|
| Total [Lipid] mM | ppm | CU | Particle Size (d.nm) | PDI | Total [Lipid] mM | %Error | Total [Lipid] mM | %Error |
| 1.80 | 16.5 | 0.206 | 167 | 0.05 | 1.81 | 0.3% | 1.78 | 0.9% |
| 2.62 | 24.6 | 0.294 | 167 | 0.05 | 2.77 | 5.5% | 2.56 | 2.3% |
| 2.78 | 27.6 | 0.333 | 167 | 0.05 | 3.12 | 12.5% | 3.00 | 8.2% |
| 7.07 | 67.8 | 0.789 | 167 | 0.05 | 7.89 | 11.7% | 7.88 | 11.4% |
| | | | | | Average | 7.5% | Average | 5.7% |
| | | | | | StDEV | 5.7% | StDEV | 4.9% |

FIG. 47

SYSTEMS AND METHODS FOR CONTINUOUS MANUFACTURING OF LIPOSOMAL DRUG FORMULATIONS

CROSS-REFERENCE TO RELATED APPLICATIONS

This application is a U.S. national phase of International Application No. PCT/US2016/023156, filed on Mar. 18, 2016, which claims priority to U.S. Provisional Application No. 62/135,237, filed Mar. 19, 2015, both of which are incorporated by reference herein in their entirety.

GOVERNMENT RIGHTS

This invention was made with government support under contract number HHSF223201310117C awarded by the United States Food and Drug Administration. The government has certain rights in the invention.

BACKGROUND

Liposomes as parenteral drug delivery carriers are currently being utilized in the pharmaceutical industry. There are several FDA-approved liposomal injectable products on the market with many more potential products in clinical trials and in preliminary studies. Liposomes have proven to be useful in cancer, macular degeneration, fungal infections, and vaccines with approved products such as Doxil®, Visudyne QLT®, Ambisome®, and Epaxal®, respectively. Moreover, liposomes as non-viral gene-delivery vectors are being investigated in clinical trials.

To date, there are various types of liposomes that are adapted for different applications such as cancer, gene-delivery, siRNA-delivery, protein/peptide delivery and small molecule delivery. Depending on the application, there will be differences in the liposome formulations such as in lipid type/composition, size and other properties as discussed above. For example, Stealth® liposomes composed of DSPC/Chol/PEG-DSPE are widely used in cancer and cell-targeting applications as a stable liposome formulation due to their prolonged half-life compared to conventional liposomes. For siRNA applications, different fusogenic lipids such as DOPE are used to form complexes with siRNA for efficient delivery.

The properties of liposomes such as the hydrodynamic radius (size), zeta-potential, lipid-packing, encapsulation efficiency, and external modifications (such as polymer coatings) are important in formulating an efficacious drug delivery system. When considering in vivo applications of liposomes, the correct size of liposomes is one property that is vital in order to deliver the liposomes to different locations in the body. For example, liposomes with an approximate diameter of <100 nm are known to accumulate at cancer sites as a result of the enhanced permeability retention (EPR) effect, whereas very small liposomes or larger liposomes are filtered or taken up elsewhere in the body, respectively.

Some liposome properties are highly dependent on the processing conditions of the formulation, and any alterations in these processing conditions will lead to differences in the final formulation. Therefore, it is important to develop a manufacturing system that can accurately and predictively produce liposomes based on the user's requirements.

SUMMARY OF THE INVENTION

In one aspect, the present disclosure provides a system for the continuous production of liposomes, the system comprising (a) a mixer in fluid communication with one or more containers, (b) a vessel, and (c) one or more injection ports, wherein each injection port includes a first inlet including a first conduit in fluid communication with the mixer, a second inlet including a second conduit in fluid communication with the vessel, and an outlet, wherein the first conduit is positioned concentrically within the second conduit, and wherein the first conduit extends through the outlet.

In another aspect, the present disclosure provides a method for the continuous production of liposomes. The method may include (a) mixing a solution of lipid and organic solvent from one or more containers to create an organic solvent-lipid solution, (b) providing the organic solvent-lipid solution to a first inlet of an injection port at a first flow rate, wherein the first inlet is in fluid communication with a first conduit, (c) providing an aqueous solution to a second inlet of the injection port at a second flow rate, wherein the second inlet is in fluid communication with a second conduit, wherein the first conduit is positioned concentrically within the second conduit at an outlet of the injection port, and wherein the first conduit extends through the outlet of the injection port, and (d) mixing the organic lipid solution and the aqueous solution to create a plurality of liposomes.

In yet another embodiment, the present disclosure provides a non-transitory computer readable medium having stored thereon instructions, that when executed by one or more processors, cause a system for the continuous production of liposomes to perform the operations of the just described method.

The system and methods disclosed herein significantly reduces waste of materials and decreases processing/production times. In addition, the continuous manufacturing method described herein avoids variation due to changes in processing conditions and human intervention during the transfer of materials since the liposomes will be formulated in a closed-environment with reduced human intervention. In addition, a continuous manufacturing process is scalable to larger production sizes. In the system described herein, the only dimension that would need to be increased would be time since the equipment used in the manufacturing during the clinical trials and the end-stage production would be the same. This approach would reduce the regulatory burden on the manufacturer, reduce manufacturing costs/time associated with additional validation testing, and result in faster delivery of the drug product to those desperately in need.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 16A is a graphical representation of flow velocity ratio (FVR) vs. the mixture Reynolds Number ($Re_{mixture}$), according to an example embodiment.

FIG. 16B is a plurality of flow images corresponding to locations (1, 2, 3, and 4) from FIG. 16a demonstrating flow profiles leading to monodispersed or polydispersed systems, according to an example embodiment.

FIG. 16C is a graphical representation of Z-average particle size vs. $Re_{mixture}$ for only monodispersed liposomes. $d_{A1}$=3.175 mm, $d_{A2}$=4.572 mm, $d_{E1}$=0.508 mm, $d_{E2}$=1.016 mm, according to an example embodiment.

FIG. 24 is a model for liposome formation from a coaxial turbulent jet mixer in co-flow, according to an example embodiment.

FIGS. 28A-C are a comparison of manual DLS measurement settings on the liposome particle size (z-average), the PDI and the DLS count rate (kcps), according to example embodiments.

FIG. 42 illustrates a table showing DOE on lipid concentration vs. particle size—model parameter estimates sorted by statistical significance.

FIG. 43 illustrates a table showing variables that influence continuous particle size measurements.

FIG. 44 illustrates a table showing TSQ HPLC-MS ESI operating conditions used in the analysis of lipid concentration quantitation.

FIG. 45 illustrates a table showing sorted parameter estimates and model terms for Model 1.

FIG. 46 illustrates a table showing sorted parameter estimates and model terms for Model 2.

FIG. 47 illustrates a table showing validation data points for both lipid concentration ([Lipid]) models.

DETAILED DESCRIPTION

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the Figures, can be arranged, substituted, combined, separated, and designed in a wide variety of different configurations, all of which are explicitly contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, with respect to measurements, "about" means +/−5%.

Figure 1:
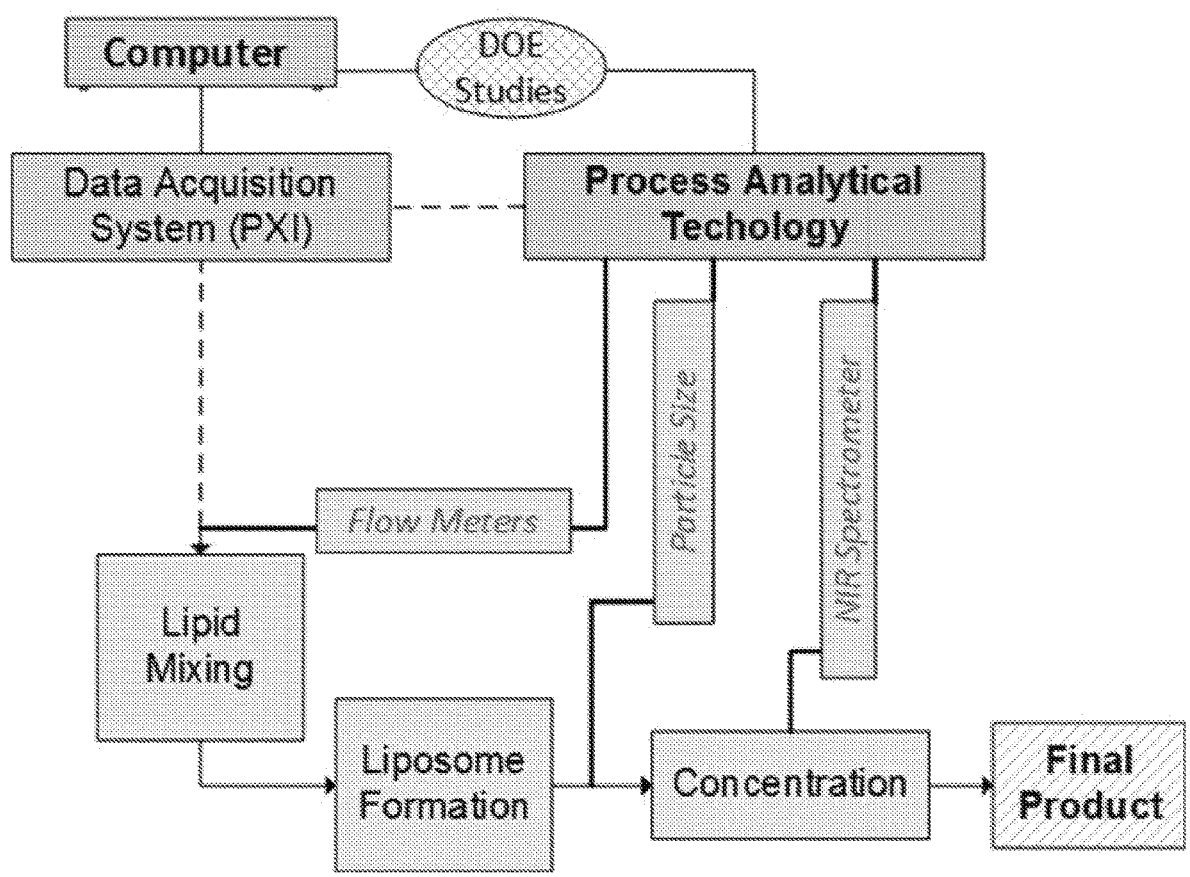
FIG. 1 is a schematic representation of a system for the continuous manufacturing process for liposomal drug formulations, according to an example embodiment.

With reference to the Figures, FIG. 1 illustrates an example overview of a continuous manufacturing process for liposomal drug formulations. The computer/data acquisition system controls/acquires all signals from the process. The continuous manufacturing design may include process analytical technology (PAT) to increase quality assurance and consistency during operation. PAT will analyze parameters such as particle size, zeta potential, and encapsulated drug for quality control purposes in real-time. These formulation parameters will be feed back into the system such that the overall process is constantly controlled and monitored, leading to ultimately a high quality formulation with increased throughput.

A PAT tool may be any tool that fits under the following categories: (1) acquire/analyze data (multivariate capable); (2) processing analyzer; (3) process control tool; and (4) management tool that allow for continuous improvement and knowledge of a process. Multivariate tools may be statistical designs of experiments (DOE). Combining these DOE studies with some type of computer software (as a process control tool) to control and alter processing conditions would fit under this category. In this case, a predictive equation or results from a DOE study may then be used to adjust the final formulation when process variations are encountered. Process analyzing tools can be implemented in three ways: (1) at-line, or where a sample is removed and isolated from a system; (2) on-line, or where a sample is diverted, measured and returned to the process; or (3) in-line, or where a sample is measured directly in the process. Process analyzers generate large amounts of data that can be collected and stored for quality control purposes and reporting. Lastly, analysis of data to build on the understanding of the overall process will aid in a continuous learning and improvement of the processing stream, which will facilitate regulatory acceptance and provide evidence to support alterations to an existing process.

An example of a possible at-line or on-line measurement is using the Malvern Zetasizer with a flow-cell attachment. A solenoid valve may be configured to open and direct the flow of the sample to the Zetasizer flow cell and closes once enough sample is loaded in the cell. The Zetasizer then performs a measurement and this information may be sent to a custom-built LabVIEW program. In the LabVIEW program, the measurement value is analyzed and process conditions (e.g. flow rates) are altered based on the aforementioned DOE studies to re-adjust the particle size to be within quality control limits, as discussed in additional detail below.

Figure 2:
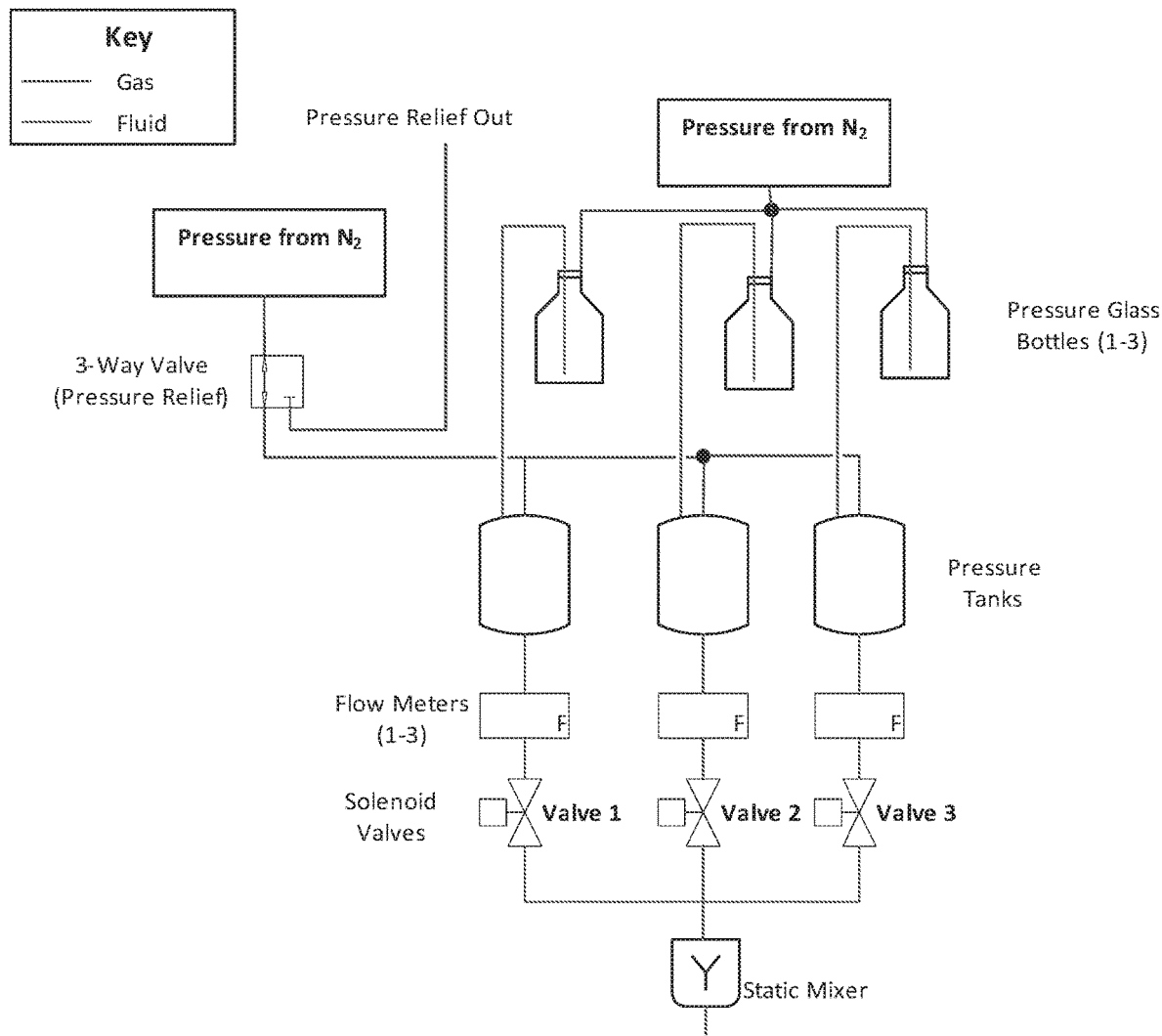
FIG. 2 is a schematic representation of a lipid mixing process, according to an example embodiment.

FIG. 2 illustrates a lipid-mixing stage of the continuous liposome manufacturing process. In one example, as shown in FIG. 2, the mixer is a static mixer that combines solutions from each of the one or more containers. In the particular example shown in FIG. 2, the lipid-mixing stage includes three containers including three different reservoirs of lipid dissolved in ethanol. An ethanol-injection method was chosen to prepare the liposomes. The ethanol-injection method can be developed as a continuous process and the solvent (ethanol) is less toxic than other solvents (e.g. chloroform) used in other preparation methods. Moreover, many lipids are soluble or moderately soluble in ethanol. However, other organic solvents are possible as well.

Since the lipid concentration in each reservoir may be different, the system shown in FIG. 2 describes a way to mix the lipid dissolved in ethanol. Lipid and ethanol may be placed in each of the three glass pressure bottles, although other containers are possible as well. Further, there may be additional or fewer containers than the three glass pressure bottles shown in FIG. 2. A nitrogen gas tank may be connected to each container with a maximum of 20 psi flowing into each of the containers. Other maximum pressures are possible as well. In addition, lipid and ethanol may be transferred from reservoirs via a pump (e.g. a gear pump) instead of using pressurized containers. It is useful to maintain a constant flow without many disturbances in the fluid flow (e.g. abruptly changing the flow rates on a short time scale).

As shown in FIG. 2, a first set of one or more valves may be positioned between the one or more containers and the one or more pressure tanks. Further, a second set of one or more valves may be positioned in fluid communication with each of the one or more containers. In addition, one or more flow meters may be positioned between each of the one or more pressure tanks and each of the one or more valves of the second set. In one example, the first set of one or more valves are solenoid valves, and the second set of one or more valves are proportioning valves.

Figure 3:
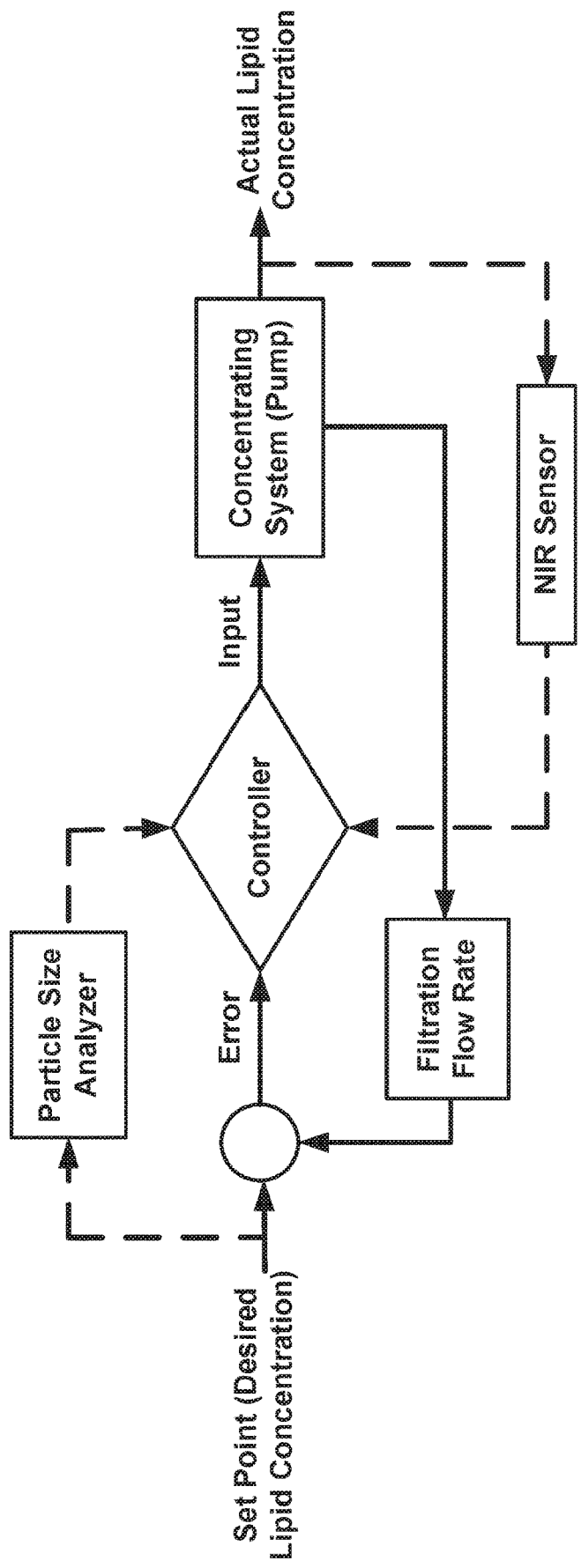
FIG. 3 is a control design for a system for the continuous manufacturing process for liposomal drug formulations, according to an example embodiment.

In the example shown in FIG. 2, the proportioning valves are positioned downstream from the containers. When the solenoid valves open, ethanol flows through one or more flow meters. In another embodiment, the solenoid valves may be replaced by air/pressure actuated valves, or any type of valve that can be controlled via a control system. Each of the one or more flow meters detects the flow rate of the ethanol and sends feedback to a controller. The feedback may be controlled via a proportional-integral-derivative (PID) controller. FIG. 3 is an example of a control loop using both feedback and feedforward control.

As shown in FIG. 3, the feedback control may consist of a pump that adjusts to maintain a set flow rate and may be used to increase or maintain a lipid concentration. A particle size analyzer and near-infrared (NIR) sensor may be used as feedforward controls in that measurements from these components may be used as inputs in a predictive model that is used to determine the lipid concentration.

Figure 4:
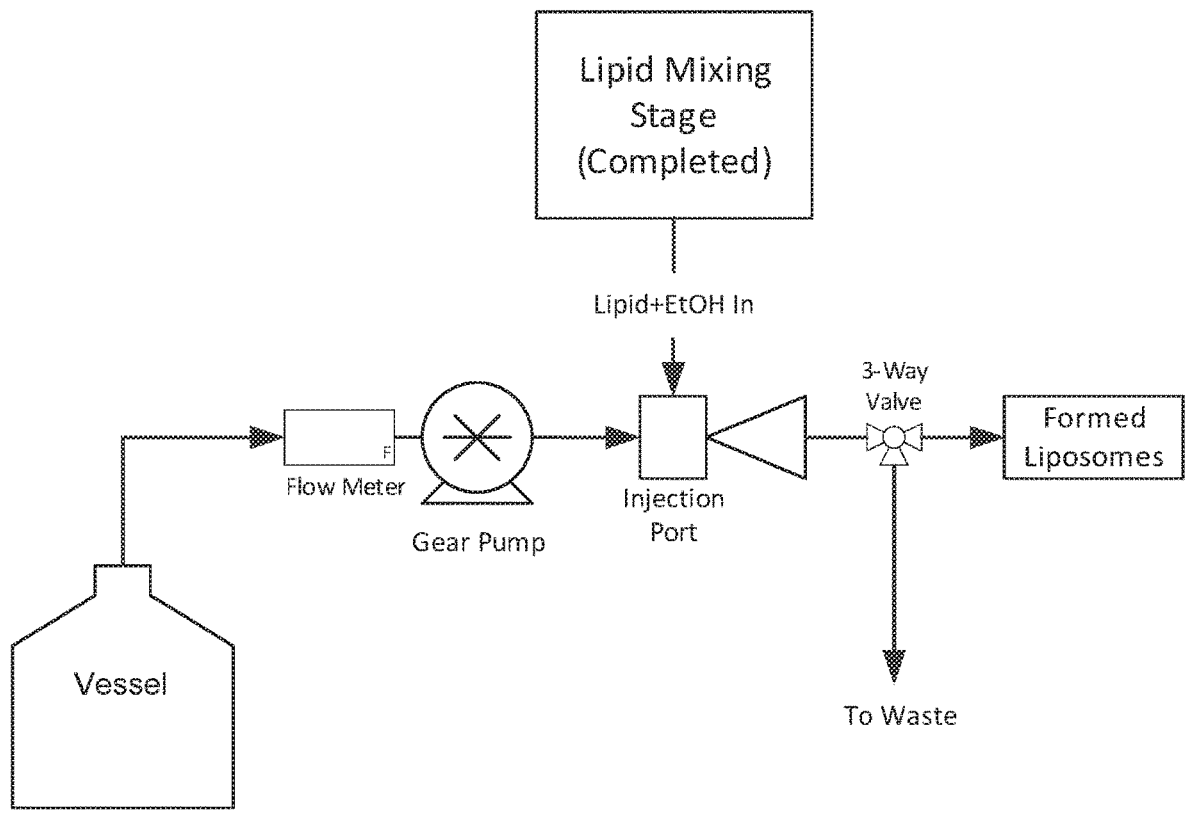
FIG. 4 is a schematic representation of a liposome formation stage, according to an example embodiment.

FIG. 4 illustrates the liposome formation stage of the continuous liposome manufacturing process. The liposome formation stage will consist of an "injection port" that connects the lipid and ethanol liquid stream with an aqueous stream. When both streams come in contact, liposomes will be formed. The diffusion of lipid from the ethanol stream into the aqueous stream causes the lipid to form into bilayers and subsequently liposomes. In order to transfer the aqueous medium from a vessel to the injection port, a gear pump may be incorporated into the design, as shown in FIG. 4. A gear pump may be advantageous since it has a continuous duty cycle, which prevents a pulsed flow. For example, peristaltic pumps have a pulsed flow due to the motor heads compressing the tubing to move the fluid. This pulsing will cause flow rates to change and may result in liposome formation with heterogeneous particle sizes. In one specific example, an I-Drive gear pump may be used to control the flow rate of the aqueous or aqueous-organic mixture phase input. This gear pump is a compact, brushless DC electromagnetic drive and is controlled via a 4-20 mA analog signal. The wetted parts are: 316 SS body, polyphenylene sulfide (PPS), polytetrafluoroethylene (PTFE)—all of which are compatible with water and ethanol. The flow rate range for this gear pump is approximately 20-500 mL/min. Other pumps that maintain a constant flow rate are possible as well.

Figure 5:
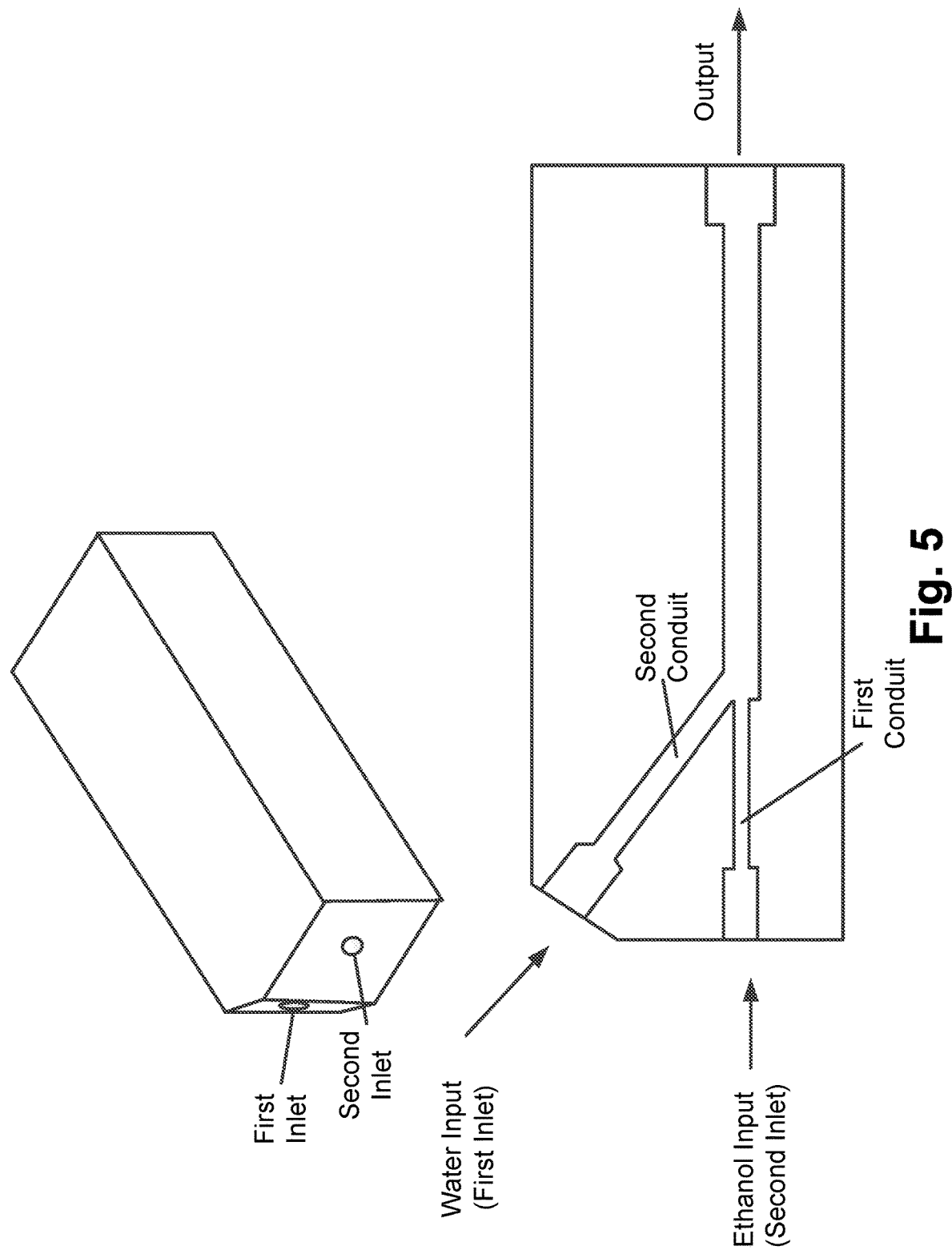
FIG. 5 is a schematic representation of an example injection port, according to an example embodiment.

An example injection port is shown in FIG. 5. Such an injection port allows for rapid mixing of the ethanol and lipid into the aqueous phase. This rapid mixing is the location where the liposomes are formed. The injection port may comprise stainless steel, such as 304 stainless steel or 316 stainless steel. In another example, the injection port may comprise a plastic material, such as PTFE. Other materials are possible as well. As shown in FIG. 5, the injection port includes two inlets, one for lipid and ethanol and one for the aqueous or aqueous-organic mixture phase. The joined output is designed for flow rates greater than about 400 mL/min.

Figure 6:
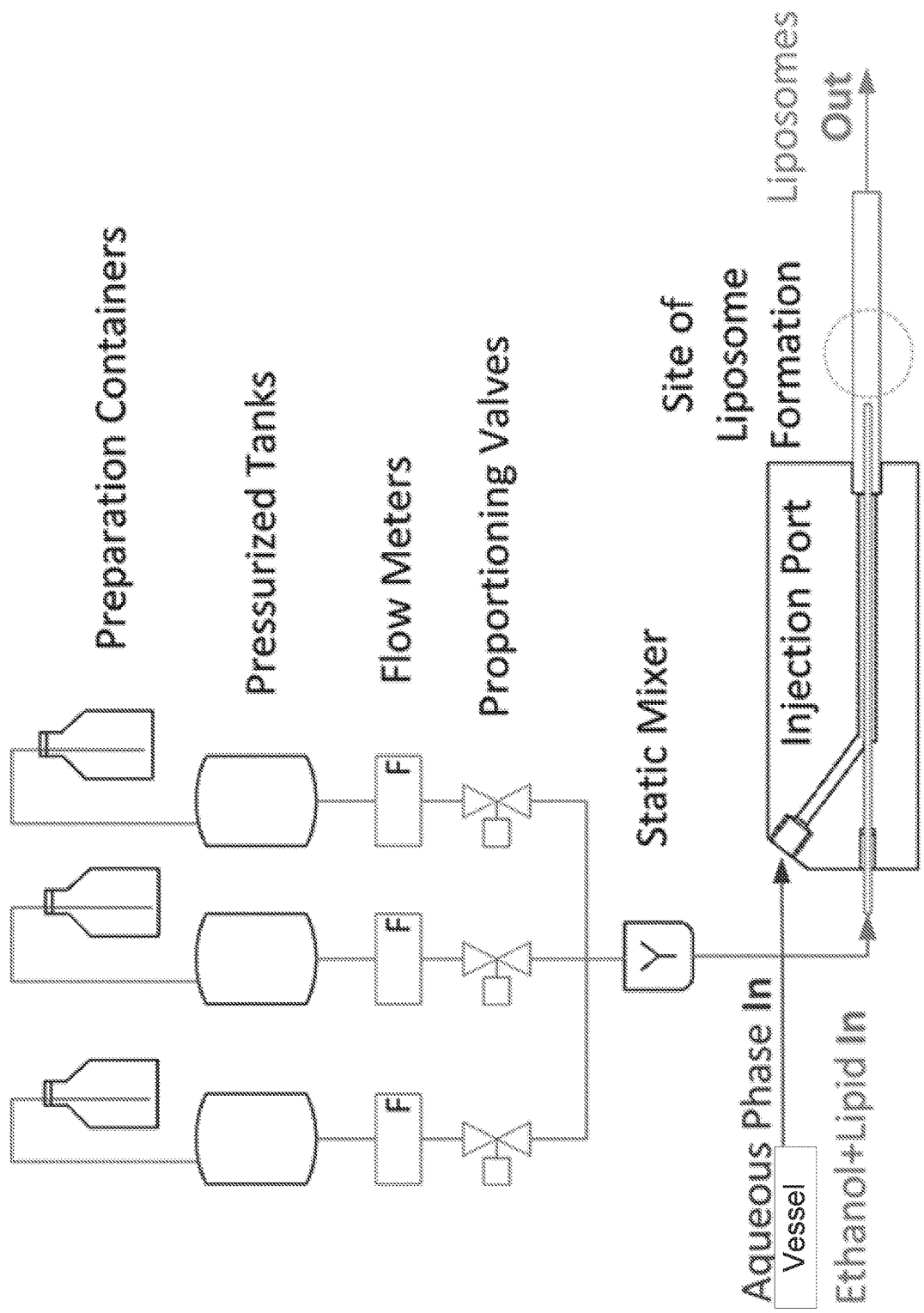
FIG. 6 is a schematic representation of a lipid mixing process and a liposome formation stage including an injection port, according to an example embodiment.

One particular embodiment of the system for continuous production of liposomes is shown in FIG. 6. As shown in FIG. 6, the system may include a mixer in fluid communication with one or more preparation containers. The mixer may be a static mixer configured to combine a solution from each of the one or more preparation containers. The system may further include a vessel. An example vessel may include an aqueous solution, such as water, a low-medium ionic strength water (e.g. 0.9% NaCl in water), an aqueous-organic phase mixture, an aqueous phase buffer, or any type of buffer commonly used in drug products (e.g. phosphate buffer or histidine buffer with sucrose), as examples. The system may further include one or more injection ports, each injection port including a first inlet, a second inlet, and an outlet, as discussed above in relation to FIG. 5. The first inlet may include a first conduit in fluid communication with the mixer, and the second inlet may include a second conduit in fluid communication with the vessel. As shown in FIG. 6, the second conduit may extend through the outlet of the injection port. The first conduit may be positioned concentrically within the second conduit such that the first conduit extends through the outlet of the injection port and terminates within the second conduit. The location of the liposome formation may not be located inside the injection port, but rather approximately the location where the first conduit terminates within the second conduit. In one particular example, the first conduit extends between about 0.5 inches to about 24 inches from the outlet of the injection port, and the second conduit extends between about 0.5 inches to about 24 inches from the outlet although other examples are possible as well. In one example, the plurality of liposomes formed in the system are unilamellar liposomes.

In the particular example shown in FIG. 6, the system further includes one or more pressure tanks connected to the one or more containers. The system may further include one or more valves in fluid communication with the one or more containers, and one or more flow meters positioned between the one or more pressure tanks and the one or more valves. In yet another example, the system may include one or more pulseless pumps (e.g., gear pumps) and a one or more non-pressurized containers to maintain low flow rates. As discussed above, the one or more containers may each include a different concentration of lipid dissolved in ethanol. As such, by adjusting the ratio of a solution comprising a combination of fluid from each of the one or more containers, the system may consequently adjust a lipid concentration of a lipid solution provided to the first inlet of the injection port.

In another embodiment, the first inlet of each of the one or more injection ports includes a third conduit in fluid communication with the mixer, wherein the third conduit is positioned concentrically within the second conduit and adjacent to the first conduit such that the third conduit extends through the outlet.

The system may further include a particle size analyzer configured to determine a size and/or a size distribution (e.g., a mean, mode, or percentage of a size class) of liposomes created within the system. The mean particle size diameter and particle size distribution of liposomes can be analyzed by a variety of instruments and technologies. These technologies include but are not limited to: dynamic light scattering, static light scattering, particle tracking, various forms of electron microscopy and acoustic spectroscopy. In order to accommodate many liposomal formulations, particle sizing technology used to measure liposomes may be capable of measuring particle diameters as low as 25 nm. Moreover, many of these technologies are only applicable to off-line measurements and cannot be implemented into a process (i.e. batch nor continuous). For a continuous process, the measurement may be either at/on/in-line capable. Two technologies that have this capability are dynamic light scattering and acoustic spectroscopy.

Dynamic light scattering is based on light or photon fluctuations that are correlated to the diffusion of particles, which is then related to particle size information. This technique uses two analyses in calculating the particle size data; namely, an intensity-based analysis and an intensity-weighted or cumulants analysis. The intensity analysis is based on the raw data (photon fluctuations). The cumulants analysis is based on an exponential equation and is weighted according to the intensity of the particles. For continuous measurements, this technique can be setup in a process stream by the use of a flow cell. The flow cell enables the sample to enter the cell at one end and leave the cell at the other. A pump may be used to control the flow rate and/or stop the flow into the flow cell. If the flow rate is low enough to sustain laminar flow (around 1-1.5 mL/min), then the sample may constantly flow through the flow cell during measurement. For higher flow rates, turbulence develops and the higher velocities impart motion to the particles, resulting in erroneous particle size measurements. If higher flow rates are required (>1.5 mL/min), the sample can be rapidly loaded into the flow cell followed by stopping the flow prior to the particle sizing measurement.

Acoustic spectroscopy is based on the propagation of sounds waves at multiple frequencies while measuring the attenuation of the ultrasound, which is then used in calculating the particle size distribution. There is a correlation between the displacement of the sound waves at multiple frequencies with the mean particle size and size distribution. The advantage of this technique is that the particle size measurements can be taken at higher flow rates that are not constrained to the laminar flow regime as is the case with dynamic light scattering. A disadvantage of this technique is that air bubbles may interfere with the particle size measurements.

From a quality perspective, it is useful that the mean particle size and size distribution of the liposomal formulation is within specifications. For example, these specifications could be that the mean particle size diameter is 100 nm±10 nm with a particle size distribution of 25 nm. For both batch and continuous processes, the particle size can be measured during or after processing. However, continuous processing has the advantage in that the particle size measurement can be performed continuously as the liposomes are being formed, and this information can be used to: divert out-of-specification liposomes to waste without compromising the entire unit or batch; and to correct the problem that caused the formation of out-of-specification liposomes. In contrast to the continuous process, the particle size measurement for a batch process would take place once all of the liposomes are formed and consequently failure to meet the particle size specifications would result in removal of the entire batch. In the system described herein, the mean liposome particle size diameter and particle size distribution can be quantitatively monitored during continuous processing and this information can be used in a feedback algorithm to maintain these liposomal quality attributes.

The system may also include a controller (e.g., a microprocessor, FPGA, microcontroller, or the like) configured to (i) determine a difference between a desired size and/or desired size distribution of the liposomes and the determined size and/or size distribution as measured by the particle size analyzer, and (ii) adjust one or more parameters of the system in response to the determined difference. In one example, adjusting one or more parameters of the system comprises adjusting a flow rate at which the aqueous solution is supplied from the vessel to the second inlet of the injection port. In particular, if the system detects that the size of the liposomes formed in the second conduit are smaller than the desired size, the controller may be configured to decrease the flow rate at which the aqueous solution is supplied from the vessel to the second inlet of the injection port. In contrast, if the system detects that the size of the liposomes formed in the second conduit are larger than the desired size, the controller may be configured to increase the flow rate at which the aqueous solution is supplied from the vessel to the second inlet of the injection port.

In another example, adjusting one or more parameters of the system comprises adjusting a lipid concentration of the organic lipid solution supplied from the mixer to the first inlet of the injection port. As discussed above, the organic lipid solution may comprise a mixture from one or more containers. Each of the one or more containers may have a different concentration of lipid dissolved in ethanol. As such, by adjusting the ratio of a solution comprising a combination of fluid from each of the one or more containers, the system may consequently adjust a lipid concentration of a lipid solution provided to the first inlet of the injection port. In particular, if the system detects that the size of the liposomes formed in the second tube are smaller than the desired size, the controller may be configured to increase the lipid concentration of the organic lipid solution supplied from the mixer to the first inlet of the injection port. In contrast, if the system detects that the size of the liposomes formed in the second tube are larger than the desired size, the controller may be configured to decrease the lipid concentration of the organic lipid solution supplied from the mixer to the first inlet of the injection port.

In yet another example, adjusting one or more parameters of the system comprises adjusting a viscosity of the aqueous solution supplied from the vessel to the second inlet of the injection port. In particular, if the system detects that the size of the liposomes formed in the second tube are smaller than the desired size, the controller may be configured to increase the viscosity of the aqueous solution supplied from the vessel to the second inlet of the injection port. In one particular example, this may be accomplished by increasing a percentage of ethanol in the aqueous solution. In contrast, if the system detects that the size of the liposomes formed in the second tube are larger than the desired size, the controller may be configured to decrease the viscosity of the aqueous solution supplied from the vessel to the second inlet of the injection port. In one particular example, this may be accomplished by decreasing a percentage of ethanol in the aqueous solution. Other parameters of the system may be adjusted as well.

Figure 7:
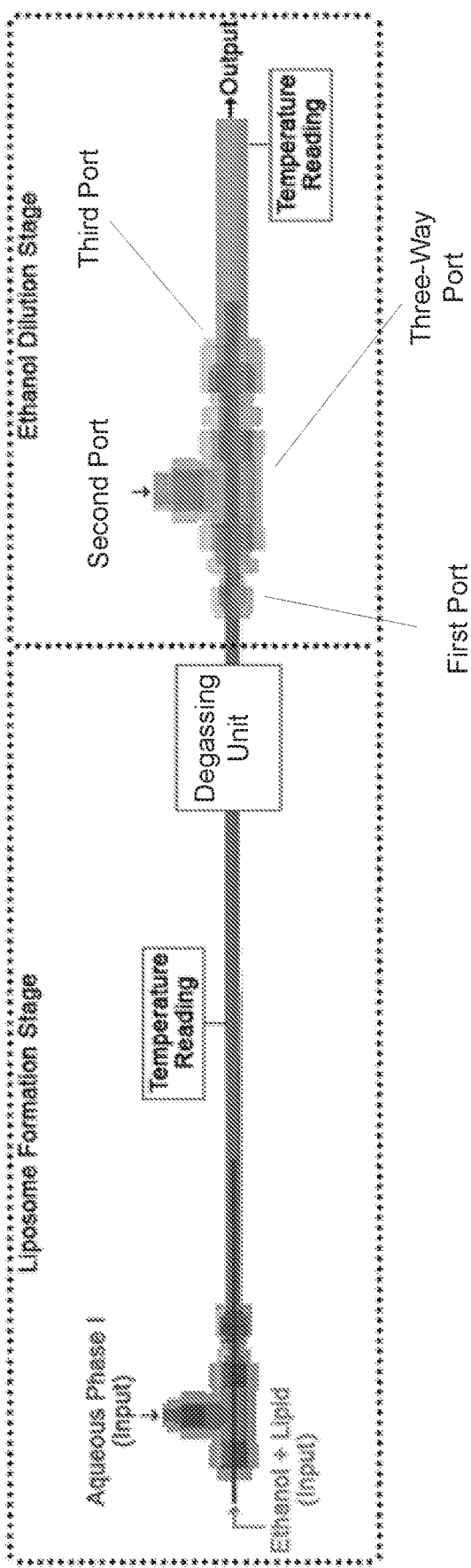
FIG. 7 is a schematic representation of the liposome formation stage followed by an ethanol dilution stage, according to an example embodiment.

FIG. 7 illustrates a schematic representation of the liposome formation stage followed by an ethanol dilution stage, according to an example embodiment. As shown in FIG. 7, after the liposomes are formed in the second conduit of the injection port, the liposomes may be passed through one or more degassing units. Next, the liposomes may be passed through a three-way port including a first port, a second port, and third port. As shown in FIG. 7, the first port may be in fluid communication with the one or more degassing units, the second port may be in fluid communication with the vessel, and the third port may be an outlet port. In one example, the ethanol dilution stage of the system may further include a gear pump positioned between the vessel and the three-way port.

Figure 8:
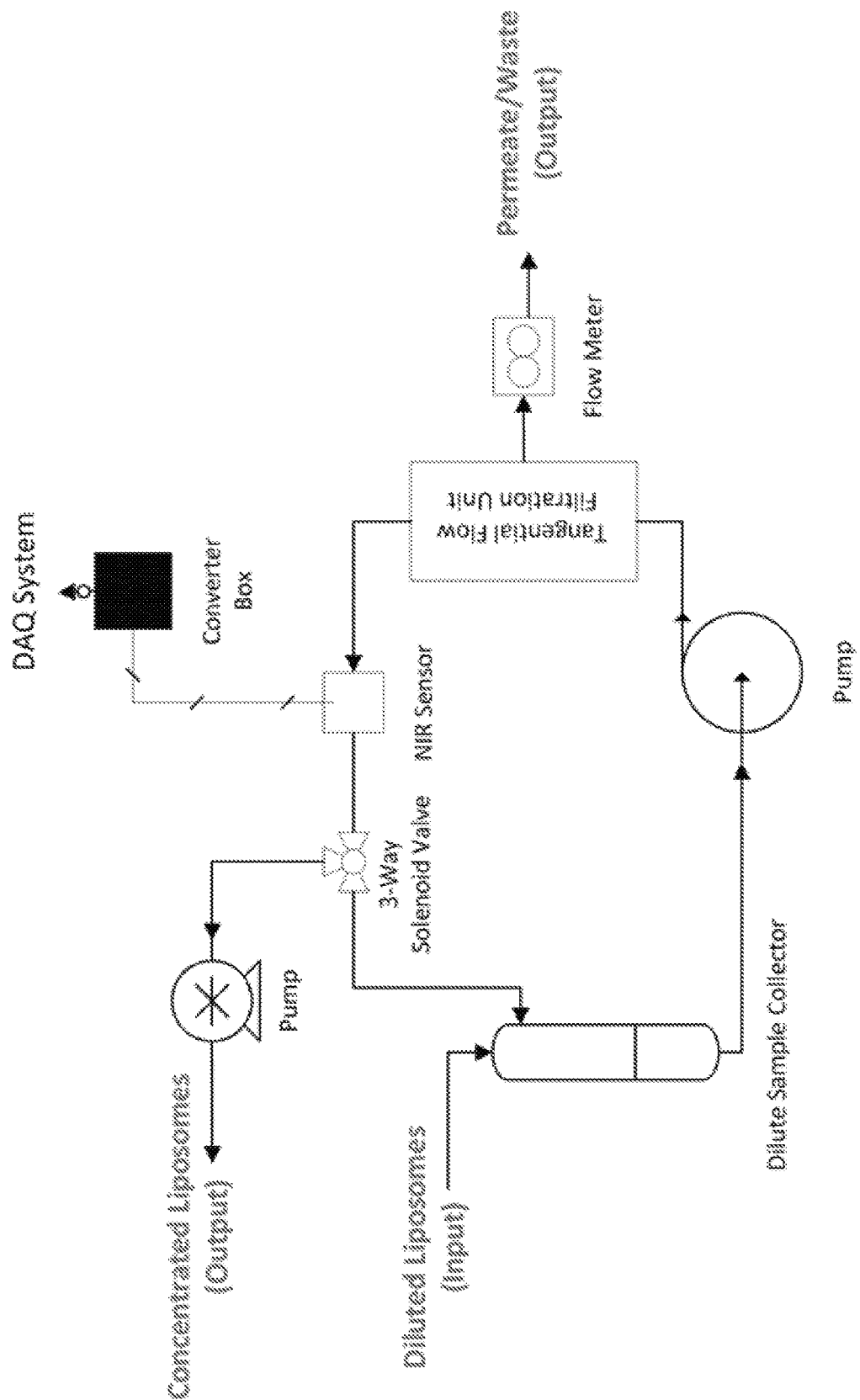
FIG. 8 is a schematic representation of a lipid concentration stage, according to an example embodiment.

FIG. 8 illustrates a concentration stage of the continuous liposome manufacturing process, according to an example embodiment. The total lipid concentration is a quality attribute for liposomal drug products. The total lipid concentration may refer to the amount of phospholipid and/or other lipid molecules such as cholesterol that form the liposomal bilayer. The lipid concentration can be used to estimate the amount of liposomal vesicles, which may further be related to either drug encapsulation, i.e. drug molecules in the aqueous compartment of the liposomes, to drug loading or to the intercalation of molecules within the lipid bilayer. In addition, lipid concentration is used to effectively evaluate drug-to-lipid ratios. For example, doxorubicin-to-lipid ratios of 0.3:1 led to an increase in biological activity in mice.

Liposomal lipid concentrations may be toxic depending on the type of lipid in the liposome composition. For example, phosphatidylglycerol and phosphatidylserine liposomes were toxic from 0.13-3.0 mM for some cultured human cell lines whereas dipalmitoylphosphatidylcholine containing liposomes were non-toxic at 4 mM. In addition, certain lipid concentrations may promote cytotoxicity and can be used as a measure to determine drug effects on changes in $IC_{50}$-values. For example, amphotericin B containing liposomes increased the $IC_{50}$-value in a macrophage-like cell line (Raw 264.7) when compared to liposomes without amphotericin B. Moreover, macrophage cells are major sites of liposomal accumulation and high lipid concentrations may cause macrophage cells to exhibit phospholipid overload and inhibit phagocytic function.

FDA-approved drug products are formulated with total lipid concentrations ranging from 9.15 mg/mL up to 103 mg/mL, with the majority in the range from 9.15 mg/mL-34.88 mg/mL. This provides a pharmaceutically relevant range of lipid concentrations that are considered safe and effective.

At this stage in the process, the liposomes created in the liposome creation stage are concentrated for further processing and purification. As shown in FIG. 8, the concentration stage is a continuous process using sensors such as an NIR sensor combined with a tangential flow filtration device, a pump and a custom developed computer program that may be used to control the concentration of the final product liposomes. Such an NIR sensor may be a dual channel turbidity sensor using two simultaneous channels, i.e. light absorption and light scattering. The concentration information determined from this stage of the process will be fed back to control when the liposomes pass to a subsequent stage that consists of the addition of molecules to be encapsulated inside the liposomes.

In certain embodiments, such as shown in FIGS. 1-8, one or more components (e.g., injection port, the three-way port, the first conduit, the second conduit, etc.) may be made using an additive-manufacturing process, such as stereolithography. As such, the example injection ports described above may include a variety of materials, including calcium carbonate of poly(dimethylsiloxane) (PDMS), as examples. In such an example, the one or more components described above may represent a module, a segment, or a portion of program code, which includes one or more instructions executable by a processor or computing device for creating such devices using an additive-manufacturing system. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

Figure 9:
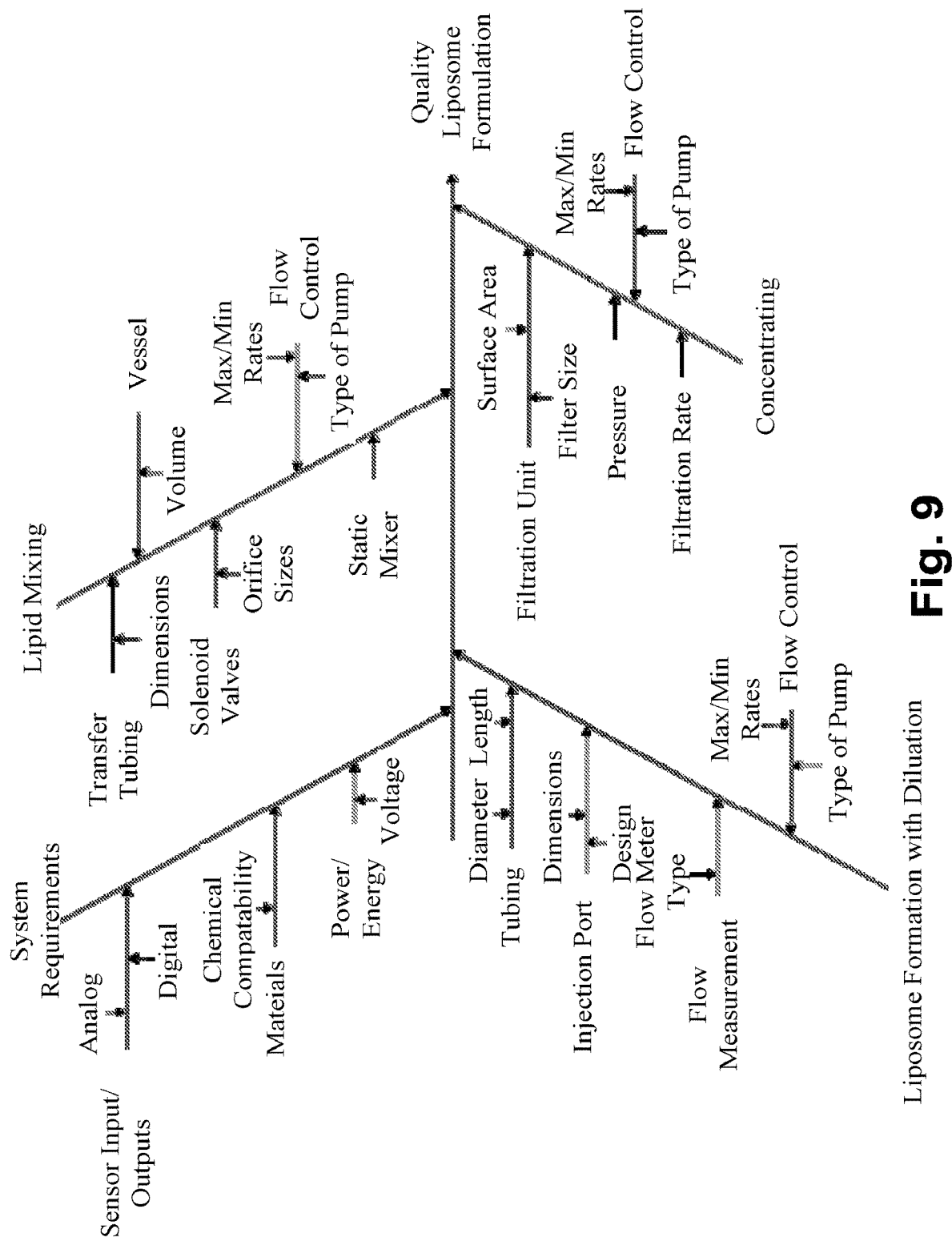
FIG. 9 is a cause and effect diagram highlighting the main stages of the continuous process with subdivisions for each main stage, according to an example embodiment.

FIG. 9 illustrates is a cause and effect diagram highlighting the main stages of the continuous process with subdivisions for each main stage, according to an example embodiment. FIG. 9 illustrates a cause and effect diagram for the entire process with the single effect of forming a "quality liposome formulation." For a quality liposome formulation, the process would need to achieve sufficient control (e.g. control of particle size and particle size distribution), be reproducible and accurate, and have the ability to be adaptable to cover formulation changes.

Figure 10:
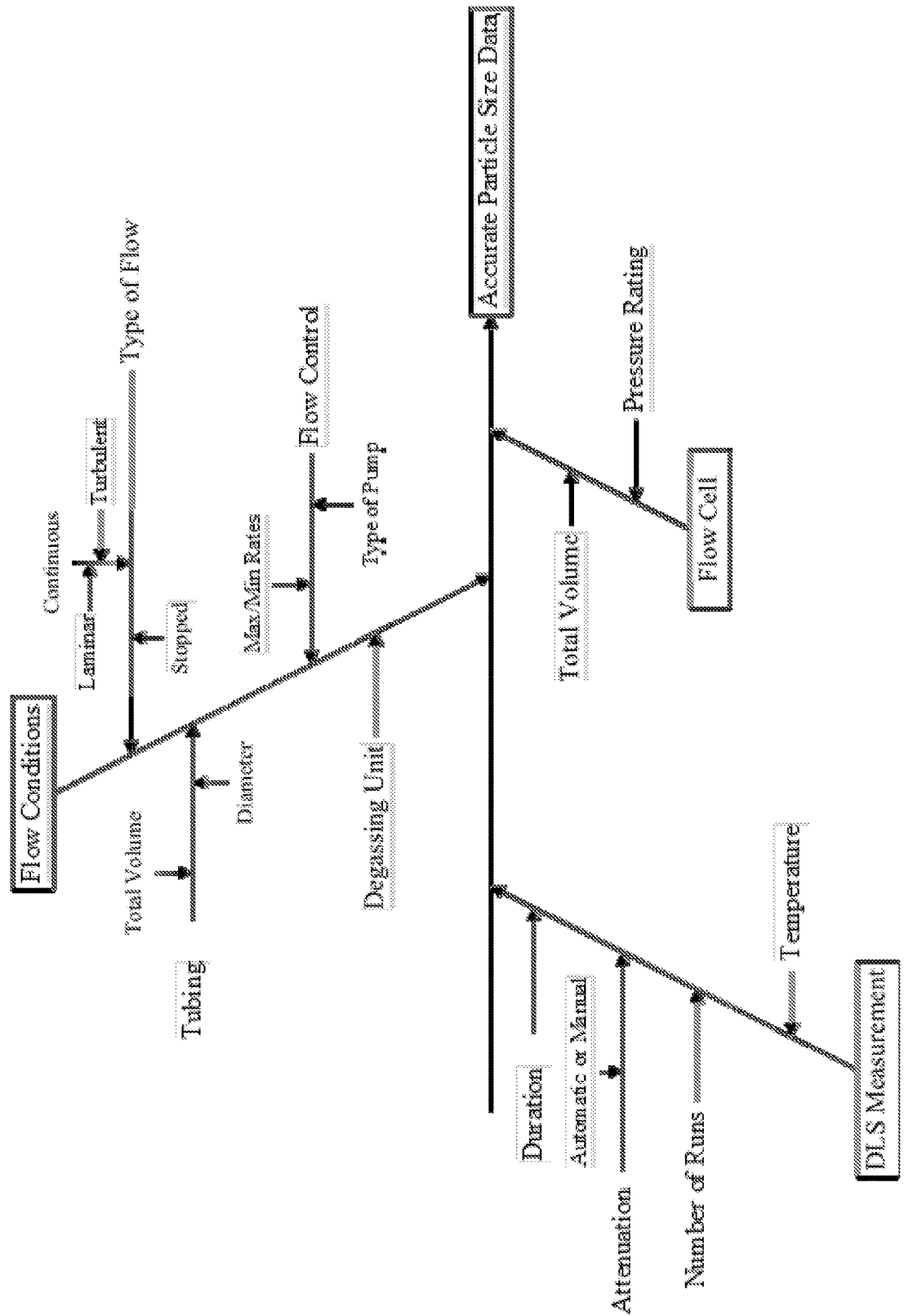
FIG. 10 is a cause and effect diagram outlining variables that result in obtaining accurate particle size data for a continuous process, according to an example embodiment.

FIG. 10 illustrates a cause and effect diagram outlining variables that result in obtaining accurate particle size data for a continuous process, according to an example embodiment. The effect/outcome of this diagram was the accurate measurement of particle sizing data for a continuous process. The causes were subdivided into flow conditions, flow cell and dynamic light scattering (DLS) measurement. The flow conditions outlined how to control the flow of the sample to the instrument (e.g. pump selection) and flow requirements (e.g. continuous and laminar flow vs. stopped flow). The flow cell has limitations such as the total volume of the flow cell and the pressure rating, which would limit the flow rate of the sample through the flow cell. Lastly, DLS measurement parameters will further impact the accuracy of particle sizing data. These parameters include temperature, measurement duration (e.g. 10 seconds), number of runs per measurement and the attenuation setting. As DLS uses a macroscopic fitting algorithm to determine the particle size, the sample temperature and photon count rate will impact the particle size analysis. For example, if the temperature is set at 25° C., but the sample temperature is actually 22° C., then the measured particle size may be higher than actual since particles move more slowly at lower temperatures than higher temperatures. In this case, the set temperature and the actual sample temperature are preferably similar to achieve accurate results. As a second example, the photon count rate is the rate at which photons are detected. For low count rates, there is not enough information for the macroscopic fitting algorithm to determine the particle size. In addition, at higher count rates, the DLS detector may no longer be operating in a linear range. Therefore, a range of count rates should be determined that provide accurate data.

Figure 11:
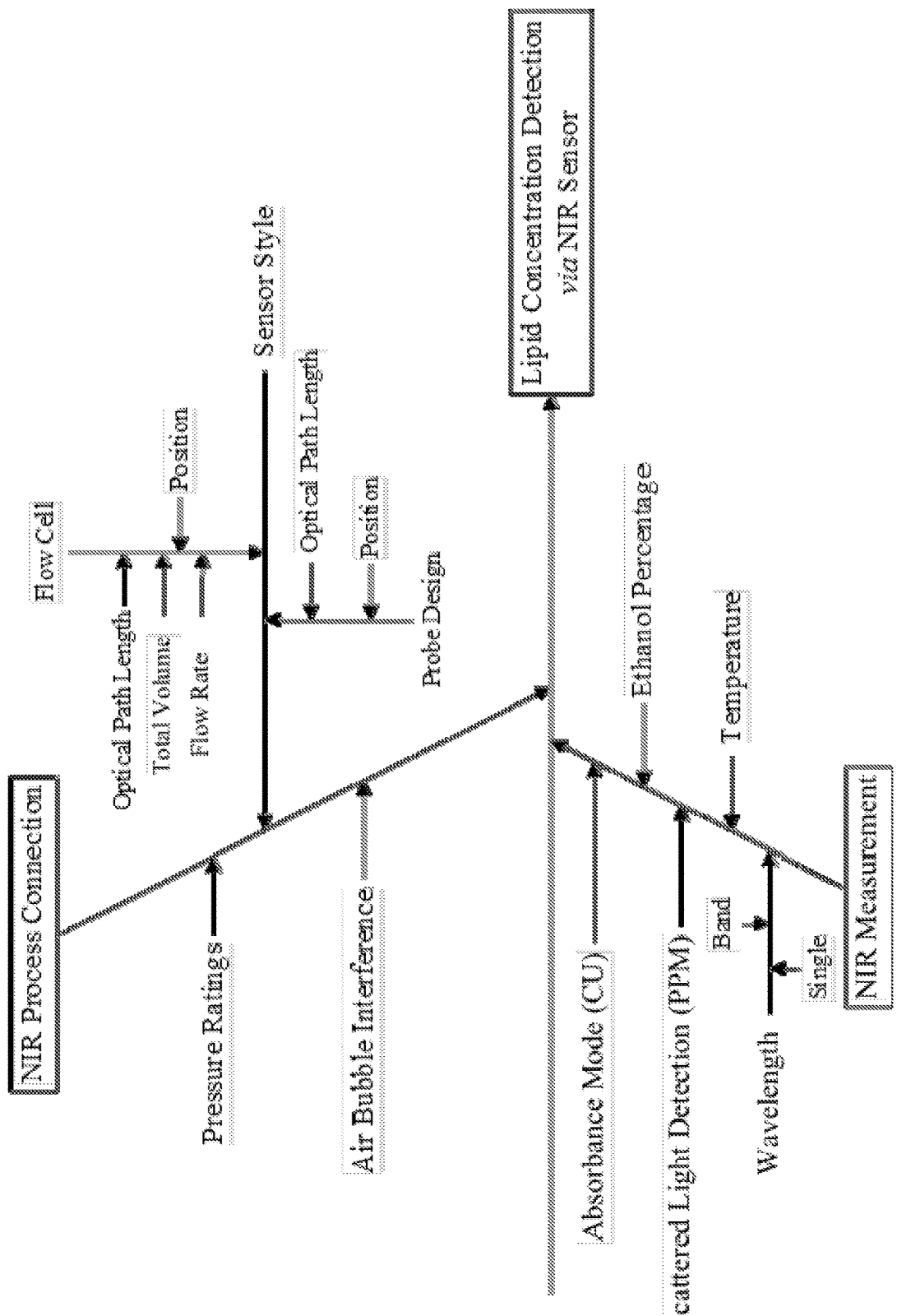
FIG. 11 is a cause and effect diagram outlining variables that affect the lipid concentration detection via an NIR sensor, according to an example embodiment.

FIG. 11 illustrates a cause and effect diagram outlining variables that affect the lipid concentration detection via an NIR sensor, according to an example embodiment. For instance, there are a two common NIR sensor styles, i.e. a probe design or a flow cell design. The probe design may be more prone to air bubble accumulations at the detection window. In addition, the probe design may have a limited optical path length (e.g. up to only 10 mm), whereas the flow cell design may have longer optical paths (e.g. up to 160 mm). The longer optical path would accommodate samples that scatter a small amount of light (i.e. smaller diameter particles at low concentrations). In addition, NIR probes may be designed at a single wavelength or a band of wavelengths and at various angles of detection. For angles of detection that are 0° from the light source, the measurement is referred to as absorbance and measured in units such as CU. Scattered light may be detected at angles such as 11° or 90°. For the scattered light, the unscattered light is used as a reference to account for changes in the aqueous medium.

Figure 12:
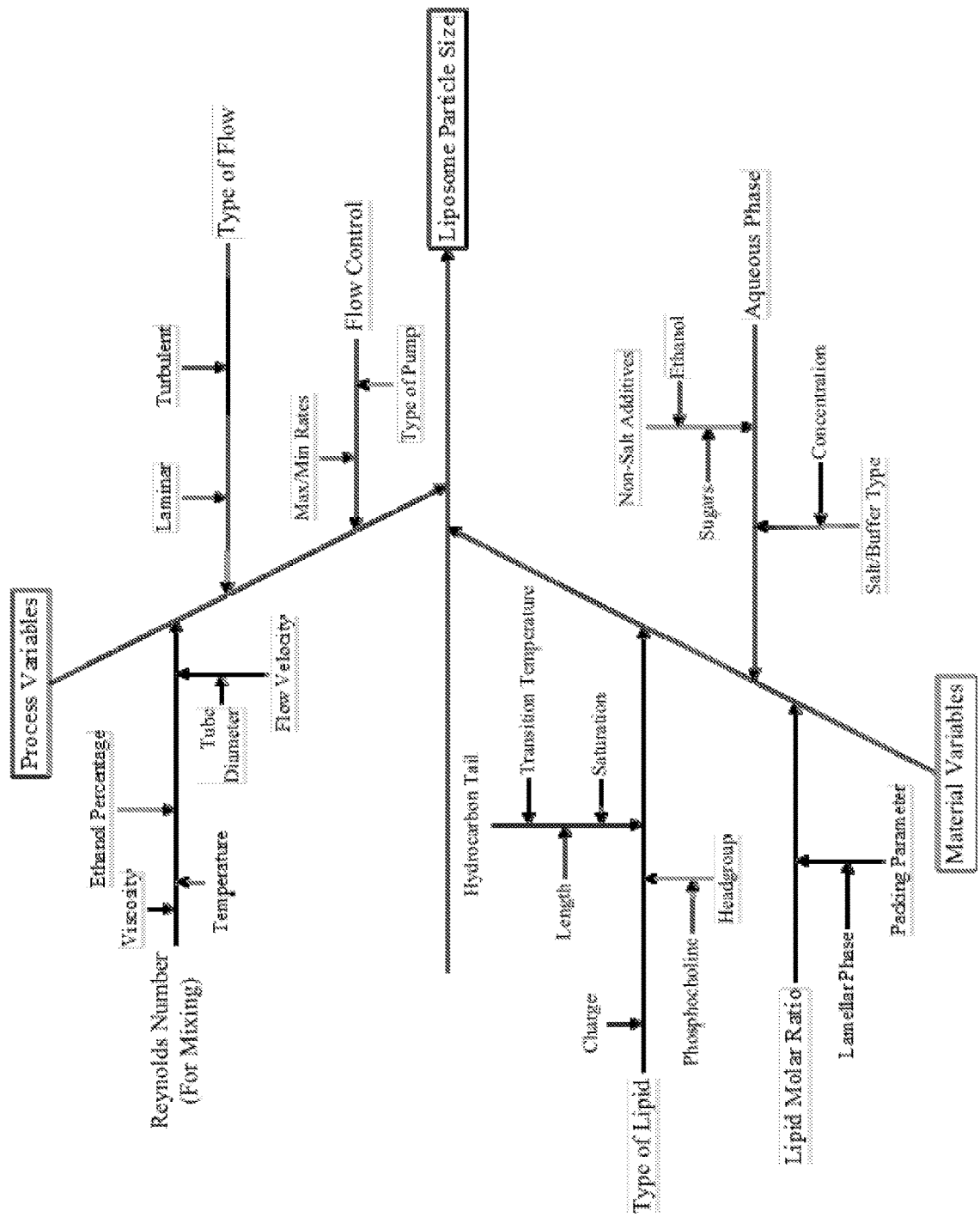
FIG. 12 is a cause and effect diagram outlining variables that affect the liposome formation process with respect to material and process variables, according to an example embodiment.

FIG. 12 illustrates a cause and effect diagram outlining variables that affect the liposome formation process with respect to material and process variables, according to an example embodiment. The causes are divided into process variables, material variables and lipid molar ratio. The process variables includes types of flow (e.g. laminar vs. turbulent), type of pump (e.g. pulsatile vs. non-pulsatile) and Reynolds number. The Reynolds number is a means to determine the extent of mixing—with a higher Reynolds number indicating a greater extent of mixing. The Reynolds number is dependent on viscosity, temperature and flow velocities. The material variables are subdivided into type of lipid and aqueous phase. The type of lipid will significantly impact the liposome particle size. For example, each lipid has a transition temperature, which indicates the fluidity of the lipid at a certain temperature. Lipids that may be in the fluid state could possibly form larger liposomes; however, this is not clearly understood at this time. The lipid molar ratio is another cause that my affect the liposome particle size. As many liposomal formulations consist of multiple lipids, the combination of the lipids preferably result in a packing parameter that supports the lamellar structure; otherwise, liposomes will not form. Therefore, the lipid ratio of, for example, cholesterol and other lipids preferably equates to approximately 1 in order to support a lamellar phase—which is the phase that will form liposomes.

Figure 13:
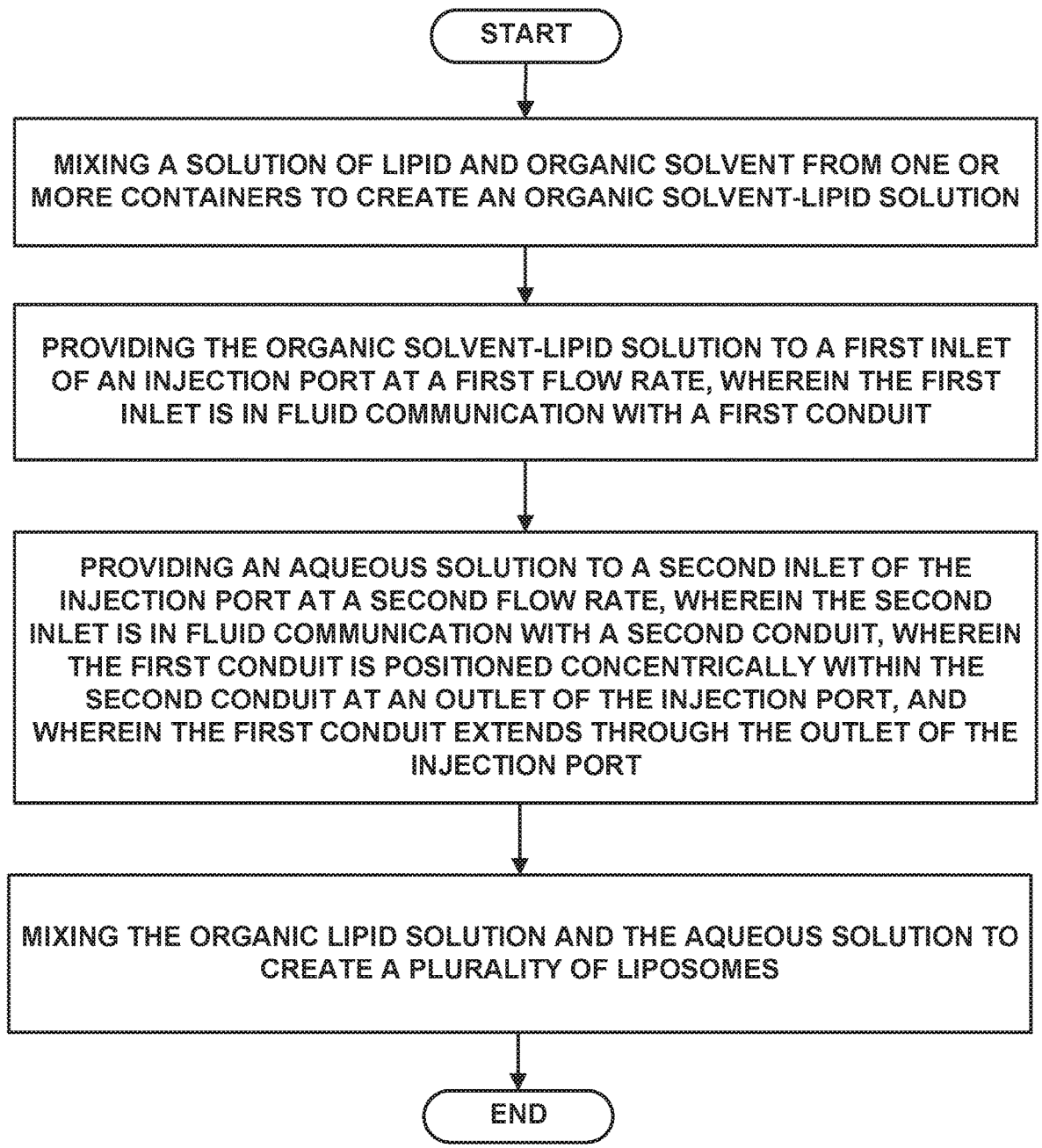
FIG. 13 is a flowchart illustrating an example method according to an example embodiment.
Figure 14:
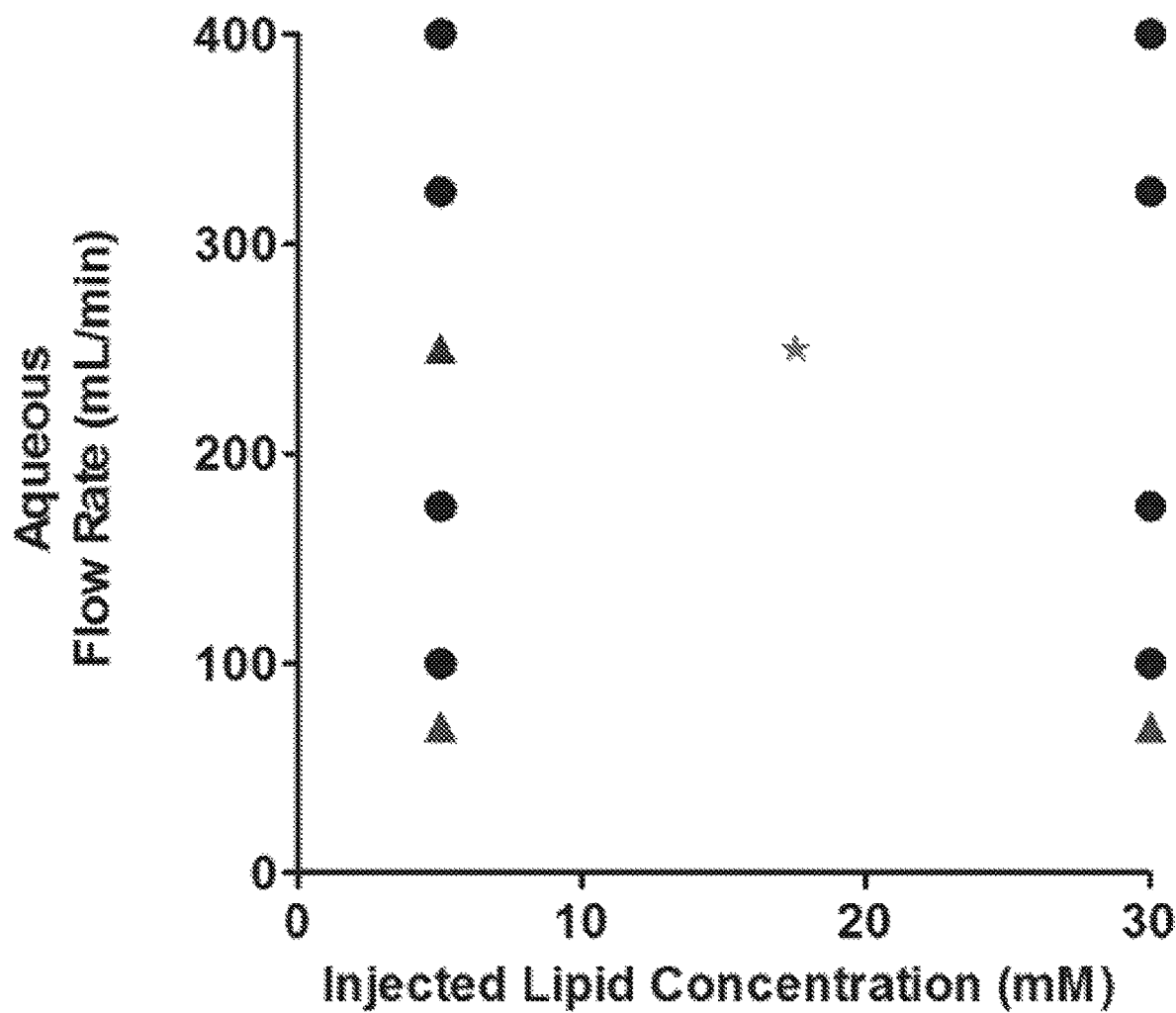
FIG. 14 is a design space of the DOE study on the impact of lipid concentration and aqueous phase flow rate on particle size, according to an example embodiment.

FIG. 13 is a block diagram of an example method for the continuous production of liposomes. The method shown in FIG. 13 presents an embodiment of a method that could be used by one or more of the components described above in relation to FIGS. 1-12. The example method may include one or more operations, functions, or actions as illustrated by the blocks in FIG. 13. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

In addition, for the method and other processes and methods disclosed herein, the block diagram shows functionality and operation of one possible implementation of present embodiments. In this regard, each block may represent a module, a segment, or a portion of program code, which includes one or more instructions executable by a processor or computing device for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

In addition, for the method and other processes and methods disclosed herein, each block in FIG. 13 may represent circuitry that is wired to perform the specific logical functions in the process.

As shown in FIG. 13, one example method for the continuous production of liposomes comprises (a) mixing a solution of lipid and organic solvent from one or more containers to create an organic solvent-lipid solution, (b) providing the organic solvent-lipid solution to a first inlet of an injection port at a first flow rate, wherein the first inlet is in fluid communication with a first conduit, (c) providing an aqueous solution to a second inlet of the injection port at a second flow rate, wherein the second inlet is in fluid communication with a second conduit, wherein the first conduit is positioned concentrically within the second conduit at an outlet of the injection port, and wherein the first conduit extends through the outlet of the injection port, and (d) mixing the organic lipid solution and the aqueous solution to create a plurality of liposomes.

In one example, the first flow rate is between about 5 mL/min and about 40 mL/min, and the second flow rate is between about 70 mL/min and about 300 mL/min. In one example, a first flow of the organic solution through the first tube and a second flow of the aqueous solution through the second tube are under laminar or transitional flow conditions. When the two streams interact, a turbulent mixing patter is formed since the flow rate of each stream is different. In another example, a first flow of the organic solution through the first tube and a second flow of the aqueous solution through the second tube are turbulent flow. Further, in one example the aqueous solution comprises an aqueous-organic solvent mixture, and the plurality of liposomes are unilamellar liposomes.

In another embodiment, the method may further comprise determining a size of one or more of the plurality of liposomes created within the second tube, determining a difference between a desired size of the one or more liposomes and the determined size of the one or more liposomes, and in response to the determined difference, adjusting at least one of the second flow rate and a lipid concentration of the organic lipid solution. In one example, the determining of the size of one or more of the plurality of liposomes is done while the plurality of liposomes move at a constant flow rate. In another example, the determining of the size of one or more of the plurality of liposomes comprises momentarily stopping a pump to prevent fluid flow of the one or more of the plurality of liposomes, determining the size of one or more of the plurality of liposomes while the plurality of liposomes are at rest, and starting the pump to resume fluid flow.

In another embodiment, the method may further comprise determining a size distribution of one or more of the plurality of liposomes created within the second tube, determining a difference between a desired size distribution of the one or more liposomes and the determined size distribution of the one or more liposomes, and in response to the determined difference, adjusting at least one of the second flow rate and a lipid concentration of the organic lipid solution.

In another embodiment, the method may further comprise passing the plurality of liposomes to a degassing unit, passing the plurality of liposomes from the degassing unit to a first port of a three-way port, providing an aqueous buffer to a second port of the three-way port at a third flow rate, and mixing the plurality of liposomes and the aqueous buffer. In such an example, the mixture of the plurality of liposomes and the aqueous buffer have about 5% volume ethanol. Further, in such an example the third flow rate may be between about 300 mL/min and about 10000 mL/min.

In another embodiment, the method may further comprise determining a total lipid concentration of the plurality of liposomes, determining a difference between a desired total lipid concentration of the liposomes and the determined total lipid concentration of the liposomes, and in response to the determined difference, adjusting the second flow rate and/or adjusting a lipid concentration of the organic lipid solution.

In yet another embodiment, the method may further comprise passing the plurality of liposomes to a tangential flow filtration unit, determining a total lipid concentration of the plurality of liposomes, determining a difference between a desired total lipid concentration of the liposomes and the determined total lipid concentration of the liposomes, and in response to the determined difference, adjusting a permeate flow rate of the tangential flow filtration unit and/or adjusting a pressure of the tangential flow filtration unit. In such an example, the total lipid concentration of the plurality of liposomes may be determined via an NIR sensor.

Example 1

Abbreviations

Reynolds Number—Re
Flow Velocity Ratio—FVR
Dynamic Light Scattering—DLS
Polydispersity Index—PDI
Design of Experiment—DOE
31 Phosphorous Nuclear Magnetic Resonance—P-NMR
1,2-dimyristoyl-sn-glycero-3-phosphocholine—DMPC
1,2-dipalmitoyl-sn-glycero-3-phosphocholine—DPPC
1,2-distearoyl-sn-glycero-3-phosphocholine—DSPC
1,2-dipalmitoyl-sn-glycero-3-phospho-(1'-rac-glycerol) (sodium salt)—DPPG
1,2-dioleoyl-sn-glycero-3-phosphocholine—DOPC
Cholesterol—Chol
Negative Stain Transmission Electron Microscopy—NS-TEM
Cryogenic Transmission Electron Microscopy—Cryo-TEM
National Instruments—NI
International Conference on Harmonisation—ICH
Process Analytical Technology—PAT
Combined Output Flow Rate—Q
Kinematic Viscosity—v
Diameter—D
Outer Diameter—OD
Inner Diameter—ID
Cross-Sectional Area—A
Materials and Methods:

Overview of Process with Turbulent Mixer

Liposomes were prepared by a modified ethanol injection method. A schematic of this system is demonstrated in FIG. 1. Three separate 316 stainless steel tanks were fabricated to house the lipid+ethanol solution. These tanks were pressurized (at typically 20 psi) and the flow rates from these tanks were controlled by analog flow meters (McMillian) and proportioning solenoid valves (Aalborg). The flow meters were factory calibrated for water with less than 1% error. For the lipid+ethanol flow streams, these flow sensors were re-calibrated for ethanol and had an R-squared value of 0.9989, with a working range from 5-50 mL/min. The three tanks were then connected at a single point using a 4-way connector (Swagelok). A static mixer was implemented to ensure that the lipid+ethanol solutions from the three tanks were adequately mixed prior to reaching the injection port where the ethanol and aqueous streams converged. The aqueous phase volumetric flow rate was controlled by a gear pump (Micropump®). The mixed lipid+ethanol solution was then injected into the aqueous phase at various flow rates. The tubing ID of the ethanol phase was 0.508 or 1.016 mm (1.588 mm OD). The aqueous phase tubing ID was fixed at 3.175 or 4.572 mm. Typical flow rates of the lipid+ethanol phase were from 5-40 mL/min and of the aqueous phase were from 60-400 mL/min.

The entire process was controlled by a custom-made program written using National Instruments (NI) LabVIEW® software. A data acquisition system (NI PXIe-1078) was combined with multiple NI modules to accommodate various input/output signals (e.g. analog and digital inputs/outputs, counters, circuit switches, etc.). The entire system was automated and only required the user to define the final lipid concentration and molar ratios of lipid. Process variables such as flow rates, pressure, and temperature were monitored and, for some variables, automatically adjusted using custom computer algorithms. For example, proportional-integral-derivative controls were implemented in the computer program to precisely control the flow rates of both the ethanol and aqueous phases.

Liposome Preparation 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-dipalmitoyl-sn-glycero-3-phospho-(1'-rac-glycerol) (sodium salt) (DPPG) and 1,2-dioleoyl-sn-glycero-3-phosphocholine (DOPC), were purchased from Lipoid™. Cholesterol (Chol) was purchased from Sigma. The lipid (5-30 mM total lipid) was dissolved in ethanol (USP grade) and added to one of the three tanks. To dissolve the lipid in ethanol, the lipid mixture was typically heated to 60° C. for 10 minutes and sonicated for 5 minutes or until all of the lipid was fully dissolved. The ethanol solution was then allowed to reach room temperature (23° C.) prior to running any experiment. In some cases, the entire lipid was combined into a single tank and pure ethanol was added to the other tanks for dilution.

Dynamic Light Scattering for Particle Size and Zeta-Potential Measurements were performed with a Malvern Zetasizer Nano ZS90 for zeta potential and a Malvern Zetasizer Nano S for size. The samples were placed in plastic disposable cuvettes (or a capillary cell for zeta-potential) and equilibrated to 25° C. prior to measurements. Since ethanol was present in the samples, all samples were diluted to 1.64% v/v (ethanol/total solution) and the viscosity and refractive index were adjusted for in the Malvern Zetasizer software. Particle size measurements included the z-average, PDI, volume percentage, intensity mean and intensity width. Zeta potential measurements included zeta-potential and zeta deviation. All measurements were run in triplicate.

Flow Visualizations

Nile Red (Sigma-Aldrich®) was used as the dye and was dissolved in ethanol. This solution was added to one of the three pressure tanks. Lipid dissolved in ethanol was added to a second tank. The lipid and Nile Red solutions were run at a 1:1 volumetric ratio under different flow conditions. As Nile Red changes color based on solution polarity, the solution appeared pink in ethanol, pink/orange with lipid dissolved in ethanol and purple/bluish when dissolved or mixed with water without lipid.

Nanoparticle Tracking Analysis

Measurements were performed with a Malvern Nanosight™ instrument. The samples were diluted down to 0.05% v/v ethanol. In some cases, additional dilution was necessary to reach acceptable conditions for particle size analysis (e.g. as vesicle diameter decreases, the number of vesicles increased exponentially). As for the measurements, the mean and standard deviation were recorded. All measurements were run in triplicate.

Negative Stain Transmission Electron Microscopy (NS-TEM)

Liposomes were prepared in 10 mM ammonium acetate-acetic acid buffer at pH 5.00. For each sample, approximately 3 µl of liposomes was placed on a plasma cleaned carbon coated grid (Ted Pella Inc, #01840). After 1 minute incubation, the sample was flooded with several drops of 0.25% of uranyl acetate stain. The excess solution was blotted off and the sample was air dried for approximately 30 minutes. The grid was imaged at 80.0 kV in an FEI Tecnai 12 Biotwin TEM equipped with a LaB6 emitter and an Advanced Microscopy Techniques 2k XR40 CCD camera.

For each sample, 7-10 images were collected and the diameter of more than 500 particles/sample were manually measured using ImageJ. The data was then collected and the mean particle size and standard deviations were determined by fitting a nonlinear analysis using a Gaussian distribution fitting function.

Cryo-Transmission Electron Microscopy (Cryo-TEM)

Cryo-TEM was performed using cryo-transmission electron microscopy (Jeol 1400 TEM/STEM) operated at 120 kV and viewed under the Minimum Dose System. Briefly, 2 µL of liposome sample was placed on a glow-discharged Holey carbon copper grid (Quantifoil R 2/1). Using a grid plunge freezer (Leica EM GP) at 25° C. and 82% humidity, samples were blotted automatically for 2 s to remove excess liquid and plunged into a bath of liquid ethane at −175° C. The samples were stored in liquid nitrogen until they were transferred to a cryo-TEM holder (Gatan 914) and observed in the pre-cooled cryo-TEM at 120 kV under Minimum Dose System. Images were recorded with a digital CCD Camera (Gatan ORIUS™ SC1000) at magnification of 10000×-20,000×.

Design of Experiment Study

A design of experiment was performed to analyze the lipid concentration and aqueous phase flow rates on liposome particle size. The aqueous phase flow rate range was designed to cover a broad range of flow conditions that led to low and high Reynolds Numbers. In addition, these flow rates cover the full range of the system processing capabilities (i.e. pump flow rate working range). Lipid Concentrations studied were based on reported lipid wt % that would possibly lead to the formation of liposomes. A custom 2×4 full factorial design with 5 center-points, and 3 repeats was chosen as the initial design (FIG. 2). This design was chosen to support interaction and higher order terms as well as stay within constraints on the final ethanol percentage. The original design was augmented to increase the design space and to increase the statistical significance of the model (FIG. 2). With respect to model analysis, the r-squared term, analysis of variance ($p<0.05$) and lack of fit p-value ($p>>0.05$) were used to determine adequate fitting and the inclusion of model interaction terms. Only the Malvern Zetasizer Nano S was used to determine the particle size and PDI for this study. The model design and analysis was conducted using JMP by SAS.

Reynolds Number and Flow Velocity Ratio Calculations

The Reynolds number (Re) is defined as Re=QD/vA, where Q is the combined output flow rate, v is the kinematic viscosity of the mixture, D is the diameter of the output tube and A is the cross-sectional area of the output tube. The kinematic viscosity was calculated for the final ethanol-water mixture based on reported dynamic viscosity and density values. An equation was created using JMP by SAS to predict the kinematic viscosity with dependence on ethanol mole fraction and the output temperature. As the enthalpy of mixing for water and ethanol mixtures is exothermic, the final output temperature varied from the initial temperatures of both phases (i.e. 23° C.) up to ~32° C. These temperatures were recorded for the various flow conditions and were used in the Re calculation. The flow velocity ratio (FVR) is $FVR=v_i/v_o$, where $v_i$ is the inner tube velocity and $v_o$ is the outer tube velocity. Both velocities are calculated directly from the volumetric flow rates and the geometry of the tube. For the outer tube velocity calculation, the inner tube outer diameter was subtracted from the outer tube inner diameter.

Results:

Mixing of Ethanol and Aqueous Phase

Figure 15:
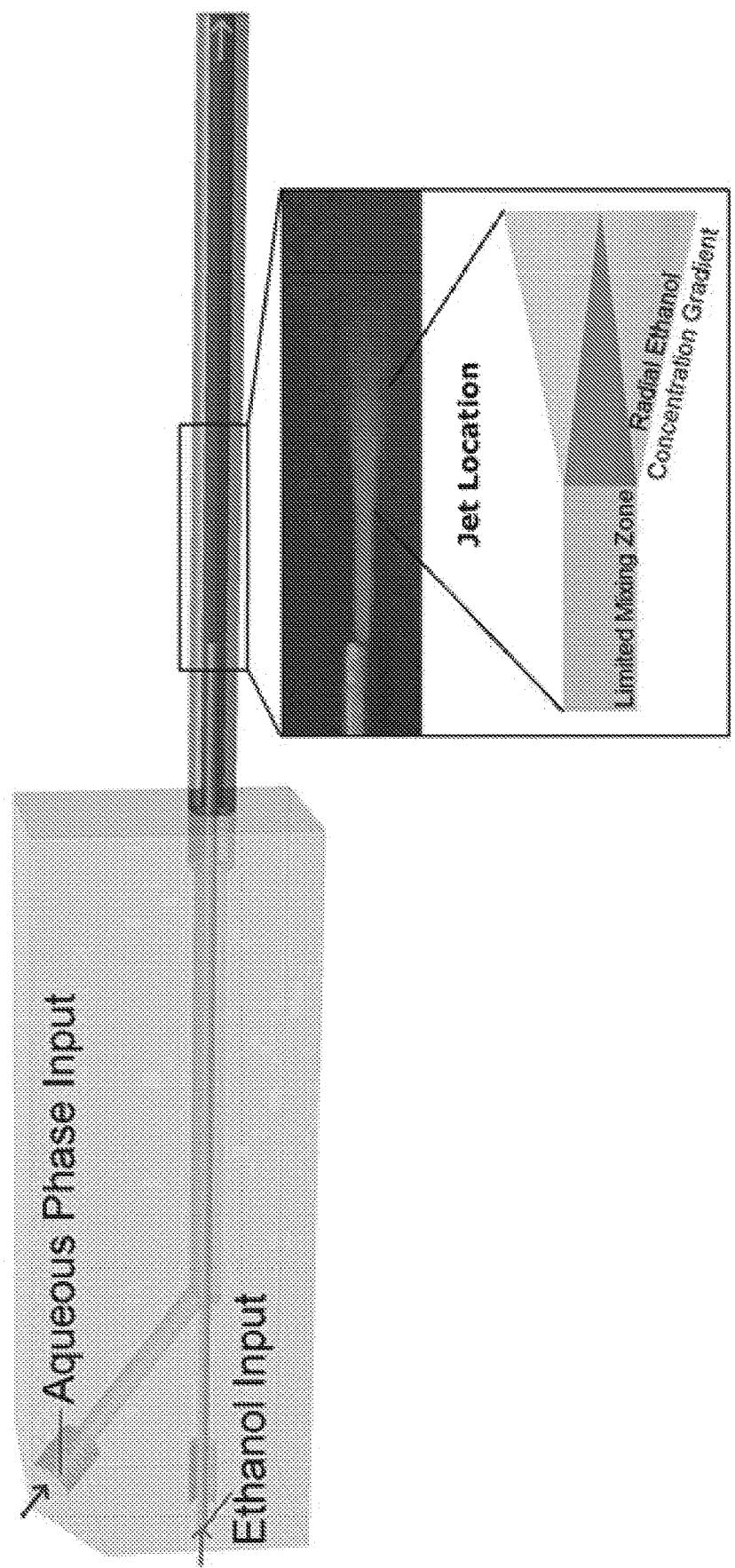
FIG. 15 is a schematic and photographic image of the injection port that allows formation of a coaxial turbulent jet, according to an example embodiment.

An injection port was fabricated to accommodate the formation of a coaxial turbulent jet in co-flow. A cylindrical tube (first conduit) designed to carry the ethanol phase was positioned concentrically within second or outer cylindrical tube (FIG. 15). The second cylindrical tube (second conduit) carries the aqueous phase prior to jet formation. There are three criteria useful to achieve suitable conditions for a stable turbulent jet. The first is that all flow rates may be pulseless to reduce flow rate fluctuations to negligible levels. The second two criteria come from non-dimensional values of fluid dynamics: (1) Reynolds number (Re) and (2) flow velocity ratio (FVR). The Re is that of the mixed ethanol/aqueous flow stream just downstream of the "jet location" and will subsequently be referred to as the $Re_{mixture}$.

Relationship Between Fluid Flow Properties and Liposomal Polydispersity Index

The fluid flow properties of the injection port were related to the liposome polydispersity index. Liposomes were analyzed using dynamic light scattering (DLS) and a polydispersity index (PDI) of 0.10 was considered as the upper limit for monodispersity. The ethanol flow rate ranged from 5-40 mL/min and the aqueous phase flow rate ranged from 70-400 mL/min. The organic phase consisted of DPPC:DPPG:Chol (4.5:0.4:3 molar ratio) dissolved in ethanol and the aqueous phase was 10 mM phosphate buffer, pH 7.4. The inner tube diameter was 0.508 mm or 1.016 mm. The outer tube diameter was 3.175 mm or 4.572 mm. In addition, the maximum final ethanol percentage was chosen to be less than 40% v/v ethanol to reduce the possibility of forming any non-liposomal structures. For this lipid formulation, the average zeta-potential was −39.4±6.34 mV (averaged for all samples).

The flow rates were transformed to $Re_{mixture}$ and FVR as outlined in the methods section. To achieve various $Re_{mixture}$ and FVR combinations, different inner and outer tube diameters were investigated. From FIG. 16A, it is clear that in order to achieve a monodispersed system, certain $Re_{mixture}$ and FVR combinations are useful to form a stable jet. FIG. 16B depicts the fluid profiles of four locations on the FVR vs. $Re_{mixture}$ plot from FIG. 16A. At a $Re_{mixture}<500$ and FVR<7, a stratified flow is observed with the lipid+ethanol staying separated and moving to the top of the tubing (FIG. 16A-1). Limited mixing occurs in this case and the actual lipid mixing/liposome formation would occur downstream (i.e. possibly in the collection vessel)—leading to polydispersed liposomes. At FVR≤2 and $Re_{mixture}>~500$, a weak jet forms and this also leads to polydispersed liposomes (FIG. 16B-2). The other two flow conditions depicted lead to rapid mixing downstream of the injection site and stable jet formation, resulting in monodispersed liposomes (FIG. 16B-3 and FIG. 16B-4). In the case monodispersed liposomes, it is evident that liposome formation is dependent on mixing and can be predicted by the $Re_{mixture}$ (FIG. 16C). At a high FVR (i.e. ≥7), the liposome particle size is monodispersed and independent of FVR and only changes according to the $Re_{mixture}$. The latter case outlines that monodispersed liposomes may be formed under a variety of injection port dimensions that lead to the same FVR and $Re_{mixture}$ conditions.

Design of Experiment: Lipid Concentration Vs. Particle Size

Figure 17:
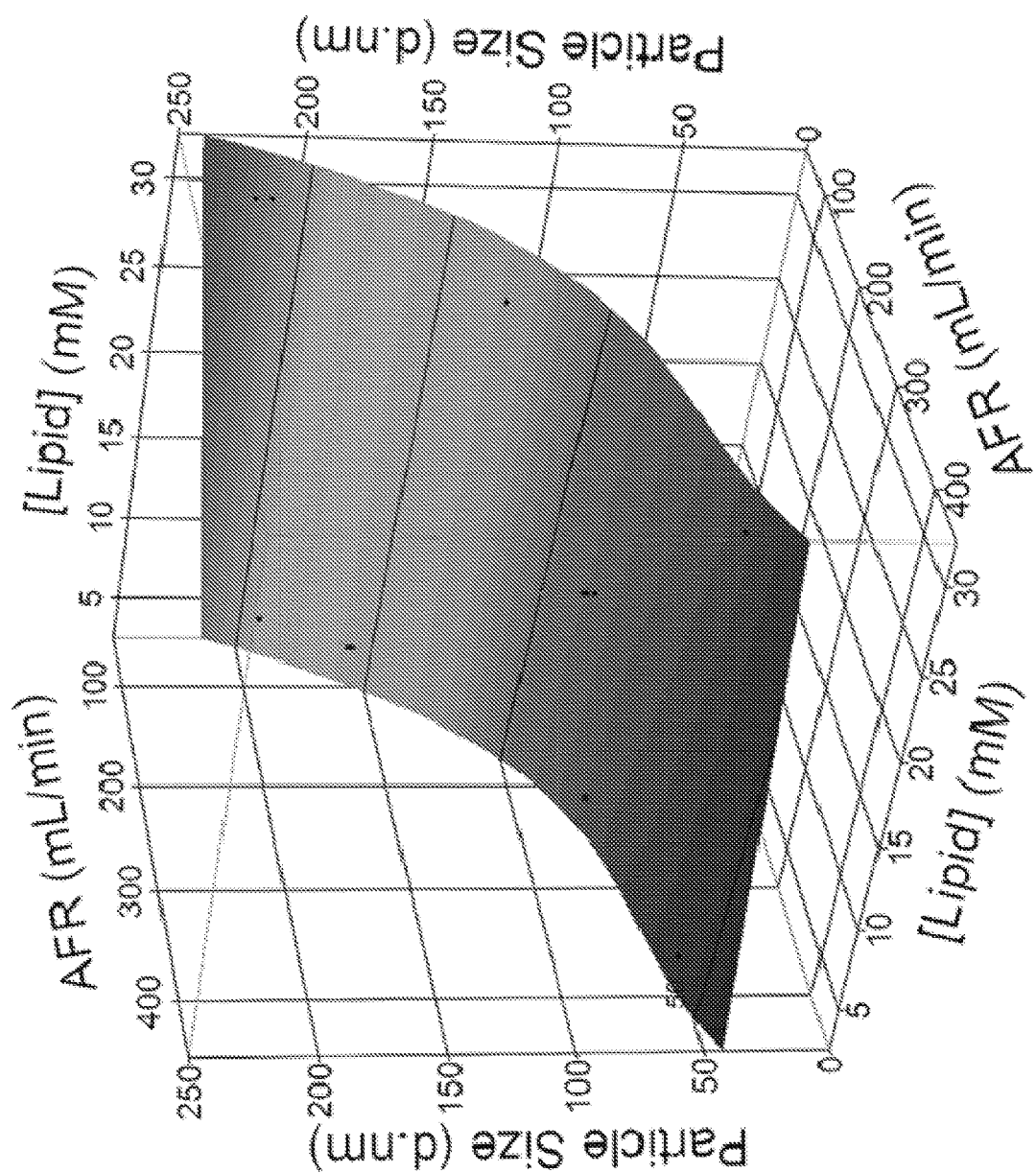
FIG. 17 is a surface profile plot of the Z-average particle size vs. the aqueous phase flow rate (AFR) and lipid concentration, according to an example embodiment.

A design of experiment (DOE) study was completed to demonstrate the effects of the injected lipid concentration on liposomal particle size for a monodispersed population of liposomes. The ethanol flow rate was fixed at 40 mL/min as this flow rate corresponding to a flow region that produces monodispersed particles (FIG. 16A). The dimensions of the injection port were fixed at an aqueous phase tubing ID of 3.175 mm and an ethanol phase tubing ID of 0.508 mm. For the DOE study, the factors included: (1) aqueous phase flow rate (70-400 mL/min) and (2) injected lipid concentration (5-30 mM). The aqueous phase was 10 mM phosphate buffer. The lipid composition was fixed at DPPC:DPPG:Chol (4.5:0.4:3 molar ratio). The DOE model has a $R^2$-value of the actual vs. predicted values of 0.985, an analysis of variance p-value <0.0001 and a lack-of-fit p-value=0.331 (FIG. 42). The surface profile for this study demonstrates the dependence of the mean particle size on the aqueous phase flow rate (FIG. 17). For this formulation, the smallest liposomes appeared around 58 nm and the largest around 240 nm. The PDI value averaged 0.05±0.04 for all experiments, and only started to reach 0.10 at the lower aqueous phase flow rates (e.g. 70 mL/min). Thus, the liposomes could be considered monodispersed over the entire range of flow rates studied. The lipid concentration had a modest positive impact on the particle size. It was apparent that the aqueous phase flow rate interaction terms were dominant in controlling the z-average liposome particle size.

Types of Lipid on Liposome Particle Size

Figure 18:
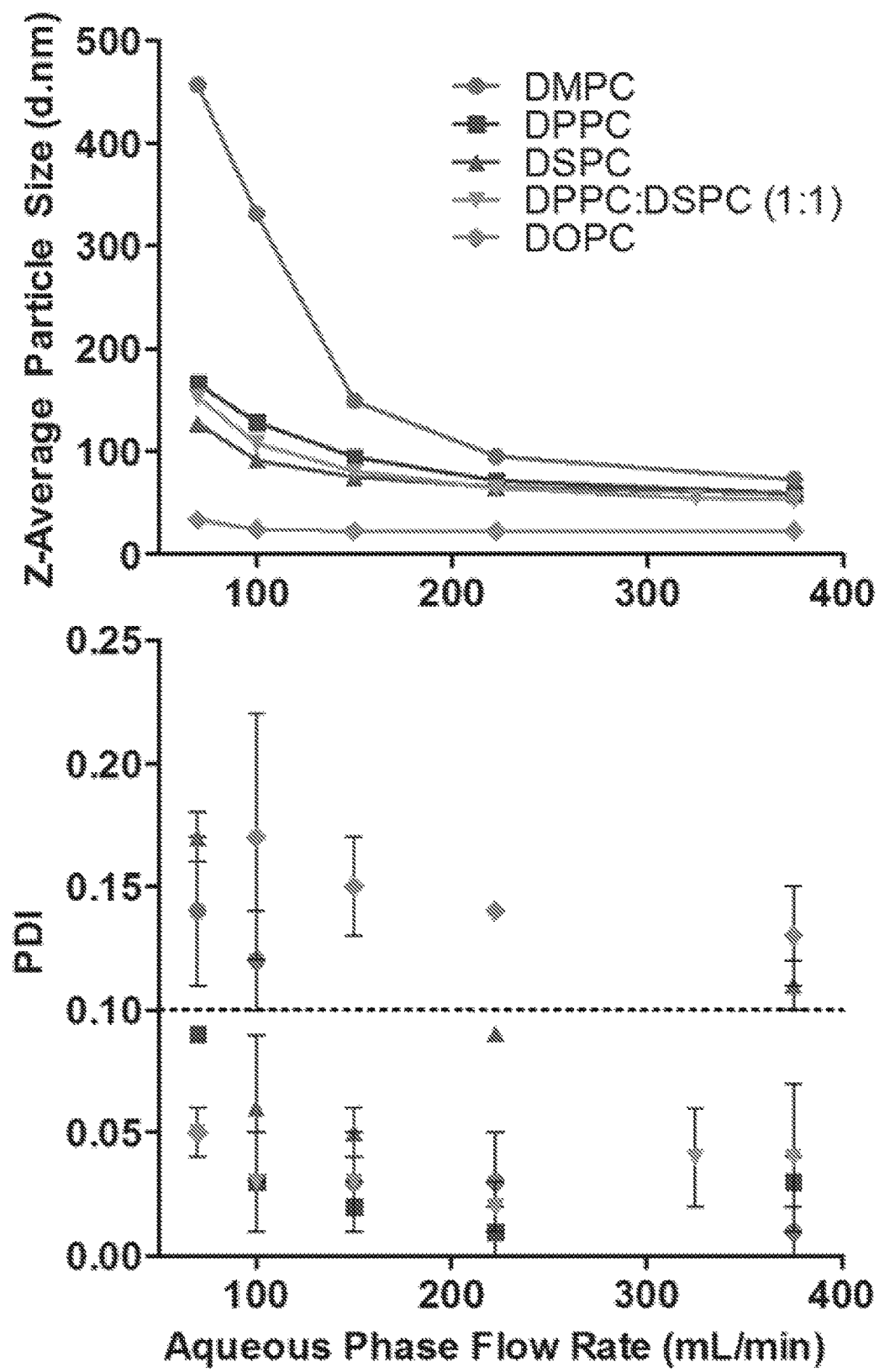
FIG. 18 is a graphical representation of the effect of lipid type (i.e. DMPC, DPPC, DSPC, DOPC) on mean particle size and PDI, according to an example embodiment.

From the results above, it is evident that the $Re_{mixture}$ and lipid concentration may play a role in controlling liposome particle size. To determine whether lipid characteristics affect liposome particle size, four different lipid molecules were investigated, namely DOPC, DMPC, DPPC, DSPC and a mixture of DPPC:DSPC (1:1 molar ratio). Each formulation also contained cholesterol and DPPG. The molar ratio was held constant for lipid:DPPG:Chol (4.5:0.4:3.0) and 5 mM total lipid was dissolved in the ethanol phase. The z-average particle size and PDI values are plotted (FIG. 18). It is clear that the lipid molecule significantly altered the liposome particle size. Liposomes with a mean particle size were controllably formed from approximately 25 nm up to 465 nm and the maximum PDI value was equal to 0.18; however, the PDI was ≤0.05 for the majority of the samples (FIG. 18).

Aqueous Phase Additives on Liposome Particle Size

Figure 19:
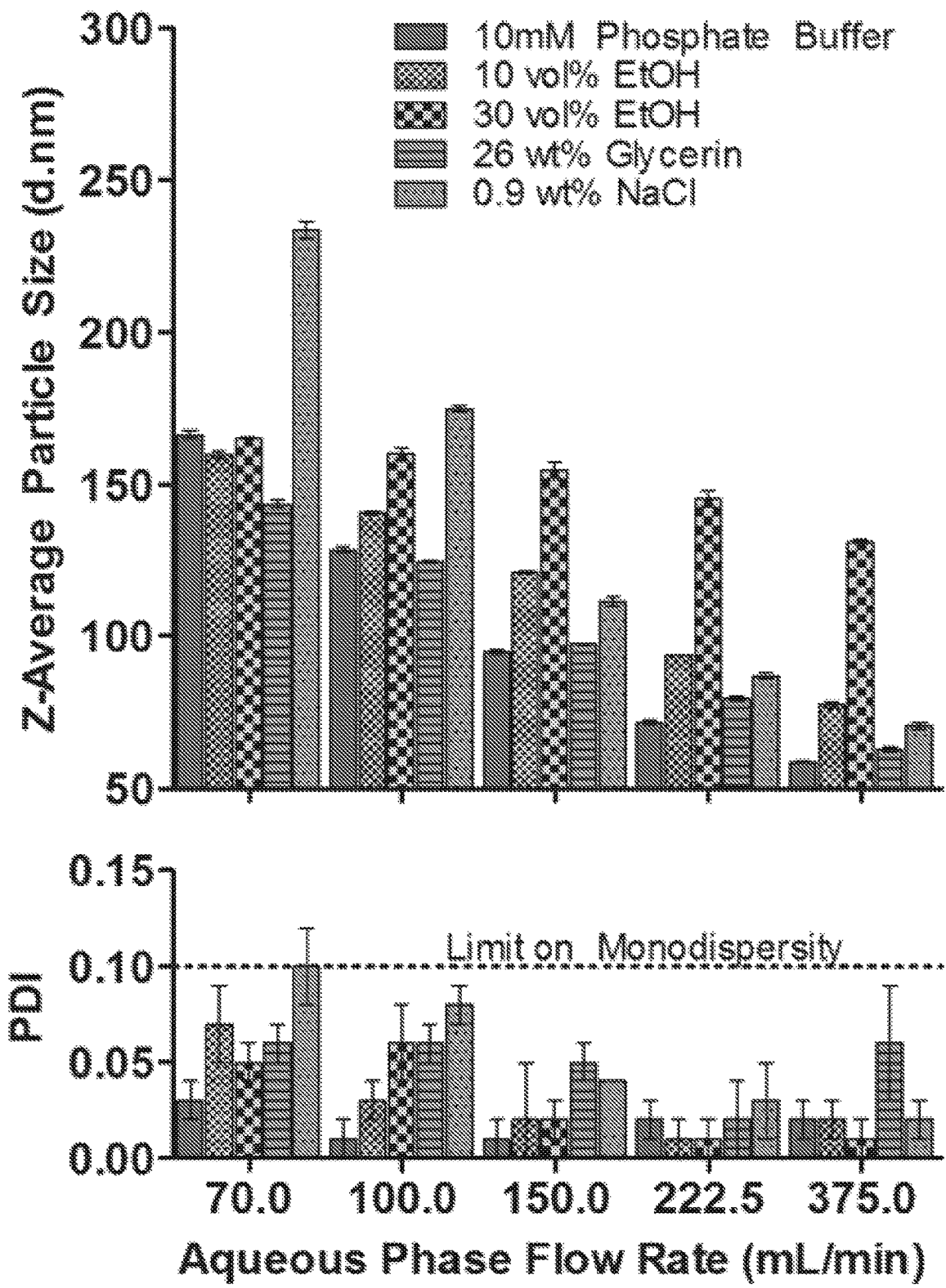
FIG. 19 is a graphical representation of the effect of aqueous phase additives on mean particle size, according to an example embodiment.

Additives to the aqueous phase were used to determine any impact on liposome formation. For this study, the lipid formulation was kept constant at DPPC:DPPG:Chol (4.5:0.4:3 molar ratio, 5 mM lipid injected) and all samples contained 10 mM phosphate buffer, pH 7.4. NaCl; glycerol; and ethanol were investigated as additives (FIG. 19). Liposomes prepared in 10 mM phosphate buffer with no additive was used as a control. For all flow conditions, the formulation containing 26 wt % glycerol was the most similar to the control. The addition of 10-30% v/v ethanol to the aqueous phase increased the particle size under most flow conditions. The 30% v/v ethanol addition caused the liposomes to be linearly dependent on the aqueous phase flow rate. The addition of 0.9 wt % NaCl dramatically increased the mean particle size under all conditions compared to the control.

Figure 20:
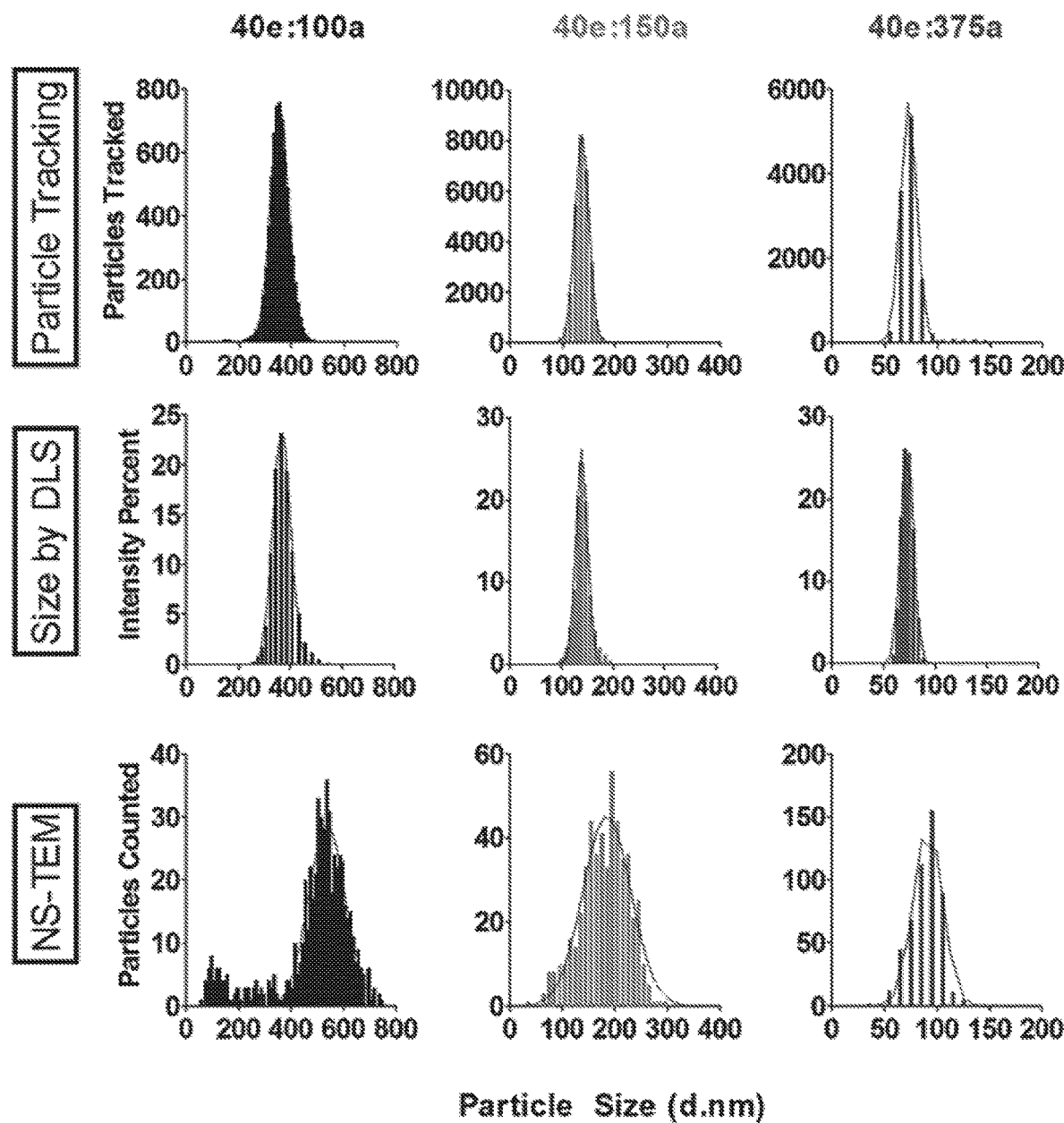
FIG. 20 is a graphical representation of different particle sizing techniques (dynamic light scattering, nanoparticle tracking and particle counting via NS-TEM to assess liposome mean particle size and particle size distribution, according to an example embodiment.
Figure 21:
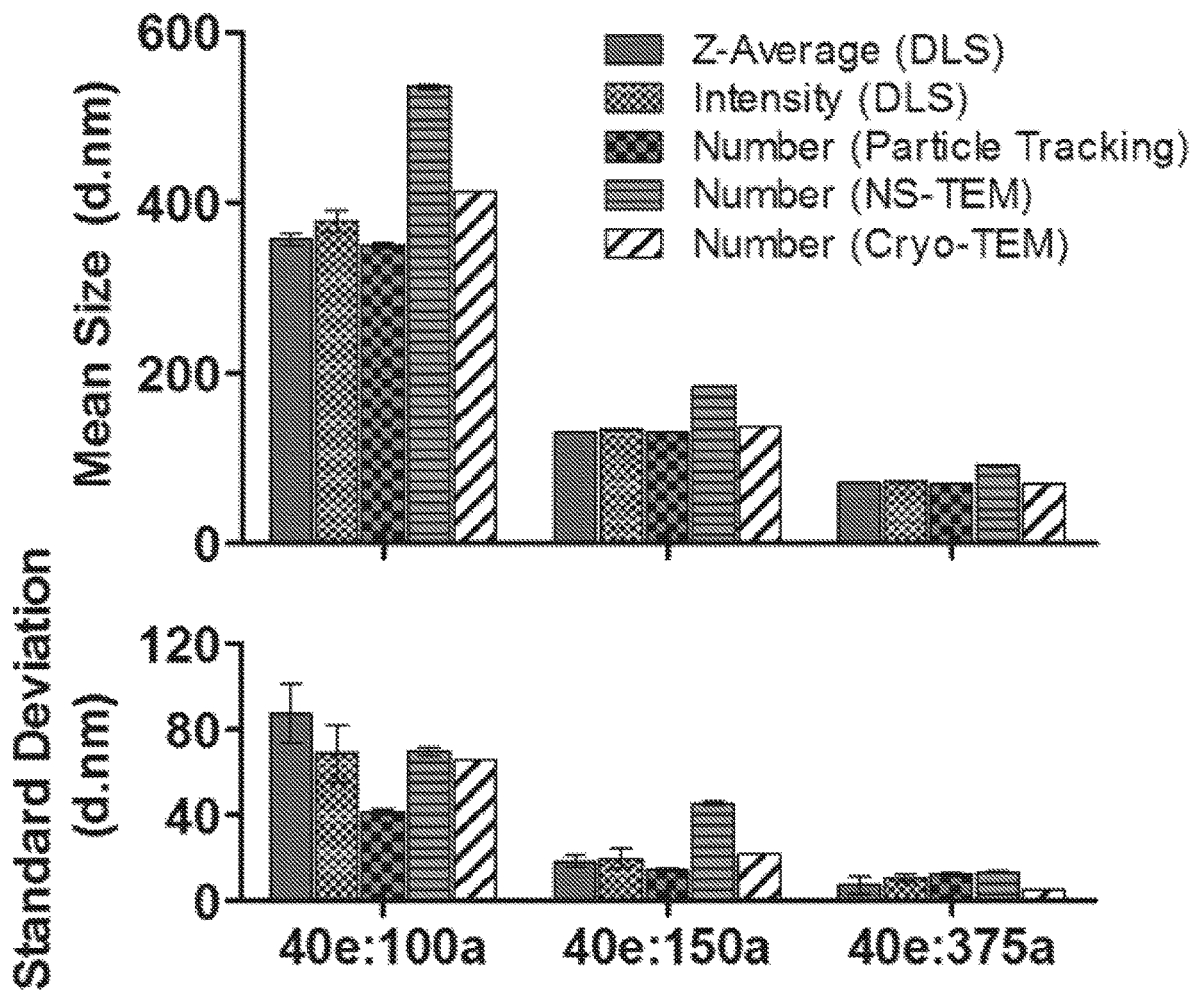
FIG. 21 is a graphical representation of liposome mean particle size and standard deviations for DLS, nanoparticle tracking, NS-TEM and Cryo-TEM, according to an example embodiment.

Comparison of Particle Size and Size Distribution Using Multiple Measurement Techniques To accurately assess the mean particle size and particle size distribution, multiple techniques (i.e. dynamic light scattering, nanoparticle tracking and negative stain TEM) were used. Each of the three techniques can be used to determine the mean particle size and particle size distribution; however, each technique differs fundamentally. Dynamic light scattering is an intensity-based measurement, while nanoparticle tracking and negative stain TEM are number-based. Therefore, it is not desired to compare absolute values from each technique, but instead to compare trends and conclude if monomodal populations of particles are present. Samples were prepared in 10 mM ammonium-acetic acid buffer at pH=5.0 to reduce artifacts in the negative staining procedure. The lipid composition for this study was DMPC:Chol:DPPG (4.5:3.0:0.4 molar ratio) and 15 mM lipid was injected into the aqueous phase. Three samples were prepared at a constant ethanol flow rate (40 mL/min) but at different aqueous phase flow rates (i.e. 100, 150 and 375 mL/min). The three samples were chosen as they were estimated to produce liposomes with a mean particle size around 350, 140 and 70 nm, respectively (FIG. 18). FIG. 20 displays the mean particle size data from the three separate techniques. It is clear that nanoparticle tracking and dynamic light scattering display a monodispersed population. Negative staining produces an overall wider distribution of particles and possibly smaller particles present in the larger-sized liposome sample. However, the negative stain TEM results may not adequately represent the liposome population due to a low number count and multiple artifacts that can occur during sample preparation. FIG. 21 is a plot of the mean particle size and the standard deviation for each sample and technique. It was demonstrated that the mean particle size trend is the same using all three particle sizing techniques, i.e. for an increase in aqueous flow rates (higher $Re_{mixture}$), the particle size decreases. For all three samples and each particle size analysis technique, the standard deviations were 15.8±4.70% of the mean.

Negative Stain TEM Micrographs of Liposomes

Figure 22A:
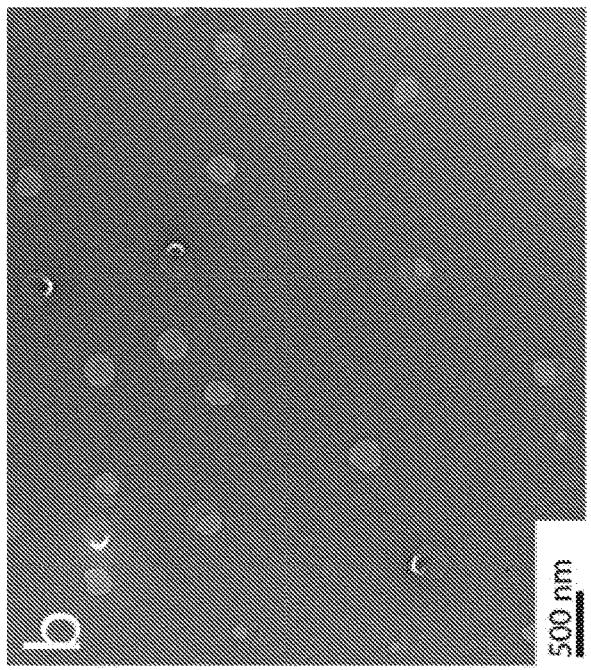
FIGS. 22A-22D are negative stain TEM micrographs of liposomes for three liposome samples produced using different flow conditions, according to example embodiments.
Figure 22B:
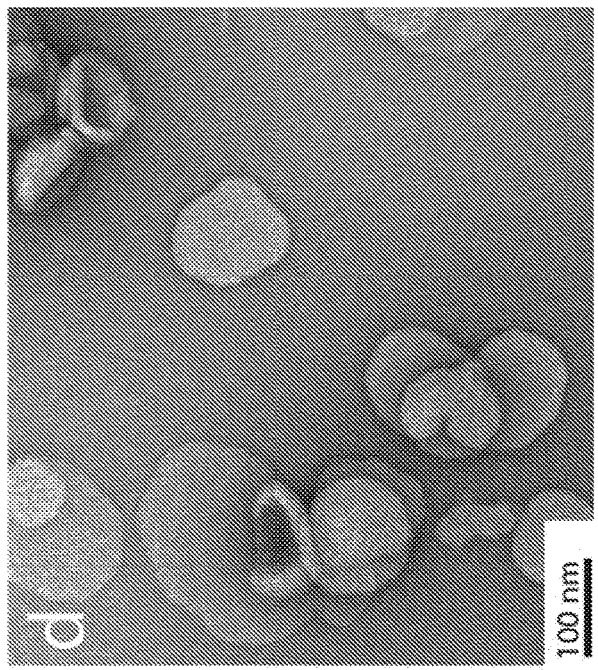
Figure 22C:
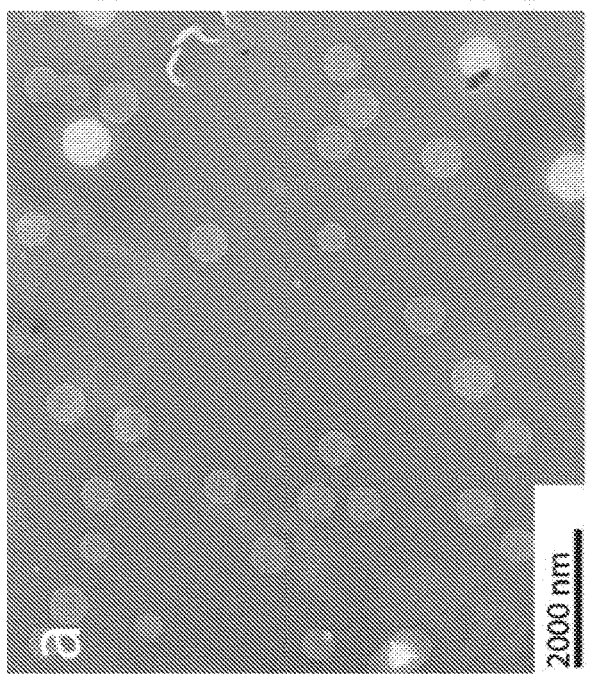
Figure 22D:
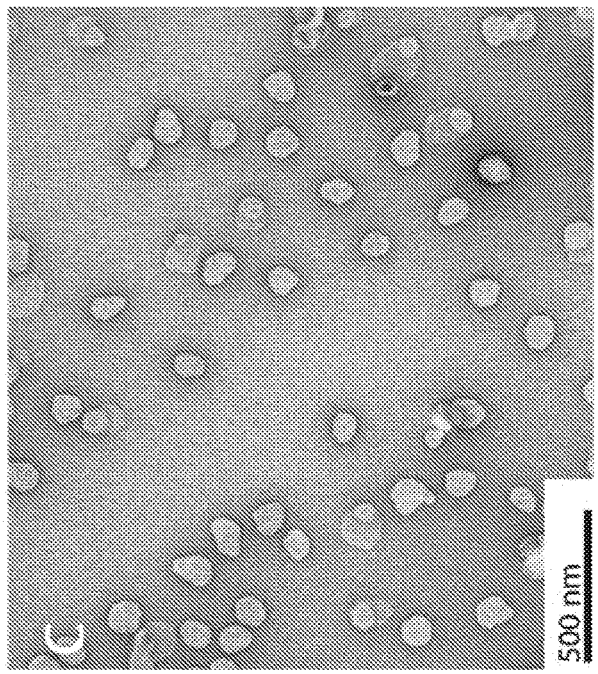

FIGS. 22A-C are micrographs of the three different samples outlined above (FIG. 20) from the particle size technique analysis. The micrographs demonstrate particle size differences between samples. Each sample set appears to be monodispersed. FIG. 22D demonstrates how liposomes are affected by the staining process. It appears that the liposomes are in one of three possible states: (1) "partially-hydrated" liposomes (these liposomes appear to be dehydrated, but partially retain the structure as in the hydrated state); (2) flattened-stacked bilayers; or (3) mixture of a flattened-stacked bilayer and/or single bilayer. The "partially-hydrated" liposomes have an appearance of dehydrated liposomes and have more uniform size, while the "flattened" states vary in size. This apparent size variation (that results from the processing required for this technique) can explain why the mean particle size and size distribution are overall greater from the NS-TEM micrographs compared to the other particle size analysis techniques.

Cryo-TEM Micrographs of Liposomes

Figure 23B:
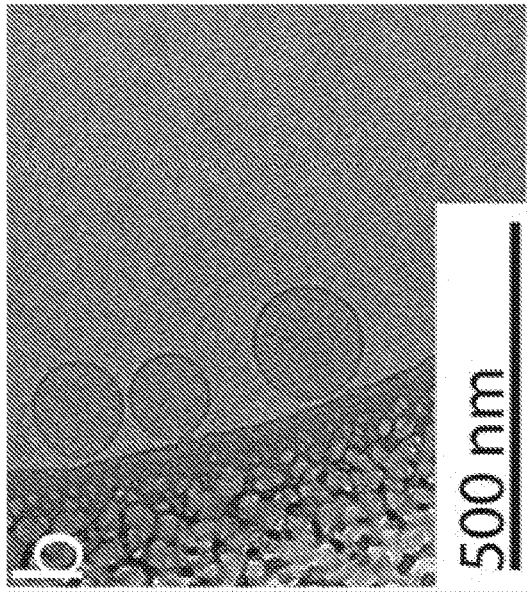
FIGS. 23A-23C are Cryo-TEM micrographs of liposomes for three liposome samples produced using different flow conditions, according to example embodiments.
Figure 23C:
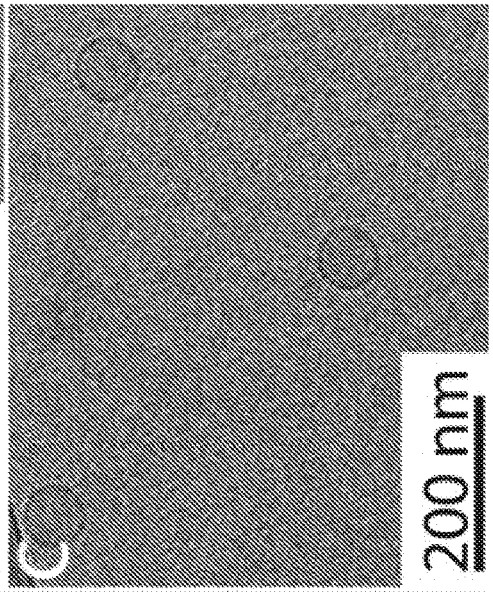
Figure 23A:
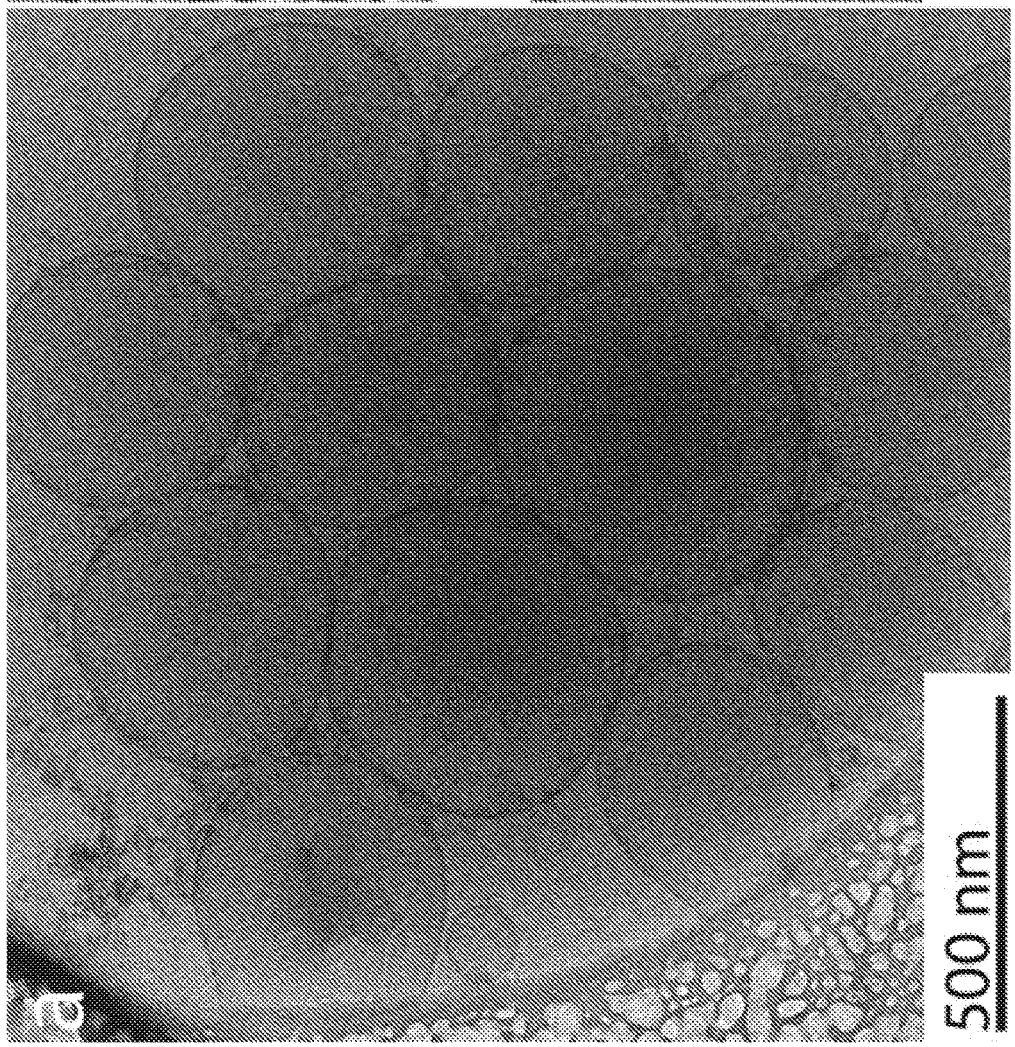
Figure 25:
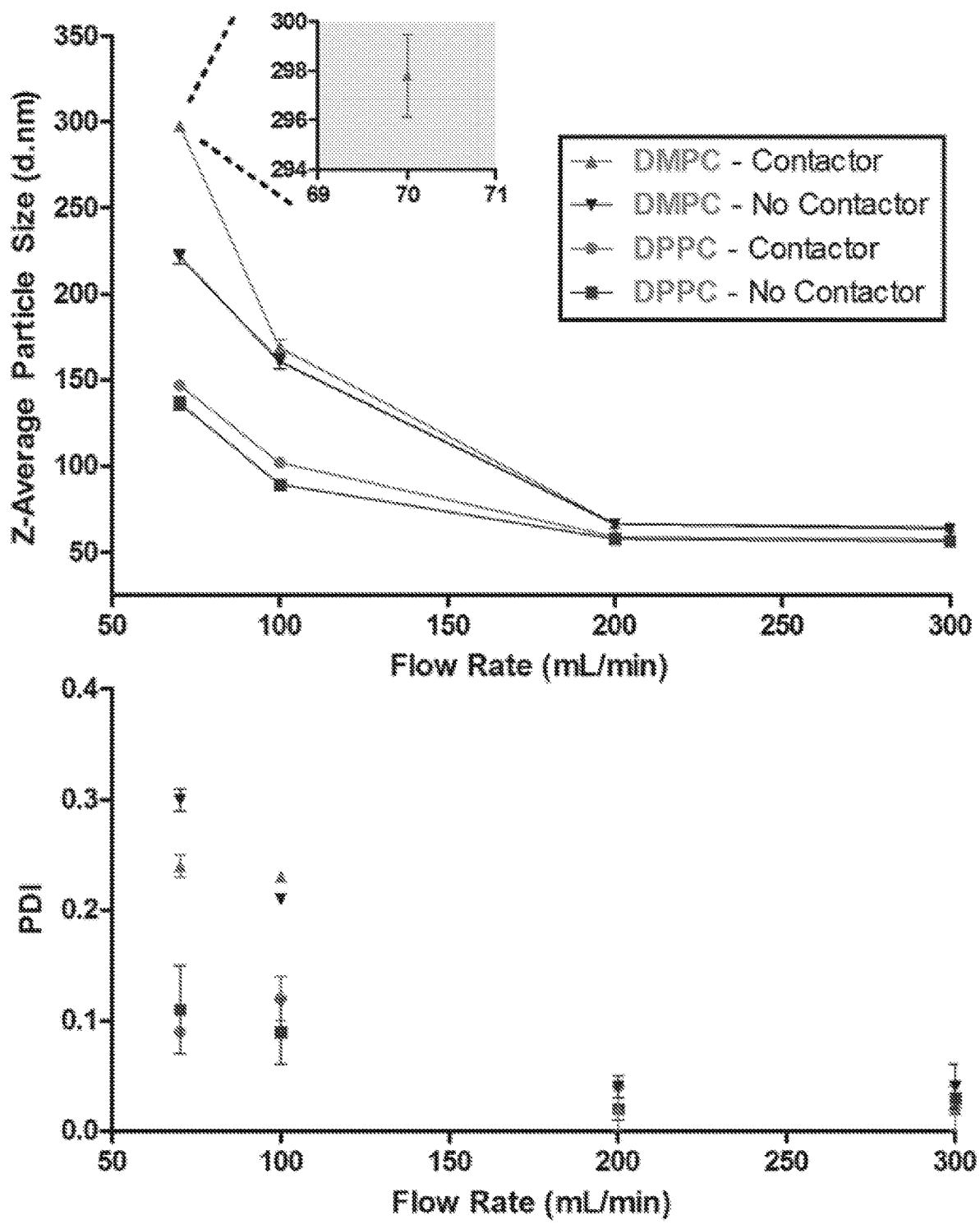
FIG. 25 is a graphical representation of liposome mean particle size and polydispersity index for both lipid:Chol:DPPG (4.5:3:0.4 molar ratio) liposomes, where lipid refers to either DMPC or DPPC, according to an example embodiment.

The micrographs from FIG. 23A-C are of the three different samples outlined above in FIG. 20 and FIG. 22. These micrographs confirm the particle size trend stated previously and that these liposomes are unilamellar. Comparing the visible black band of each liposome, the thickness of the band is very similar for the small to the large liposomes.

Discussion

Liposome Monodispersity Via a Coaxial Turbulent Jet

Flow conditions, characterized by the FVR and the $Re_{mixture}$ lead to either polydispersed or monodispersed liposomes (FIG. 16A). Polydispersed liposomes were formed under two different flow conditions—i.e. an apparent stratified flow (FIG. 16B-1) and a weak jet (FIG. 16B-2). The stratified flow led to stream separation and uncontrolled mixing. The weak jet appeared to develop vortices that led to backflow along the jet—also resulting in uncontrolled mixing.

In order to achieve monodispersed liposomes, the formation of a jet was employed (FIG. 15). Depending on the flow conditions, it appeared that there was the coexistence of a laminar/transitional flow followed by a jet that led to turbulent flow (FIG. 16B-3 and FIG. 16B-4). It does not appear that the aqueous phase significantly dilutes the ethanol phase in this laminar/transitional flow region; otherwise, a color change in the fluorescent marker (Nile Red) would be observed due to the change in fluid polarity. Accordingly, it may be stated that limited mixing occurs throughout the laminar/transition region. For the formation of a jet, it has been shown that the center velocity decreases and the jet boundary spreads radially, resulting in a concentration gradient of the injected phase (in this case, lipid+ethanol). Therefore, the majority of mixing occurs where the center velocity decreases and jet boundary spreads radially. As the spreading of the lipid+ethanol phase establishes a radial concentration gradient, it is proposed here that this promotes the controlled formation of monodispersed liposomes. Moreover, convective inertial forces are dominant compared to viscous forces when Re>>1, which supports the reasoning that increasing Re will correspond to an increase in the extent of mixing, thus forming different sized liposomes.

For the formation of monodispersed liposomes, it is evident that $Re_{mixture}$ is directly related to the liposome particle size. In addition, above a FVR of approximately 7, liposome formation is independent of FVR and dependent only on the $Re_{mixture}$. This observation is made by comparing FIG. 16A with FIG. 16C, where the liposomes formed at the same $Re_{mixture}$ have a similar particle size, regardless of the FVR. This indicates that liposome formation from a turbulent jet may be a predominately a convective process and occurs at the radial spreading in the turbulent region of the jet.

Considering the phospholipid formulation as well as the $Re_{mixture}$ and FVR, the formulations containing DSPC, DPPC and DMPC formed mostly monodispersed liposomes (for an FVR≥7). Some polydispersity was evident at lower aqueous flow rates and may have been due to higher ethanol percentages destabilizing the liposomes. However, the formulation containing DOPC formed only monodispersed liposomes at the lower aqueous flow rates. For DOPC, a higher $Re_{mixture}$ appears to destabilize the formulation, which could be due to the high curvature of the small particles (~25 nm) and/or the low phase transition temperature of DOPC—making the fluid bilayer more susceptible to fusion at ambient temperature conditions.

Liposome Formation Model Using a Coaxial Turbulent Jet

The injection of lipid dissolved in ethanol into an aqueous phase is further complicated by changes in properties such as viscosity, density, molar volume, heat of mixing (exothermic in this case), lipid solubility, and lipid structure (e.g. lipid molecular volume). It does not appear that any property above is solely related to the observed particle size changes of liposomes. By using the $Re_{mixture}$, the following terms are taken into account: viscosity, density and sensible heat gains.

The exact mechanism of how liposomes form is still elusive; however, a detailed model for the liposome formation process is beginning to emerge through experimental findings. Initial work in this field has outlined that bilayered phospholipid fragments (BPF) form and fuse together as the volume percentage of ethanol decreases. For a turbulent jet, a model based on the formation and subsequent fusion of BPF resulting in monodispersed liposomes leads to some doubt. During the centerline velocity dissipation of a jet, multiple vortices form and subsequently shear off. Since this process is turbulent, vortices of different sizes would develop and the mixing in these micro-environments would appear to be heterogeneous. Consequently, BPFs that fused during this process would only form polydispersed particles.

A new model for liposome formation is proposed in FIG. 24. This model is based on the growth of a highly fluid lipid/ethanol aggregate (denoted here as a pro-liposome). Initially, lipid is dissolved in ethanol forming a solution. As outlined above, the ethanol spreads radially at the jet location resulting in a concentration gradient. At this point, water mixes with the ethanol+lipid phase and pro-liposomes begin to grow in size until a critical solubility is reached (~50-60% v/v ethanol). The final liposome size is then dependent on the following factors: (1) ethanol diffusion out of the pro-liposome, (2) pro-liposome fluidity, (3) lipid packing, (4) pro-liposome surface charge and (5) lipid concentration.

Ethanol diffusion out of the pro-liposomes is exemplified by the addition of excess ethanol to the aqueous phase. Ethanol is known to be able to cross the lipid bilayer, i.e. move from the aqueous phase into one bilayer leaflet and cross from one leaflet to the other. In addition, P-NMR studies have confirmed that ethanol causes the liposome bilayer to become less packed. Comparing 10-30% v/v excess ethanol to 0% v/v excess ethanol in the aqueous phase, ethanol diffusion out of the pro-liposome would be slower during the mixing process and consequently the bilayer would have higher permeability due to the larger amount of ethanol. Accordingly, there would be more time and space for lipid molecules to enter the pro-liposome—thus growing in size. Moreover, the addition of 26 wt % glycerin to the aqueous phase did not cause any major change in particle size, which indicates that the increased bulk viscosity is less essential compared to ethanol diffusion out of the pro-liposome and convective forces.

The lipid phase transition is useful in assessing the fluidity of the pro-liposome. The phase transition temperatures of the phospholipids in this study are ranked in the following order: DSPC>DPPC>DMPC>DOPC (highest to lowest). By comparing only the saturated phospholipids, DSPC is the most ordered while DMPC is the most fluid over the temperature range caused by exothermic mixing in these experiments (i.e. 23-32° C.). It appears that liposomes form when lipid molecules are in the fluid/disordered state rather than the gel/ordered state. For example, DPPC:DPPG (7.5: 0.4 molar ratio) formed a viscous, gel-like structure instead of liposomes at a 5 mM lipid injection (data not shown). It should be noted that adding cholesterol increases the fluidity/disorder of the lipid membrane; thus, making it is possible to form liposomes at temperatures below the lipid phase transition temperature of the corresponding pure lipid. A more ordered structure would prevent lipid molecules from entering the pro-liposome—resulting in smaller liposomes. This reasoning explains why liposomes form in the following order of smallest to largest (DSPC<DPPC<DMPC). A more detailed analysis that includes the impact of temperature, cholesterol percentage and charged lipid percentage may be useful to thoroughly explain the above observation.

Changes in lipid packing are exemplified by DOPC, which adds an additional complexity in that this lipid is unsaturated (i.e. it has a double bond in each hydrocarbon tail). The geometric packing parameter of DOPC is =1.08 and, when mixed with other lipids, may support a geometrically smaller sized particle (i.e. as low as 25 nm in diameter). In comparison, DSPC, DPPC, and DMPC lipid molecules have a packing parameter ~1 and are more cylindrical in shape. Thus, these DOPC liposomes can support higher curvature/smaller sized liposomes than DSPC even though the phase transition temperature of DOPC was much lower relative to the experimental conditions. Moreover, the more cylindrical shape of DSPC, DPPC and DMPC may explain why these liposomes appear to plateau at a mean particle size of ~60-70 nm at a high $Re_{mixture}$. This indicates that the overall lipid packing of the lipid mixture is a geometric constraint on the liposome particle size.

In the case of the surface charge, the addition of salt to the aqueous phase (e.g. 0.9 wt % NaCl) would lower the surface charge of the pro-liposome and lessen the electrostatic repulsion between the pro-liposome and the individual lipid molecules. This reduced repulsion would allow more lipid molecules to enter the pro-liposomes, thus increasing the final liposome size.

Lastly, the lipid concentration led to a modest increase in liposome particle size. This increase in size further supports the pro-liposome model as more lipid molecules would be recruited into the pro-liposomes. It should be noted that only 5-30 mM lipid was injected, which is a relatively small amount of lipid compared to the other components in the system. Therefore, increasing the lipid concentration would be expected to increase the number of liposomes instead of proportionally increasing the size of the liposomes. Moreover, too high of an injection lipid concentration may cause other types of structures to form (e.g. stacked bilayers) and increased polydispersity.

Overall, the pro-liposome model appears to provide a clearer explanation on the liposome formation process using a turbulent jet. From the above discussion, $Re_{mixture}$ can be used to predict the liposome particle size for a fixed set of factors (i.e. lipid type, lipid concentration, aqueous phase additives, etc.), but will not predict particle size when changing these factors.

Particle Size Analysis Using Multiple Measurement Techniques

Dynamic light scattering is a suitable technique to determine monodispersity by analyzing multiple parameters. These parameters include the z-average, intensity mean, volume percentage and the PDI. The z-average is calculated from a cumulants analysis (an intensity-weighted fitting algorithm) and the intensity mean is determined directly by an intensity fitting algorithm. When both the z-average and intensity mean values are very similar, it indicates that a single population is present. In addition, a volume percentage of 100% further points to a monodispersed system since transforming the data from intensity to volume shifts the emphasis away from the mean particle size. A volume percentage other than 100% may indicate the presence of additional populations of particles. However, there was an initial uncertainty in relying only on dynamic light scattering without comparing to other techniques, as the light intensity of any larger particles will overshadow the light intensity of smaller particles. This overshadowing may prevent the smaller particles from being detected, even when transforming the raw intensity data to a volume measurement.

Comparing nanoparticle tracking and dynamic light scattering, both techniques appeared to show similar results with respect to mean particle size and size distribution. Since both of these techniques determine the particle size using completely different methods (i.e. individually tracking particles vs. fitting functions), the agreement in mean size and size distribution greatly supports that this liposome processing technique has the ability to controllably produce a large size range of monodispersed liposomes.

The NS-TEM micrographs were originally obtained as a way to characterize the liposomes and possibly make visible smaller particle populations that dynamic light scattering might have failed to detect. After analyzing the TEM images, it was not possible to determine an accurate mean diameter or particle size distribution. One reason is due to the processing conditions apparently causing multiple states of liposomes present (i.e. partially-hydrated to flattened stacked bilayers). A second reason is that what appears to be small particles may actually be fragments of larger particles. These possible fragments may explain why the nanoparticle tracking analysis via Nanosight, which analyzed 30,000-90,000 particles per sample, did not show a wider particle distribution and a possible second population of particles in the 40e:100a sample (FIG. 20).

Lastly, the cryo-TEM micrographs further confirmed the mean particle size trend observed using the three particle size analysis techniques outlined above. The advantage of cryo-TEM over NS-TEM is that the samples were controllably frozen to prevent ice-crystal damage and the liposomes were imaged in a more native state. In addition, these micrographs confirmed that the liposomes are unilamellar.

Conclusion:

A turbulent jet mixer can be used to form unilamellar, monodispersed liposomes with a known particle size. The unilamellar, monodispersed particles have a mean size anywhere from ~25 nm to >465 nm. The liposome mean particle size is highly dependent on the $Re_{mixture}$ and is independent of the flow velocity ratios. The monodispersity and mean particle size trend of the liposomes was analyzed using three fundamentally different particle size analysis techniques. Dynamic light scattering and nanoparticle tracking demonstrated that the liposomes were monodispersed and increased in size with a decrease in $Re_{mixture}$. Lastly, a new model outlining the liposome formation process is explained via a pro-liposome growth model that takes into account aqueous phase additives, types of lipid molecules, and lipid concentration.

Tables:

FIG. 42 illustrates a table showing DOE on lipid concentration vs. particle size—model parameter estimates sorted by statistical significance.

Example 2

Materials and Methods:
Materials 1,2-dimyristoyl-sn-glycero-3-phosphocholine (DMPC); 1,2-dipalmitoyl-sn-glycero-3-phosphocholine (DPPC); 1,2-distearoyl-sn-glycero-3-phosphocholine (DSPC); 1,2-dipalmitoy 1-sn-glycero-3-phospho-(1'-rac-glycerol, sodium salt) (DPPG-Na); and Lipoid S PC-3 (HSPC) were purchased from Lipoid™. Cholesterol (Chol) was purchased from Sigma. Ethanol (200 proof, ACS/USP grade) was purchased from Pharmco-AAPER.

Experimental Methods
Liposome Formation and Dilution

Liposomes were prepared by a modified ethanol injection method. A schematic of this system is demonstrated in FIG. 7. Three separate 316 stainless steel tanks contained the lipid+ethanol solution. These tanks were pressurized (at 20 psi) and the flow rates from these tanks were controlled by analog flow meters (McMillian) and proportioning solenoid valves (Aalborg). The flow meters were factory calibrated for water with less than 1% error full-scale. For the lipid+ethanol flow streams, these flow sensors were re-calibrated for ethanol and had an R-squared value of 0.9989, with a working range from 5-50 mL/min. The three tanks were then connected at a single point using a 4-way connector (Swagelok). A static mixer was implemented to ensure that the lipid+ethanol solutions from the three tanks were adequately mixed prior to reaching the injection port where the ethanol and aqueous phase I streams converged. The aqueous phase I volumetric flow rate was controlled by a gear pump (Micropump®). To form liposomes, the mixed lipid+ethanol solution was then injected into an aqueous phase (aqueous phase I) at various flow rates. The tubing ID of the ethanol phase I was 0.508 mm (1.588 mm OD). The aqueous phase I tubing ID was fixed at 4.572 mm. Flow rates of the lipid+ethanol phase ranged from 5-40 mL/min and those of the aqueous phase I ranged from 70-300 mL/min.

After the liposomes were formed, the liposomes passed through a degassing unit (Liqui-Cel) followed by a second three-way T-port. This three-way T-port has one inlet for the liposomes, a second inlet for aqueous buffer and one outlet. A second gear pump (Micropump®) was used to control the flow of the aqueous phase into this port (aqueous phase II). The aqueous phase II flow rate was adjusted such that mixed aqueous phase would have 5% vol. ethanol. Aqueous phase II flow rates ranged from 690-460 mL/min.

Data Acquisition System and Computer Software

The entire process was controlled by a custom-made program written using National Instruments (NI) Lab-VIEW® software. A data acquisition system (NI PXIe-1078) was combined with multiple NI modules to accommodate various input/output signals (e.g. analog and digital inputs/outputs, counters, circuit switches, etc.). The entire system was automated and only required the user to define the final lipid concentration and molar ratios of lipid. Process variables such as flow rates, pressure, and temperature were monitored and some variables were automatically adjusted using custom computer algorithms. For example, proportional-integral-derivative controls were implemented in the computer program to precisely control the flow rates of both the ethanol and aqueous phases.

Communication to and from the Malvern Zetasizer was accomplished using the Malvern Link II software. Malvern Link II software was setup as an OPC server and NI LabVIEW was setup as an OPC client. The z-average particle size and PDI were recorded in the custom computer program. The custom computer program was able to send measurement instructions to the Malvern Zetasizer.

Experimental Outline for Liposomal Dilution

The impact of diluting liposomes was tested for liposome formulations consisting of lipid:DPPG:Chol at a molar ratio of 4.5:0.4:3, where lipid was either DPPC or DMPC. These lipids were chosen since each lipid was previously investigated and they produced liposomes of different sizes, i.e. up to ~500 nm for DMPC vs. up to 150 nm for DPPC. Two processing setups were investigated for the in-line dilution of liposomes. The first processing setup (setup I) was injecting the formed liposomes directly into the aqueous phase II (without the degassing unit in FIG. 7). The second processing setup (setup II) consisted of incorporating a contactor (degassing unit) at the end of the liposome formation stage prior to the ethanol dilution stage (FIG. 7). For each processing setup, aqueous phase I flow rates ranging from 70 mL/min to 300 mL/min were tested. The aqueous phase used in this experiment was 10 mM phosphate buffer at pH=7.4. Each sample was analyzed for mean particle size and polydispersity index.

Temperature Effects on Liposome Formation and Dilution

For the sample liposomal formulations outlined below, these formulations were tested using the second processing setup over a range of temperatures. A chiller was connected to a custom designed heat sink and the aqueous phase I was chilled in-line to a set temperature (e.g. 8° C.). The flow rate of the aqueous phase I was fixed at 100 mL/min. The temperature at the liposome formation stage was recorded in addition to the temperature of the aqueous phase II. Each sample was analyzed for mean particle size and polydispersity index.

Particle Size Measurements

All particle size measurements were performed with a Malvern Zetasizer Nano S. Both off-line and at-line measurements were completed. Prior to measurements, the liposomes were diluted in-line to 5% vol. ethanol and the viscosity and refractive index were pre-set in the Malvern Zetasizer software. Particle size measurements included the z-average particle size and polydispersity index (PDI). For the off-line measurements, disposable plastic cuvettes were used. The samples were equilibrated at 25° C. prior to each measurement. Each off-line measurement duration was set for 10 runs at 10 seconds each with n=3.

For at-line measurements, a flow cell equilibrated at 25° C. was used. Prior to running at-line measurements, a population of liposomes with a low PDI was analyzed for various measurement conditions (i.e. attenuation, run duration, and count rate). Based on these results, the run duration was fixed (between 6-8 seconds) and the attenuation (and count rate) were adjusted to a satisfactory signal for DLS analysis. Two approaches were taken to transfer sample to the Malvern Zetasizer. The first approach (Continuous Flow Mode) was when the liposomes flowed at a constant flow rate 1-1.5 mL/min through the flow cell while the particle size measurement was taken. The setup for this approach consisted of a miniature solenoid pump (Biochem™) that pumped the sample from the process stream to the Malvern Zetasizer. This pump operates by pumping 70 uL for each actuation and by controlling the actuation frequency, precise flow rates can be maintained.

The second approach (Load/Stop Mode) was based on loading the flow cell followed by stopping the flow prior to the measurement. A Micropump® pump was used to control the flow through the flow cell (20-25 mL/min). The pump operated at the set flow rate just prior to particle size measurements, at which point a custom computer algorithm then stopped the pump to prevent fluid flow during the measurements.

Automatic Particle Size Control

A liposome formulation consisting of HSPC:Chol:DPPG (4.5:3:0.4 molar ratio) was used to form the liposomes. The particle size was automatically controlled via the custom LabVIEW program. Initially, a model was established as a feed forward control using information such as salt concentration and type of lipid to reach a user defined particle size. This feed forward control provided an estimate of the aqueous phase I flow rate (ml/min) required to form liposomes of the user defined particle size. To maintain the particle size, a feedback algorithm was implemented using a proportional-integral-derivative (PID) control with the at-line particle size analysis via the Malvern Zetasizer as the process control input.

Results:

Effect of Degassing Unit Prior to Ethanol Dilution

After the liposomes were formed, the liposomal dispersion was diluted to reach 5% vol. ethanol. The liposomes were diluted using the following two processing setups outline in the methods, namely: (1) setup I: without the degassing unit and (2) setup II: with the degassing unit. For DPPC liposomes, the addition of a degassing unit did not cause any major changes in the mean particle size nor the PDI value over the entire flow rate range. For DMPC liposomes, the degassing unit only appeared to cause changes at the lower aqueous phase I flow rate (i.e. 70 mL/min). At 70 mL/min, the mean particle size was larger and the PDI was lower compared to DMPC liposomes without the degassing unit. These results indicate that a larger dynamic range of particles that are more monodispersed are only obtained when the degassing units is positioned at the end of the liposome formation stage.

Temperature Effects on Liposome Formation and Dilution

Figure 26:
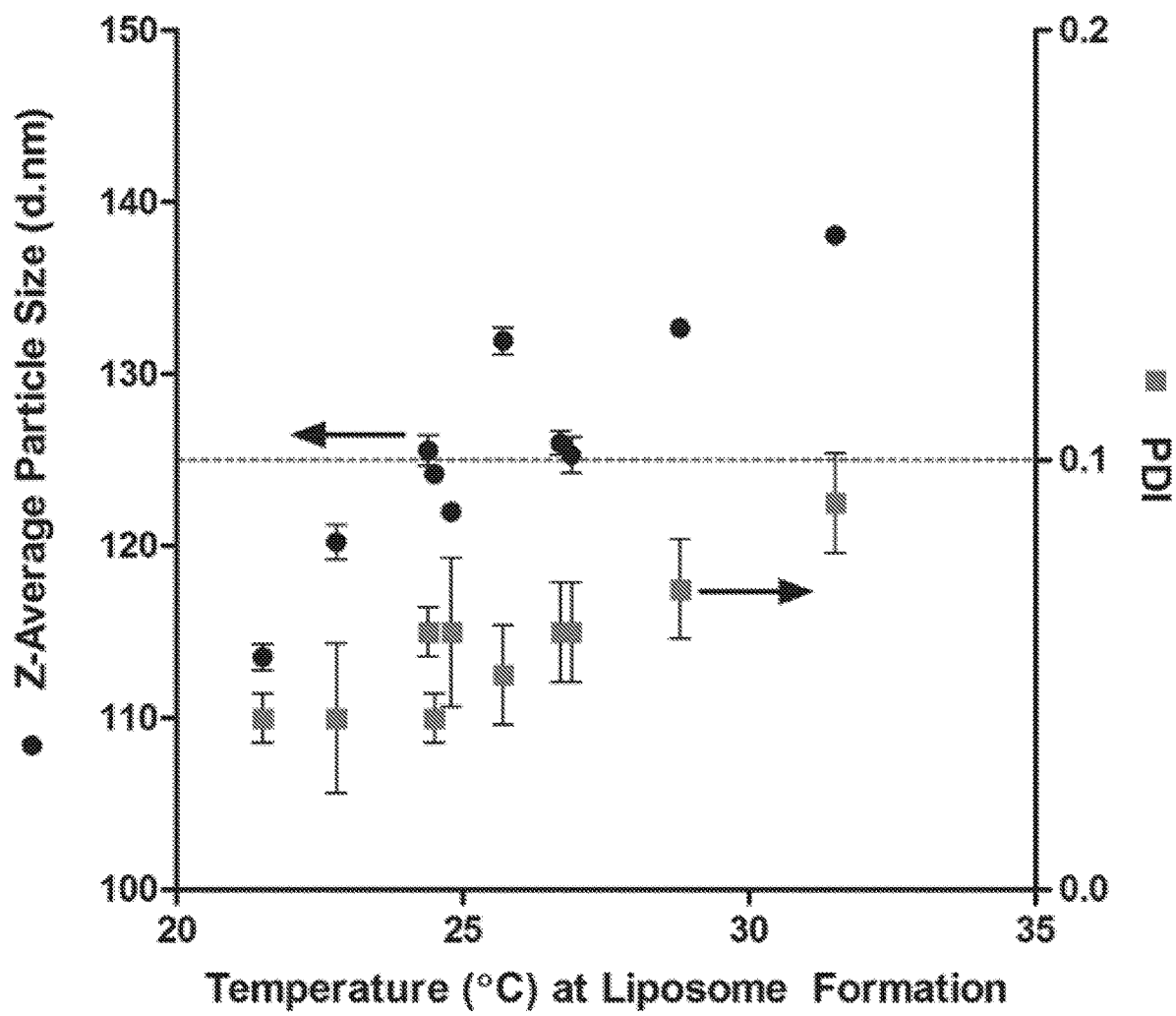
FIG. 26 is a graphical representation of liposome mean particle size and polydispersity index for DPPC:Chol:DPPG (4.5:3:0.4 molar ratio) liposomes, according to an example embodiment.

For these experiments, the temperature of the aqueous phase I and aqueous phase II were the same. When the ethanol+lipid phase was injected into the aqueous phase I, exothermic mixing caused an increase in temperature. The mean particle size and PDI for the DPPC liposomes exhibited an inverse relationship with an increase in temperature at the liposome formation stage (FIG. 26). This observation implies that at higher temperatures, larger liposomes form; however, at higher temperatures, the PDI also tends to increase. For DPPC liposomes, the PDI value did not exceed 0.1 even at the highest temperature, indicating that all of the liposomes, regardless of the temperature at liposome formation, were monodispersed.

Figure 27:
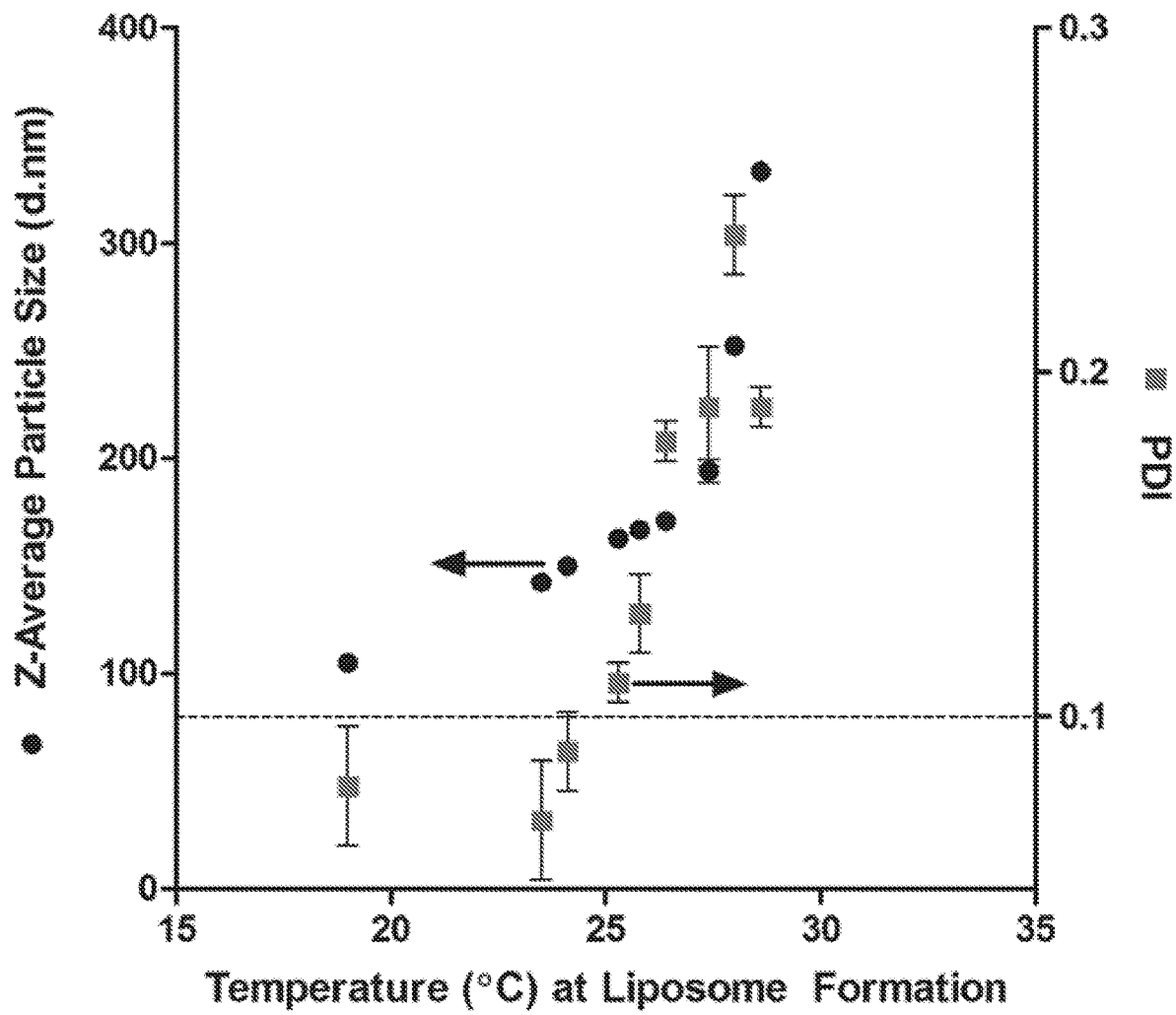
FIG. 27 is a graphical representation of liposome mean particle size and polydispersity index for DMPC:Chol:DPPG (4.5:3:0.4 molar ratio) liposomes, according to an example embodiment.

Sizing data for DMPC liposomes also demonstrated an inverse relationship with an increase in temperature at the liposome formation stage (FIG. 27); however, significant changes in both the PDI and mean particle size occurred around 25° C. As the temperature increased from 24° C., the PDI increased from less than 0.09±0.02 up to 0.24±0.02. This change in PDI indicates that the particle size distribution was wider and/or multiple populations of liposomes were present as the temperature increased. In addition, the mean particle size of the liposomes increased significantly from 26° C. up to 29° C., i.e. from 171.1±1.7 nm to 333.5±4.03 nm.

DLS Measurement Analysis

A previously prepared sample of liposomes was placed in the DLS flow cell and the DLS attenuation and cell position settings were set to automatic. These settings resulted in an optimized attenuation setting of 9 and a cell position of 4.2—with the run duration fixed at 3 runs for 10 seconds each. The particle size information resulted in a z-average of 56.50±0.03 nm, a PDI of 0.05±0.02 and a count rate of 401.4±2.77. Manual measurements were then taken at different attenuations (6, 7, 9 and 11) and run durations (3, 9, or 15 seconds) for a single run only. The plots from FIGS. 28A-C indicate how changing the DLS measurement settings impact the particle size analysis. From FIG. 28A, the z-average for this sample was most accurate at an attenuation of 7-9. At a higher value (i.e. 11), the particle size decreased. The PDI was similar to the control sample at the high attenuation (FIG. 28B). At a low attenuation (i.e. 6), the particle size was incorrect due to a very low count rate (FIG. 28C). In addition, the PDI increased significantly for this measurement. From these results, it is apparent that the count rate should be around or greater than 40 kcps and less than 500-1000 kcps for accurate particle size analysis. Lastly, the run duration did not appear to cause significant changes to the particle size analysis. However, a higher value would increase the number of photons collected and would provide a more accurate particle size analysis.

At-Line Particle Size Analysis—Approach 1: Continuous Flow Mode

Figure 29:
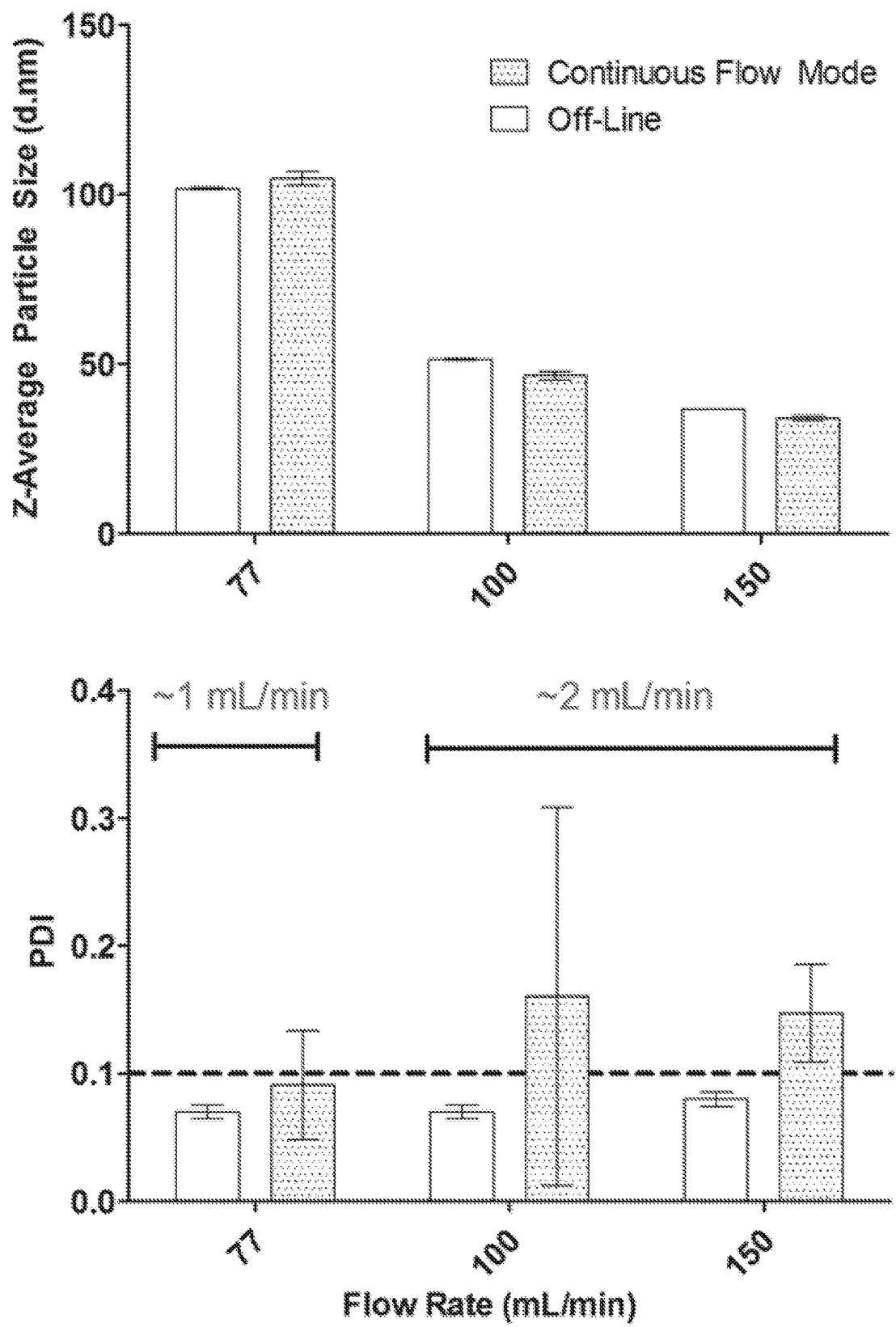
FIG. 29 is a graphical representation of liposome mean particle size and polydispersity index for DPPC:Chol:DPPG (4.5:3:0.4 molar ratio) liposomes, according to an example embodiment.

The at-line particle size analysis via the continuous-flow mode was accomplished using a micro-solenoid pump that pumped the liposome samples at a constant flow rate (referred to as DLS flow rate) through the DLS flow cell during the particle size measurement. An initial study was conducted to determine DLS flow rates that resulted in similar particle size data to that obtained using off-line measurements. Liposomes composed of DPPC:Chol:DPPG (4.5:3:0.4 molar ratio) were formed at three aqueous phase flow rates (i.e. 80, 100 and 150 mL/min). The at-line particle size measurements were compared with the off-line particle size measurements. From FIG. 29, the mean particle size was similar for both the continuous flow mode and the off-line measurements at the three different aqueous phase I flow rates and for DLS flow rates at ~1 and 2 mL/min. To the contrary, the PDI was only similar when the DLS flow rate was around 1 mL/min. At 2 mL/min in the continuous flow mode, the standard deviations and mean PDI were larger when compared to the off-line measurements. Therefore, the subsequent experiments for the continuous flow mode operated with a DLS flow rate around 1 mL/min.

Liposomes were then analyzed over a period of time to investigate how process changes (i.e. flow rate changes) impacted the mean particle size and PDI with respect to both accuracy and measurement lag time. Measurement lag time is the difference in time between a process change to the corresponding particle size data that is recorded in the custom software. This lag time is from the DLS measurement (e.g. run duration and temperature equilibration), delays in software/instrument communication and time required to remove the previous sample in the DLS flow cell. The liposomal samples from FIG. 30 were run at 1 mL/min and showed agreement between some of the continuous particle size data and the off-line data. The mean particle sizes and PDI values for both continuous and off-line measurements were similar except for after the flow rate change. These anomalies may be explained by air bubbles entering the flow cell. In addition, there was a 58 second delay between the process changes to when the corresponding particle size data was recorded in the custom LabVIEW program.

Figure 31:
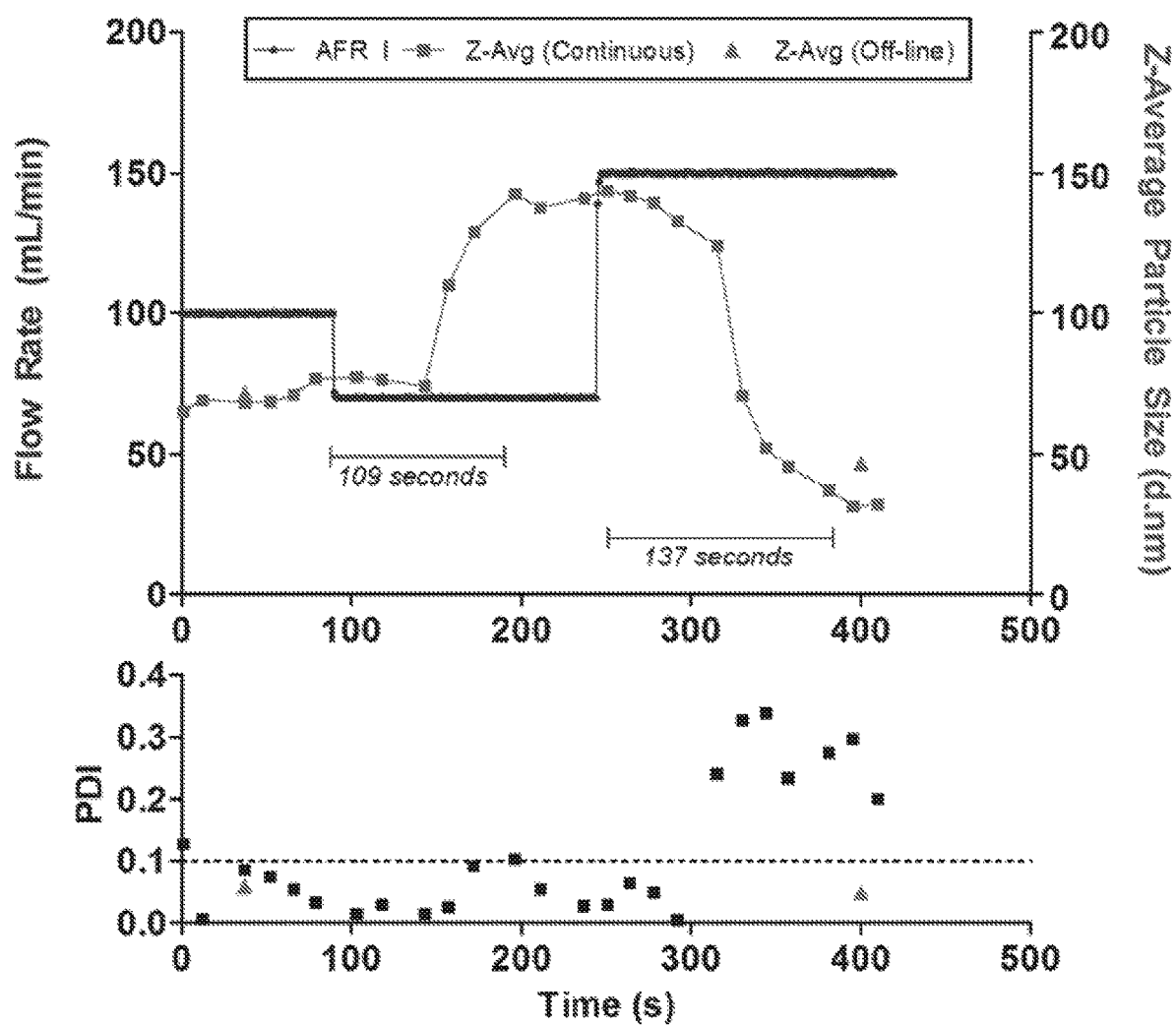
FIG. 31 is a graphical representation of liposome mean particle size and polydispersity index (PDI) for DPPC:Chol:DPPG (4.5:3:0.4 molar ratio) liposomes in 10 mM Hepes buffer, according to an example embodiment.

A second analysis was conducted using for DPPC:Chol:DPPG (4.5:3:0.4 molar ratio) liposomes in 10 mM Hepes buffer (FIG. 31). For this experiment, the liposomes flowed through a degassing unit prior to entering the DLS flow cell. The off-line particle size measurement data at the 100 mL/min aqueous 1 phase overlapped the continuous measurement data. At 150 mL/min, the particles became smaller (i.e. approximately 45 nm) and the particle measurement data for the off-line and continuous measurements did not correspond. The mean particle size was different by 15 nm and the continuous mode PDI ranged from 0.20-0.33, but was 0.05 for the off-line measurement. In addition, the measurement lag time was from 109-137 seconds.

Approach 2: Load/Stop Mode

For this approach, the liposomes were loaded into the flow cell at 20-25 mL/min prior to the DLS measurement. At 1-2 seconds before the DLS measurement, the flow was stopped. After the DLS measurement was completed, the flow began again and this process repeated for the duration of the experiments. The experiments here were designed to accommodate small and large liposomes using the same lipid formulation, i.e. DPPC:Chol:DPPG (4.5:3:0.4 molar ratio).

Figure 32:
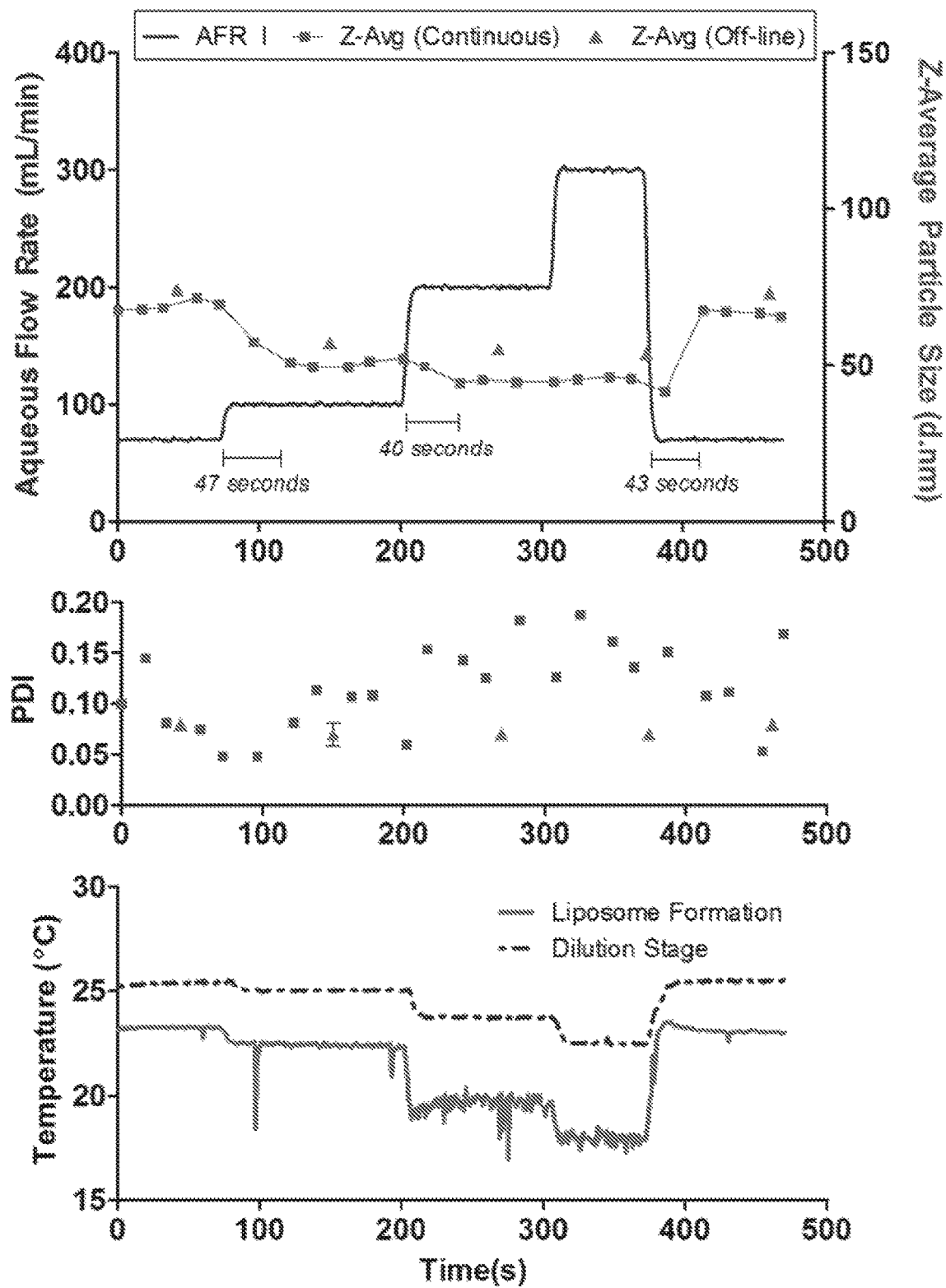
FIG. 32 is a graphical representation of liposome mean particle size and polydispersity index (PDI) for DPPC:Chol:DPPG (4.5:3:0.4 molar ratio) liposomes in 10 mM NaCl, according to an example embodiment.

To achieve different sizes, three different aqueous phases were investigated, i.e. 10 mM NaCl, 75 mM NaCl and 140 mM NaCl. Liposomes prepared in 10 mM NaCl formed liposomes ranging from approximately 70 nm down to 45 nm in diameter (FIG. 32). Slight deviations for the continuous particle size and off-line particle size were observed. The PDI was similar and less than 0.2 in all cases. The measurement lag time appeared to be consistent around 40-47 seconds. Process temperatures at both liposome formation and at the ethanol dilution stage were recorded as both of these temperatures have an impact on the mean particle size and PDI.

Figure 33:
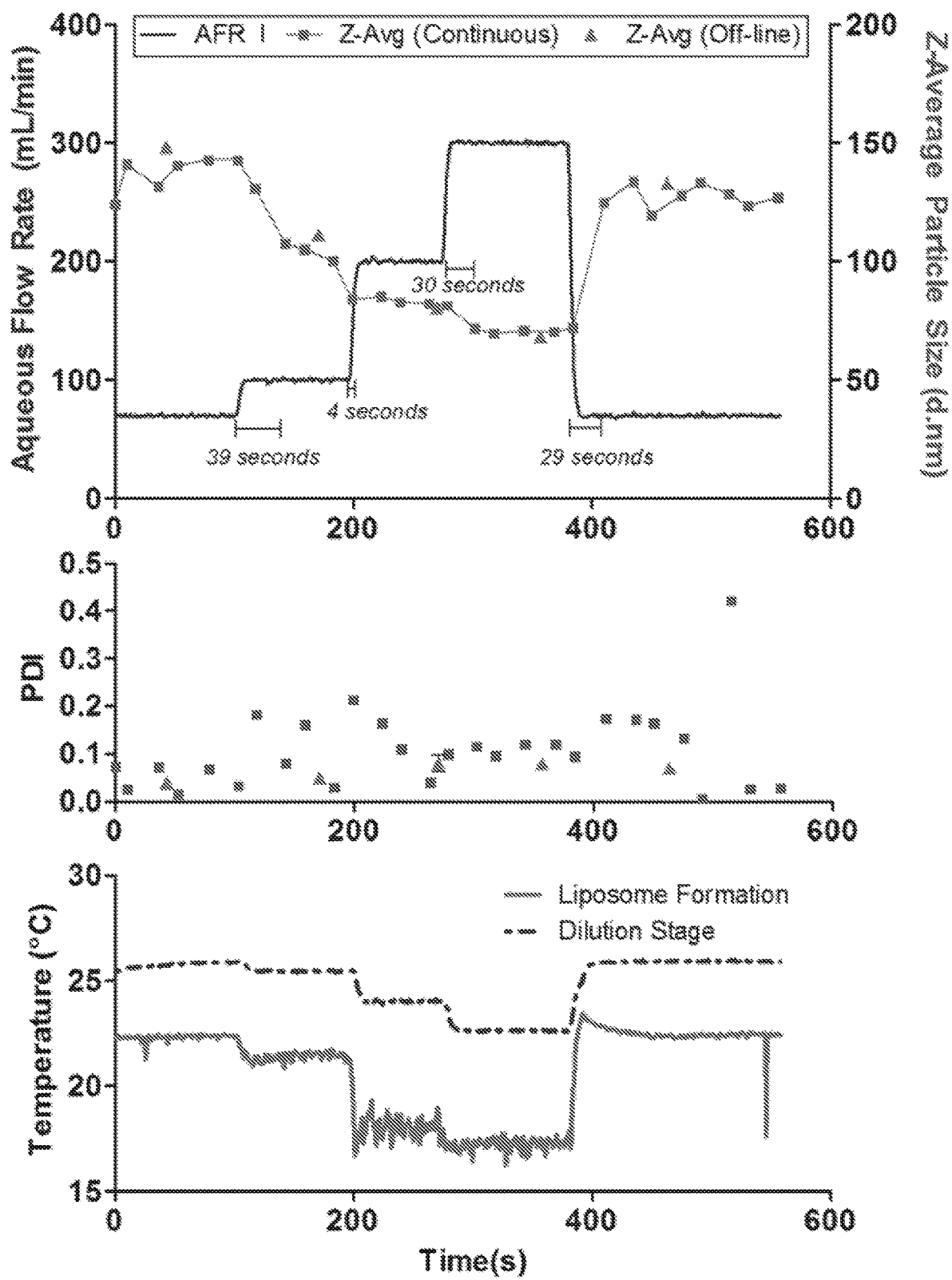
FIG. 33 is a graphical representation of liposome mean particle size and polydispersity index (PDI) for DPPC:Chol:DPPG (4.5:3:0.4 molar ratio) liposomes in 75 mM NaCl, according to an example embodiment.

Liposomes prepared in 75 mM NaCl formed liposomes ranging from approximately 145 nm down to 70 nm in diameter (FIG. 33). The mean particle size for the continuous and the off-line measurements overlapped for the majority of each flow condition. The same observation was true for the PDI values. The measurement lag time appeared to vary from 4-39 seconds; however, the 4 second may have been an anomaly. More accurately, the lag time appears to be constant around 29-39 seconds.

Figure 34:
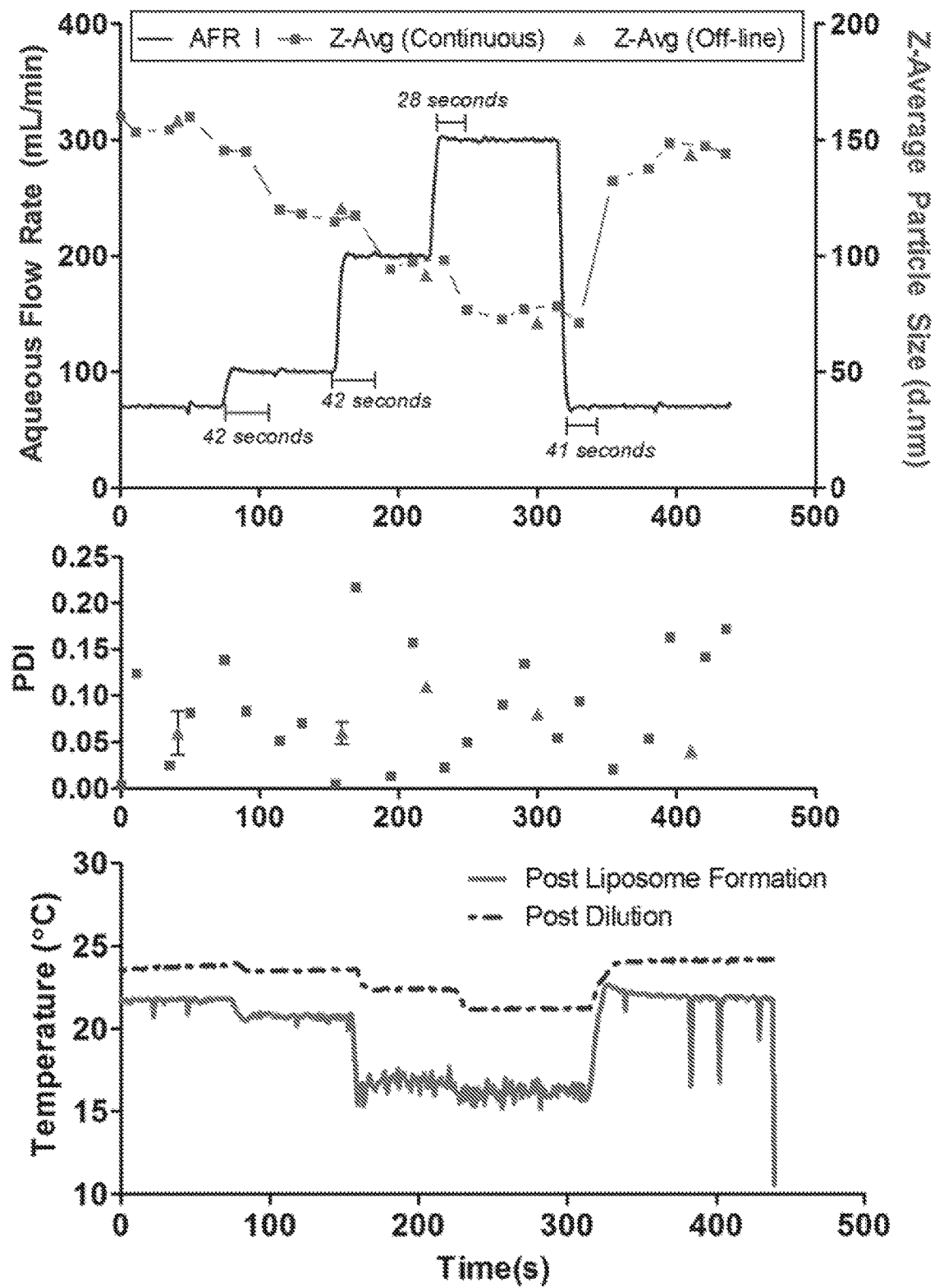
FIG. 34 is a graphical representation of liposome mean particle size and polydispersity index (PDI) for DPPC:Chol:DPPG (4.5:3:0.4 molar ratio) liposomes in 140 mM NaCl, according to an example embodiment.

Liposomes prepared in 140 mM NaCl formed liposomes ranging from approximately 160 nm down to 70 nm in diameter (FIG. 34). The mean particle size for the continuous and the off-line measurements also overlapped for the majority of each flow condition. The same observation was true for the PDI values. The measurement lag time was from 28-42 seconds, consistent with the previous two salt conditions.

Ionic Strength on Liposomal Physical Properties

Figure 35:
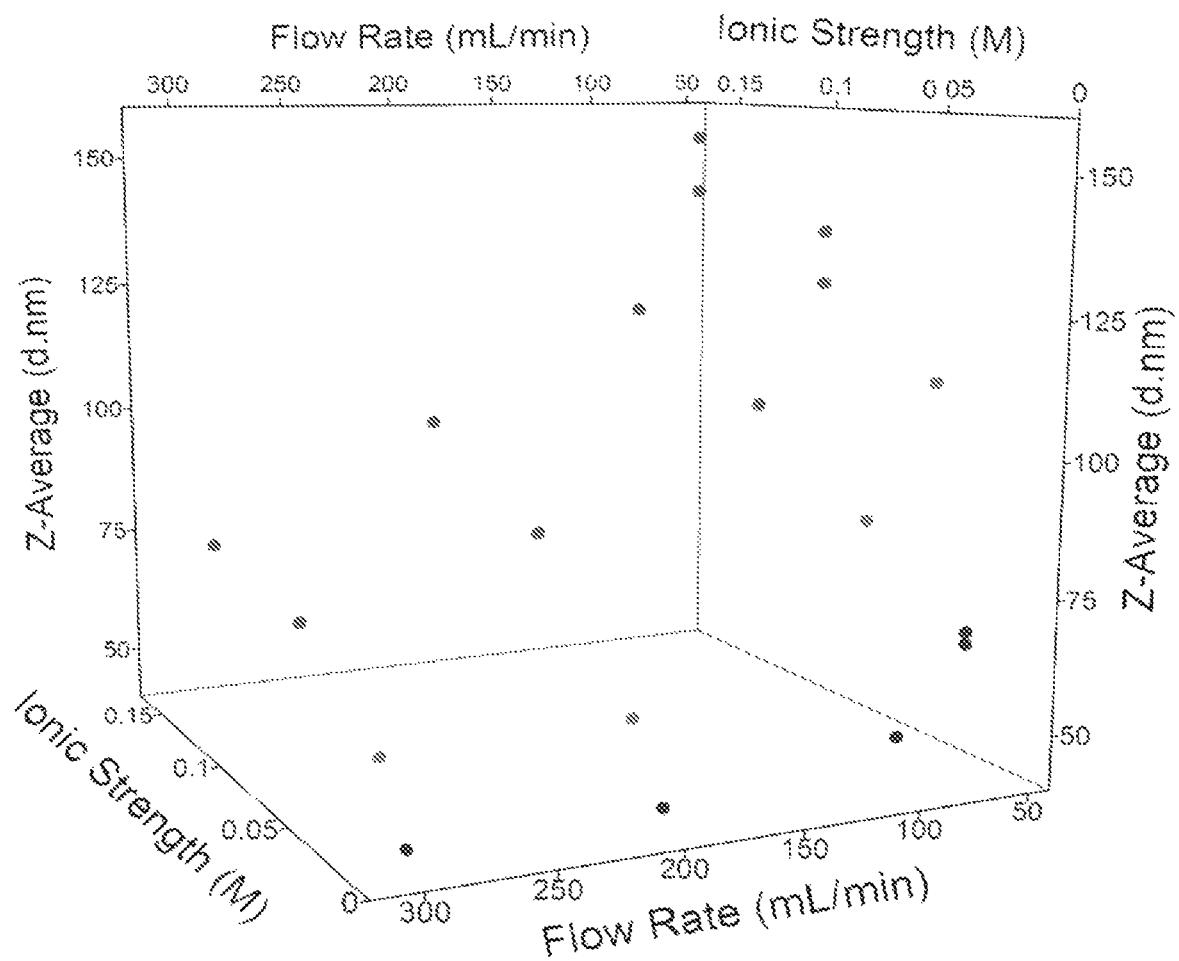
FIG. 35 is a graphical representation of liposome mean particle size (z-average, d.nm) for DPPC:Chol:DPPG (4.5:3:0.4 molar ratio) liposomes in 10-140 mM NaCl and 10 mM PB, according to an example embodiment.

The off-line particle size data from FIGS. 32-34 were replotted vs. flow rate (FIG. 35). It is clear that the mean particle size has a dependence on the amount of NaCl present in the aqueous phase. At low salt concentrations, i.e. 10 mM NaCl and 10 mM PB, pH 7.4, the particles were smaller compared to higher salt concentrations. There was not a large difference between the liposomes prepared in 75 mM NaCl and 140 mM NaCl. Thus, the NaCl concentration appears to have more of an impact on the particle size in between 10 to 75 mM NaCl. The 10 mM phosphate buffer had an ionic strength of 0.025 M, and the liposomes that formed under this condition had a mean particle size that was in between the 10 mM NaCl and 75 mM NaCl.

Figure 36:
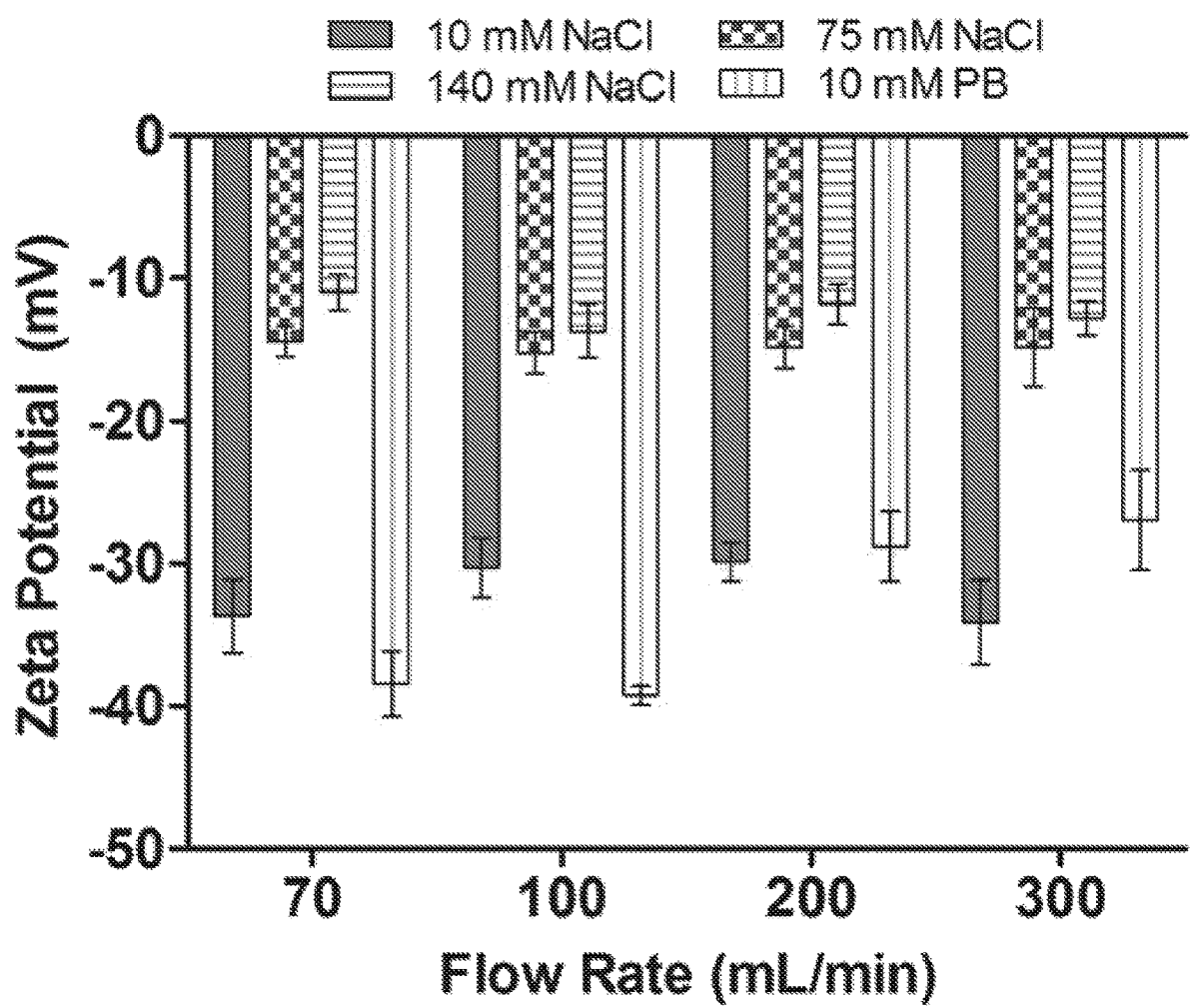
FIG. 36 is a graphical representation of liposome zeta potential for DPPC:Chol:DPPG (4.5:3:0.4 molar ratio) liposomes in 10-140 mM NaCl and 10 mM phosphate buffer, according to an example embodiment.

The zeta-potential was measured for the liposomes prepared in 10-140 mM NaCl and for 10 mM phosphate buffer (FIG. 36). As the NaCl concentration increases, the zeta-potential on the particles decreases. This decrease in zeta-potential corresponds to a decrease in the particle size for the liposomes prepared in NaCl. Liposomes prepared in 10 mM phosphate buffer had a similar zeta-potential to those prepared in 10 mM NaCl; however, the particle size of the 10 mM phosphate buffer liposomes were more similar to liposomes prepared in 75 mM NaCl.

Automatic Particle Size Control

Figure 37:
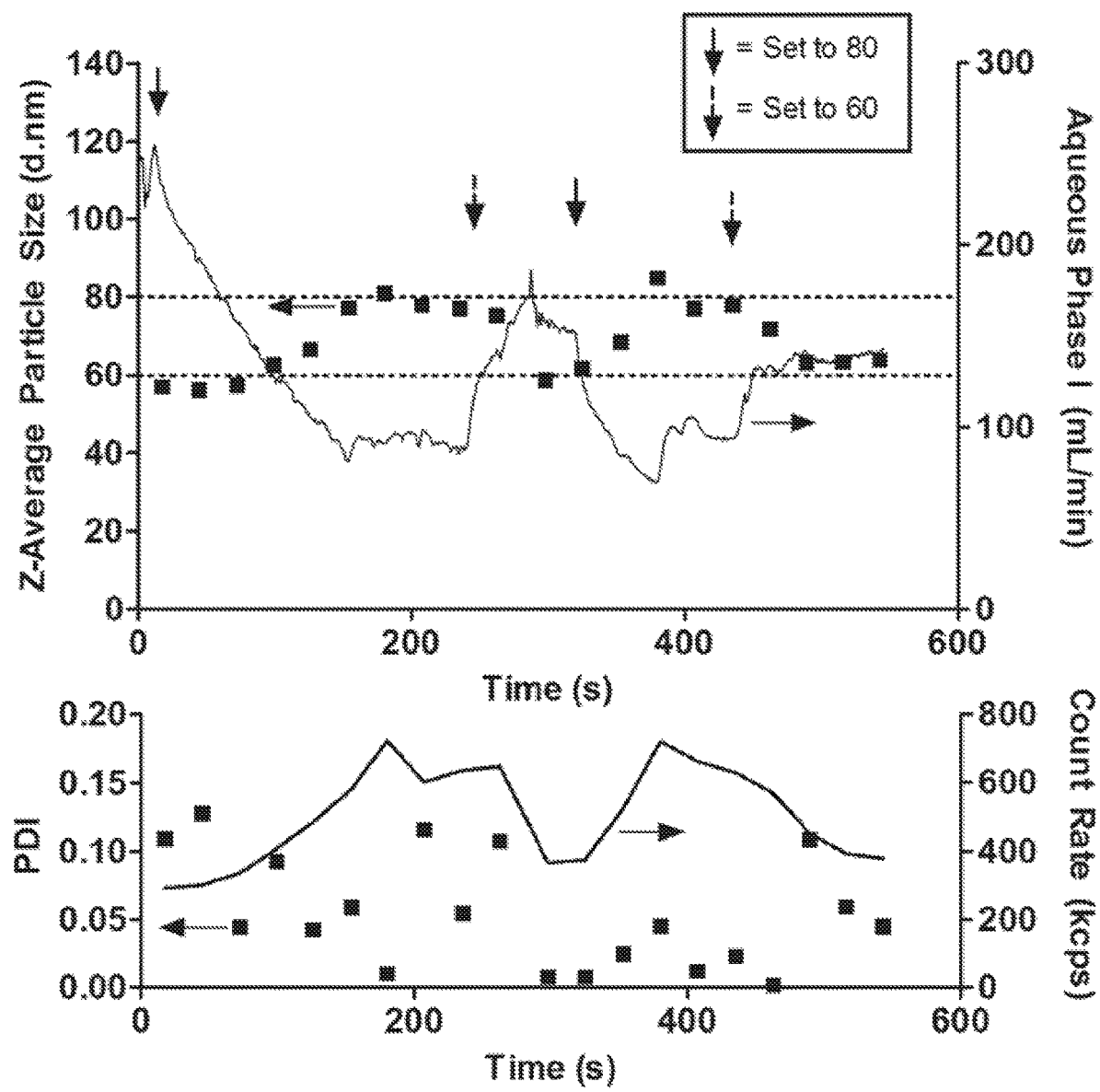
FIG. 37 is a graphical representation of an example of automatic particle size control for HSPC:Chol:DPPG (4.5:3:0.4 molar ratio) liposomes prepared in 10 mM NaCl is shown, according to an example embodiment.

The feedforward model used related the flow rate to the particle size, type of lipid and salt concentration. The feedback control used a PID controller with the following settings: P=1.5, I=0.3 and D=0.001. Two particle size set points were set during this experiment, i.e. 60 nm and 80 nm. Once the set point particle size was reached, the user adjusted the particle size set point to the other set point (FIG. 37). Initially, the feedforward algorithm was able to accurately predict the particle size. After this initial prediction, the feedback algorithm took over to maintain the particle size at the set point. From FIG. 37, it was demonstrated that the feedback control satisfactorily maintained the mean particle size and was able to automatically adjust the flow rates to achieve the set point particle size (i.e. from 60 nm to 80 nm or vice versa). The PDI remained around 0.1 or less during the entire experiment. The DLS count rate fluctuated based on the flow rate conditions, but was within a range that was previously determined to provide satisfactory particle size analysis.

Discussion

In-Line Liposomal Dilution

The first part of this work outlined the importance of degassing the liposomes at the end of the liposome formation stage prior to the ethanol dilution stage. As mentioned, the mixing of ethanol with an aqueous phase is exothermic and leads to sensible heat changes. These heat changes caused dissolved gas to leave the solution, forming bubbles/an air-water interface. For DPPC liposomes, the presence of bubbles did not appear to affect the liposomal particle size distributions. For DMPC liposomes, the particle size distribution was affected at the lower aqueous phase I flow rates, but not at the higher flow rates. Moreover, it was observed that at the lower aqueous phase I flow rates (i.e. 70 mL/min), foam was visible for the DMPC liposomes, but not for the DPPC liposomes. This foaming may be due to a reduction in surface tension as temperature increased—subsequently causing an increase in the mobility of the lipid molecules. This analysis was further corroborated by FIG. 26 and FIG. 27. In these Figures, a change in temperature caused changes in liposomal mean particle size; although, to a greater extent for DMPC liposomes than for DPPC liposomes. In addition, DMPC liposomes exhibited an increased particle size distribution (higher PDI) as temperatures exceeded 24° C. and a significant change in mean particle size as temperatures exceeded 26° C. These events can be explained since the transition temperature for the DMPC phospholipid is around 24° C., which would cause this lipid to experience a more fluid-like behavior near and/or above this temperature. This increased lipid mobility resulted in the formation of larger liposomes, as well as increased foaming. For the DPPC phospholipid, the phase transition temperature is closer to 41° C., which explained why DPPC liposomes did not exhibit larger particle size changes compared to DMPC liposomes over the temperatures investigated.

When foam formed at the liposome formation stage and passed into the ethanol dilution stage (aqueous phase II), this dilution stage became a second stage of mixing, which caused the foam to mix back into the aqueous phase and formed a second population of liposomes. The liposomes formed at the dilution stage would then depend on the mixing at the dilution stage, i.e. the Reynolds number and temperature. Since the flow rates ranged from 460-660 mL/min, the Reynolds number at this stage would be >1000 and supported the formation of smaller liposomes. Therefore, with the addition of foam, a larger particle size distribution existed because essentially two populations of particles formed, one at the liposome formation stage and one at the ethanol dilution stage. By removing the foam after liposome formation, the tendency to form a second population of particles was reduced.

As previously explained, the Reynolds number may be used as a predictive measure of particle size; however, it is only suitable with fixed conditions such as lipid concentration, types of salts, salt concentrations, etc. A lower Reynolds number supports larger liposomes while a higher Reynolds number supports smaller liposomes. By lowering the temperature at the liposome formation stage, this would cause the Reynolds number to decrease, and the liposome particle size to decreases. Therefore, the Reynolds number alone is not a satisfactory measure for the liposome formation process. Instead, a more a thorough model that takes into account factors such as the Reynolds number, temperature, lipid-phase transition temperature, lipid hydrocarbon saturation and buffer/salt composition may be beneficial.

Variables that Influence Particle Size Measurements

There are a number of variables that influence accurate particle size measurement of liposomes for at-line measurements. These variables can be divided into processing variables and DLS measurement variables (FIG. 43). For processing variables, the first is the total dead volume, i.e. the volume of the tubing from the process stream to the flow cell plus the volume of the flow cell. This volume is important since this is the volume that may be replaced after each measurement; otherwise, liposomes that were formed at earlier time points may be mixed with liposomes formed at later time points. Large total dead volumes will incur a large time shift with respect to processing conditions.

A second processing variable is the process stream to flow cell velocity ratio. This ratio is the velocity of the liquid in the process stream divided by the velocity of the liquid flowing to the flow cell. In order to achieve a small time shift, this value may be >>1. This variable is linked with the total dead volume since higher ratios cannot be achieved with large dead volumes, especially at flow rates around 1-1.5 mL/min. For example, the DLS flow cell volume used in these experiments is 100 µL and the total volume including the pump and tubing was approximately 220 µL. Moreover, if DLS measurements were taken every 15 seconds, then 250 µL of sample would pass through during this time. Ideally, since the flow cell has a larger volume than the tubing, it may require more volume to remove the entire previous sample (i.e. 2-3× the total dead volume) and longer delay times in between measurements would be required.

A third processing variable is whether laminar flow occurs. This variable is only important for the constant flow mode. For this variable, small inner diameter tubing (e.g. 0.01") may cause turbulence and affect the Brownian motion of the particles, thus resulting in incorrect particle size measurements. To reduce these effects, larger inner diameter tubing should be used; however, larger inner diameter tubing will increase the total dead volume.

DLS measurement variables include settings such as measurement duration, number of runs and attenuation factor. The measurement duration for each DLS run can be set in the Zetasizer software. For off-line DLS measurements, each measurement consisted of approximately 10-15 runs and each run lasted 10 seconds. The DLS data from each run was then combined to provide a single DLS result. Good quality DLS data is when the total photon count, i.e. the total number of photons acquired after all of the measurements, is greater than 10,000. Additionally, the mean count rate measured in kilo counts per second (kcps) should be greater than 20 kcps and less than 1000 kcps. For lower photon counts, the data may not result in an accurate particle size analysis. For the at-line measurements, only a single run of six second duration was used for the DLS measurements, which would result in a low photon count. However, from FIGS. 30-34, the 6 second duration was adequate for determining the z-average particle size and in most cases, the PDI was similar for both off-line and at-line measurements. Shorter measurement durations (e.g. 3 seconds) may have also provided satisfactory results, but would lead to a lower photon count. Therefore, the at-line measurement experiments used a longer measurement duration (i.e. 6 seconds) to achieve more consistent and higher quality data.

The attenuation factor is another important variable. A low attenuation factor refers to when a lesser amount of light passes through the sample and a high attenuation factor is when a greater amount of light passes through the sample (for a Malvern Zetasizer, the attenuation range is from 0-11, respectively). Changing the attenuation factor will cause the photon count rate to increase or decrease; however, very high count rates will no longer provide accurate data since the DLS detector has a maximum count rate where the response remains linear. For the off-line measurements, the count rate was set to "automatic" in the Zetasizer software. For the at-line measurements, the count rate was kept between 150-400 kcps by programmatically adjusting the attenuation factor depending on the particle size of the liposomes being tested. The advantage of a user-defined attenuation is the reduced overall time per measurement. The disadvantage is that the user-define attenuation factor may not allow for a sufficiently high photon count during measurement—resulting in lower quality data.

Figure 30:
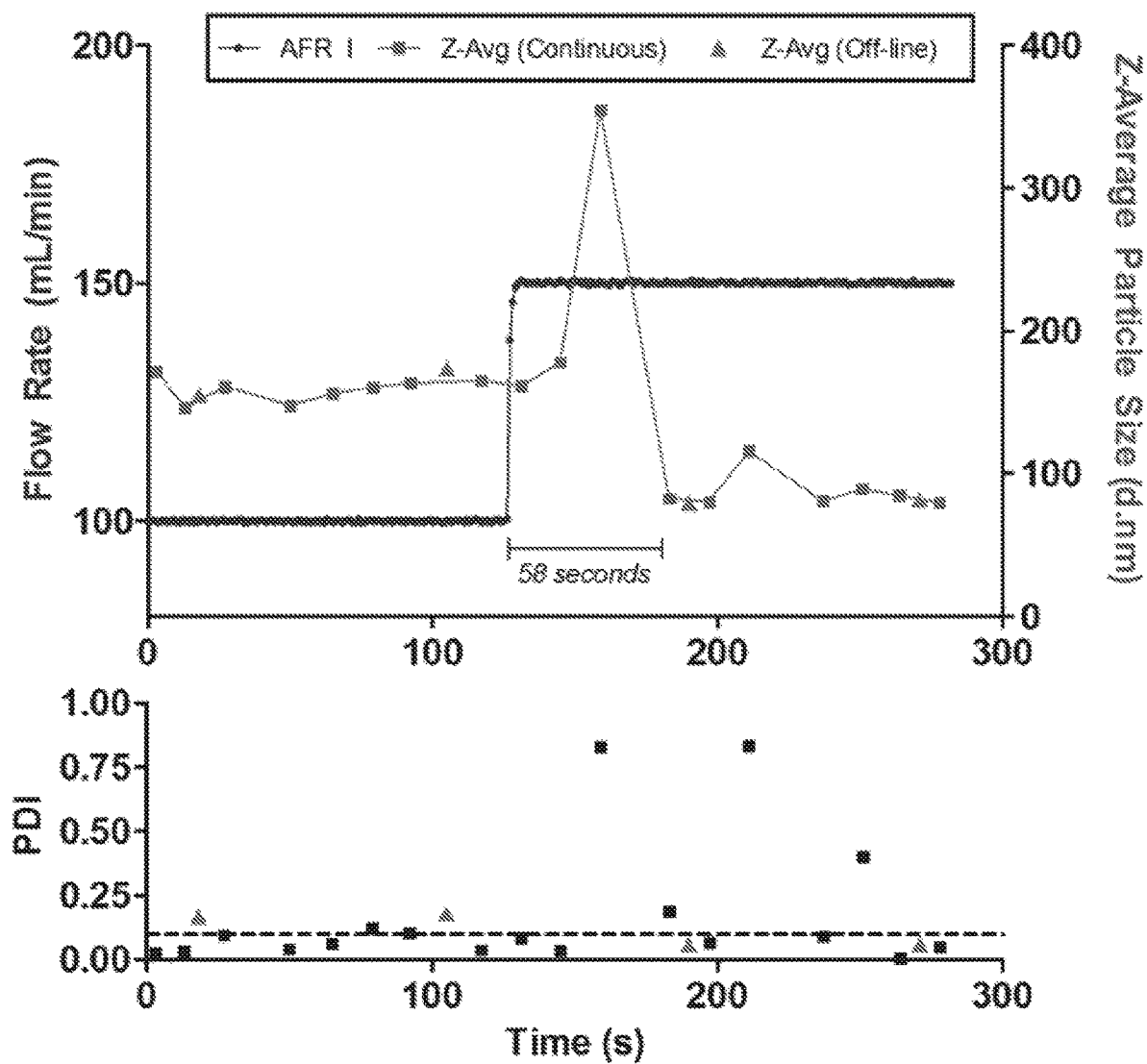
FIG. 30 is a graphical representation of liposome mean particle size and polydispersity index (PDI) for DMPC:Chol:DPPG (4.5:3:0.4 molar ratio) liposomes in 10 mM Phosphate Buffer, according to an example embodiment.

A fourth measurement variable is the presence of air bubbles in the sample. Air bubbles will affect the overall quality of the results since the air bubbles also scatter light. One way to circumvent this issue is to use a degassing unit between where the sample is taken and the DLS flow cell. The disadvantage of using a degassing unit is that the volume of the degassing unit adds to the total dead volume, resulting in longer measurement delays (FIG. 30).

At-Line Particle Size Measurements Comparisons

By comparing the Continuous Flow mode vs. the Load/Stop Mode, the Load/Stop mode appeared to be more accurate and had a more consistent measurement time-delay. When using the Load/Stop mode, the entire sample was removed from the DLS flow cell since the flow rates were around 20-25 mL/min vs. 1-1.5 mL/min for the Continuous Flow mode. In addition, a larger inner diameter tubing was used for the Load/Stop mode and this may have reduced air bubble formation, resulting in fewer artifacts present with the DLS data. One disadvantage of the Load/Stop approach is the rapid loading of the flow cell, which does not allow for temperature equilibration. In this case, the sample temperature may be different than the temperature set in the DLS software, which could explain why the mean particle size, especially for smaller liposomes, was lower when compared to the off-line DLS measurement (FIG. 31). This deviation was only observed for small liposomes (i.e. <50 nm).

Ionic Strength on Liposome Formation

The ionic strength of the aqueous phase significantly affected the liposome mean particle size. From FIG. 35, 10 mM NaCl formed 70 nm liposomes and 140 mM NaCl formed around 160 nm liposomes at the same flow rate (i.e. 70 mL/min). The portion of the phospholipid molecule that is in contact with the aqueous phase is the phosphate head group. Accordingly, the head group may be changing in size (e.g. mean molecular area) and would influence lipid packing. Moreover, by comparing liposomes prepared in 10 mM NaCl to 10 mM phosphate buffer (at pH 7.4), the liposomes prepared in 10 mM NaCl were smaller in diameter. When taking into account the ionic strength, the 10 mM phosphate buffer had an ionic strength greater than 10 mM NaCl but less than 75 mM NaCl. Therefore, an increase in ionic strength caused an increase in liposomal mean particle size.

The ionic strength affects the electrostatic or charge repulsion of neighboring phospholipid molecules (FIG. 35). At a low ionic strength (e.g. 10 mM NaCl), the repulsion would be greater than at 140 mM NaCl since a high salt concentration would lower the overall zeta-potential of the particles (FIG. 36). This is explained by the Gouy-Chapman-Stern theory, which describes that increasing salt concentrations decrease the distance from the charged surface to the plane of shear. When increased amounts of charged species (e.g. $Na^+$) associate with negatively charged phospholipid membranes, the magnitude of the zeta-potential is reduced. According to a previously described liposome formation model, a lower zeta-potential may allow more phospholipids to enter the pro-liposomes and hence result in the formation of larger liposomes.

A second explanation for the increase in size with increase in NaCl concentration is related to local heat effects as the liposomes are initially forming. The excess enthalpy of mixing for the ternary mixture of ethanol, water and NaCl becomes more positive as the salt concentration increases. Reduced enthalpy of mixing indicates more bond breaking events are occurring compared to low salt conditions, i.e. less water-ethanol hydrogen bond formation. This event may suggest that more ethanol is interacting with the lipid molecules during the initial mixing stage, thus promoting larger lipid aggregates to form prior to liposomes formation. However, either explanation, i.e. electrostatic or changes in enthalpy of mixing would be difficult to measure directly since liposome formation is taking place at the molecular level and under turbulent flow conditions. A future study on changing the phospholipid molar ratio of the charged phospholipid may be a suitable alternative to exploring the effects of charge repulsion on the liposome formation process.

Automatic Particle Size Control

In the continuous manufacturing of liposomes, process changes such as pressure or temperature fluctuations will cause changes in the liposomal particle size during the liposome formation process. Using feedforward control to initially predict the process conditions (i.e. aqueous phase I flow rate) and a feedback control to maintain the particle size was demonstrated. By implementing these control strategies, liposomal quality attributes (i.e. mean particle size and particle size distribution) could be maintained, which supported an overall higher quality formulation.

Conclusions:

In-line dilution of liposomes to reduce the ethanol concentration was implemented in this continuous process to form liposomes. Incorporating the in-line dilution stage post the liposome formation process may cause changes to the liposomal particle size distribution—depending on the liposomal formulation. Therefore, it was determined to be useful to include a degassing unit post liposome formation and prior to the in-line dilution stage. At-line particle size analysis was implemented into the continuous processing of liposomes. To reduce time delays between process changes (i.e. flow rates) and the particle size measurement data, it was determined that the Load/Stop mode provided more consistent results when compared with the Continuous flow mode. In addition, the ionic strength of the aqueous phase significantly impacted the mean particle size of the liposomes, i.e. an increase in ionic strength favored the formation of larger liposomes. Lastly, automatic particle size analysis was implemented using both a feedforward and a feedback control, which resulted in precise control and maintenance of the liposomal particle size and polydispersity index.

Tables:

FIG. 43 illustrates a table showing variables that influence continuous particle size measurements.

Example 3

Materials and Methods:
Materials
1,2-dipalmitoyl-sn-glycero-3-phosphocholine (DPPC), 1,2-dipalmitoyl-sn-glycero-3-phospho-(1'-rac-glycerol) (sodium salt) (DPPG-Na) and Lipoid S PC-3 (HSPC) were purchased from Lipoid™. Cholesterol (Chol) was purchased from Sigma. Ethanol (200 proof, ACS/USP grade) was purchased from Pharmco-AAPER.

Experimental Methods
Liposome Formation and Dilution

Liposomes were prepared by a modified ethanol injection method. A schematic of this system is depicted in FIG. 7. Three separate 316 stainless steel tanks contained the lipid+ethanol solution. These tanks were pressurized (at 20 psi) and the flow rates from these tanks were controlled using analog flow meters (McMillian) and proportioning solenoid valves (Aalborg). The flow meters were factory calibrated for water with less than 1% error full-scale. For the lipid+ethanol flow streams, these flow sensors were re-calibrated for ethanol and had an R-squared value of 0.9989, with a working range from 5-50 mL/min. The three tanks were then connected at a single point using a 4-way connector (Swagelok). A static mixer was implemented to ensure that the lipid+ethanol solutions from the three tanks were adequately mixed prior to reaching the injection port where the ethanol and aqueous phase 1 streams converged. The aqueous phase I volumetric flow rate was controlled by a gear pump (Micropump®). To form liposomes, the mixed lipid+ethanol solution was then injected into an aqueous phase (aqueous phase I) at various flow rates. The tubing ID of the ethanol phase was 0.508 mm (1.588 mm OD). The aqueous phase I tubing ID was fixed at 4.572 mm. Flow rates of the lipid+ethanol phase were from 5-40 mL/min and aqueous phase I were from 70-300 mL/min.

After the liposomes were formed, the liposomes passed through a degassing unit (Liqui-Cel®) followed by a second three-way T-port. This three-way T-port has one inlet for the liposomes, a second inlet for aqueous buffer and one outlet. A second gear pump (Micropump®) was used to control the flow of the aqueous phase into this port (aqueous phase II). The aqueous phase II flow rate was adjusted such that mixed aqueous phase would have 5% vol. ethanol. Aqueous phase II flow rates ranged from 690-460 mL/min.

Data Acquisition System and Computer Software

The entire process was controlled by a custom-made program written using National Instruments (NI) LabVIEW® software. A data acquisition system (NI PXIe-1078) was combined with multiple NI modules to accommodate various input/output signals (e.g. analog and digital inputs/outputs, counters, circuit switches, etc.). The entire system was automated and only required the user to define the final lipid concentration and molar ratios of lipid. Process variables such as flow rates, pressure, and temperature were monitored and, for some variables, automatically adjusted using custom computer algorithms. For example, proportional-integral-derivative controls were implemented in the computer program to precisely control the flow rates of both the ethanol and aqueous phases.

Communication to and from the Malvern Zetasizer was accomplished using the Malvern Link II software. Malvern Link II software was setup as an OPC server and NI LabVIEW was setup as an OPC client. The z-average particle size and PDI were recorded in the custom computer program. The custom computer program was able to send measurement instructions to the Malvern Zetasizer.

Particle Size Measurements

All particle size measurements were performed using a Malvern Zetasizer Nano S. Prior to measurements, the liposomes were diluted in-line to 5% vol. ethanol and the viscosity and refractive index were pre-set in the Malvern Zetasizer software. Particle size measurements included the z-average particle size and polydispersity index (PDI). For the off-line measurements, disposable plastic cuvettes were used. The samples were equilibrated at 25° C. prior to each measurement. Each off-line measurement duration was set for 10 runs at 10 seconds each with n=3.

For at-line measurements, a flow cell equilibrated at 25° C. was used. The measurement duration was set to 1 run for 6 seconds. The Load/Stop Mode, based on loading the flow cell followed by stopping the flow prior to the measurement, was used in all cases (see Chapter 5). A Micropump® pump was used to control the flow through the flow cell (20-25 mL/min). The pump operated at the specified flow rate prior to the particle size measurement. Before any measurement took place, the custom computer algorithm stopped the pump to prevent fluid flow during the measurement.

NIR (Turbidity) Measurements

An Optek® TF16-N Scattered light dual channel turbidity sensor was used for the measurements. This device has two simultaneous channels, the first measures light absorption, i.e. this principle is based on detecting the light at 0° from the light source by a single hermetically sealed photodiode. This measurement is in concentration units (CU). The second measurement principle is based on light scattering and the scattered light is detected at 11° by eight hermetically sealed silicon photodiodes. This measurement is reported in parts per million (PPM). The measurement wavelengths are a band ranging from 730 nm to 970 nm. The optical path length of the sensor is fixed at 40 mm and is in a flow cell configuration, i.e. has an inlet and outlet for in-line application. The linearity of the sensor is <±1% of the full scale for each measurement and has a repeatability of <±0.5%.

Tangential Flow Filtration System

An EMD Millipore Pellicon Mini Holder with Pellicon 2 Mini Ultrafiltration Biomax-100 modules was used as the tangential flow filtration (TFF) device. This device was connected to a peristaltic pump (Blue-White Industries, LTD) to control the flow rate. A pressure transducer and solenoid valve were connected to the output of the TFF device. The pump, pressure transducer and the solenoid valve were connected to the custom LabVIEW computer program (FIG. 8).

Lipid Concentration Analysis Via the Stewart Assay

The Stewart assay is a UV-spectrometric technique that determines the amount of phospholipid present. Briefly, ammonium ferrothiocyanate (AF) was prepared by dissolving 13.52 g of ferric chloride hexahydrate and 15.2 g of ammonium thiocyanate in 0.5 liters of deionized water. A calibration curve was generated by taking 10-70 mg of phospholipid stock solution (originally dissolved in ethanol) added to approximately 3 mg of chloroform. 2 mL of the AF solution was added to this mixture, which was then vortexed for 30 seconds followed by centrifugation at 1,500 rpm for 2 minutes. The AF was removed and the chloroform containing lipid was analyzed using a Cary 50 UV-spectrophotometer at 470 nm. The calibration curve consisted of 9 values with a quantitation limit (QL) of 0.023 µg/mL and an R-squared of 0.997.

Lipid Concentration Analysis Via High Pressure Liquid Chromatograph—Mass Spectrometry The lipid concentration was determined using a high pressure liquid chromatography (HPLC) with a mass spectrometer (MS). A Waters Xbridge C8, 3.5 um, 4.6×75 mm column heated at 30° C. was used for lipid separation. The mobile phase was 2 mM ammonium formate in MS-grade methanol. The flow rate was set at 0.3 mL/min and 3 µL of sample was injected for each measurement. An ESI probe was used and the operating conditions were optimized in the TSQ software (FIG. 44).

The sample was analyzed for the main phospholipid depending on the lipid formulation, i.e. for DPPC. The raw chromatographic data was transformed using a power function value (PFV) and the area under the curve was calculated. The tailing factor was less than 1.20 for each peak. The calibration curves had a QL of approximately 1.22 ug/mL and the R-squared value was >0.996. The PFV used for DPPC was 1.23.

Lipid Concentration Prediction Models

Figure 38:
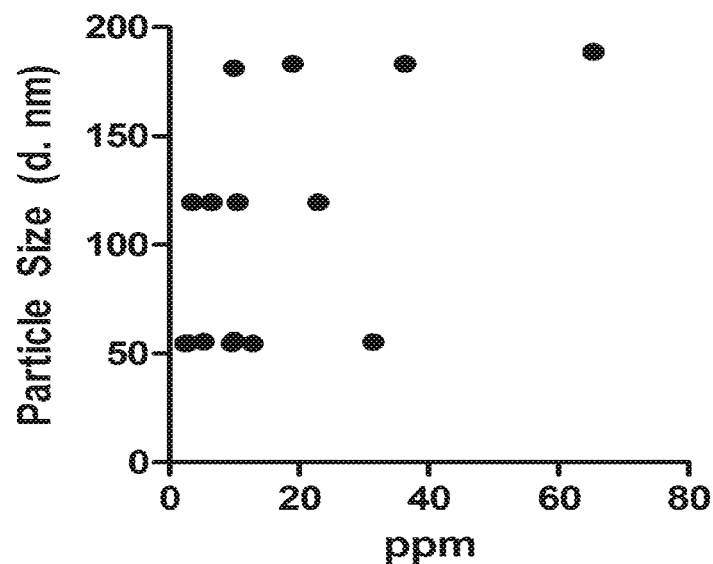
FIG. 38 is a graphical representation of an experimental design of the lipid concentration prediction model based on scattered light from an NIR turbidity sensor, according to an example embodiment.
Figure 39:
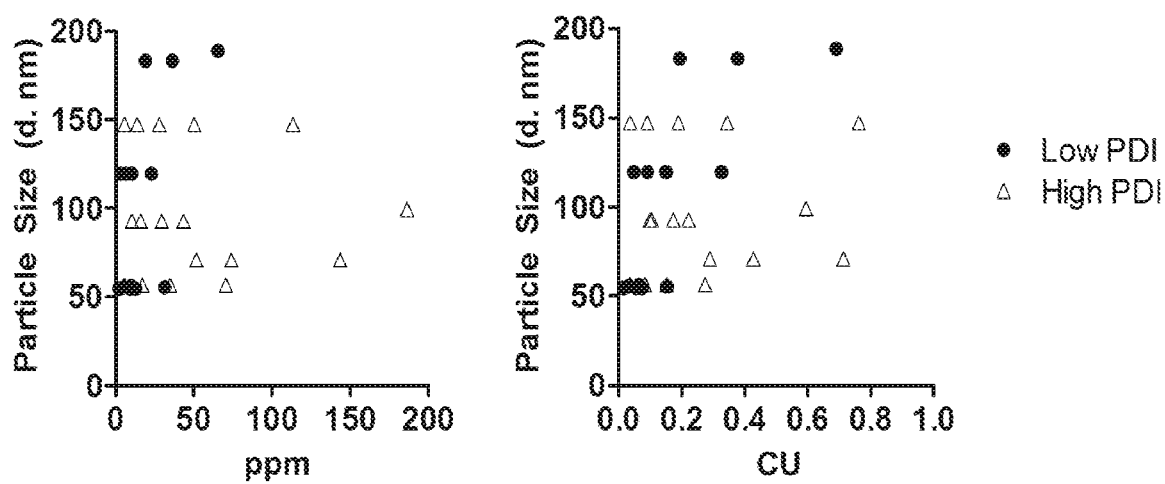
FIG. 39 is a graphical representation of an experimental design for the lipid concentration with factors including particle size (d.nm), polydispersity index (PDI), ppm and CU, according to an example embodiment.

JMP by SAS was used to generate prediction models and equations. Two models (defined as Model 1 and Model 2) were generated that had the response as the total lipid concentration ([Lipid]) in units of mM. The possible factors for the model were the NIR measurements (both CU and ppm) the z-average particle size (d.nm) and the polydispersity index (PDI). Model 1 only included particle size and ppm as factors. Only monodispersed liposome (i.e. having a PDI≤0.1) were used to generate this model. The experimental design for Model 1 is outlined in FIG. 38. Since the ppm signal was highly dependent on the particle size, a typical experimental design (e.g. full factorial) was difficult to achieve. In addition, the maximum concentration reported for this model was approximately 7 mM total lipid. Higher total lipid concentrations would be required to achieve a higher ppm signal for the smaller particle sizes (e.g. 50 nm vs. 150 nm). Model 2 is an extension of Model 1 and included particle size, PDI, ppm and CU as factors. The experimental design of Model 2 is outlined in FIG. 39.

Results:

Prediction Models

The liposomal particle size diameter ranged from 55 nm to 188 nm. For Model 1, the PDI was less than 0.10 for all sizes and concentrations tested. The total lipid concentration ranged from 0.38 mM up to 7.96 mM. The significant terms (P<0.05) were particle size, particle size*ppm and ppm (FIG. 45). Both the particle size and particle size*ppm negatively impacted the lipid concentration, whereas an increase in ppm related to an increase in lipid concentration. The NIR CU measurement did not correlate with the model and was omitted. The R-squared for the actual vs. prediction lipid concentration was 0.931, indicating a linear relationship. The model had 15 observations (with 3 degrees of freedom for the model), a RMSE of 0.587 and an analysis of variance <0.001.

Figure 40:
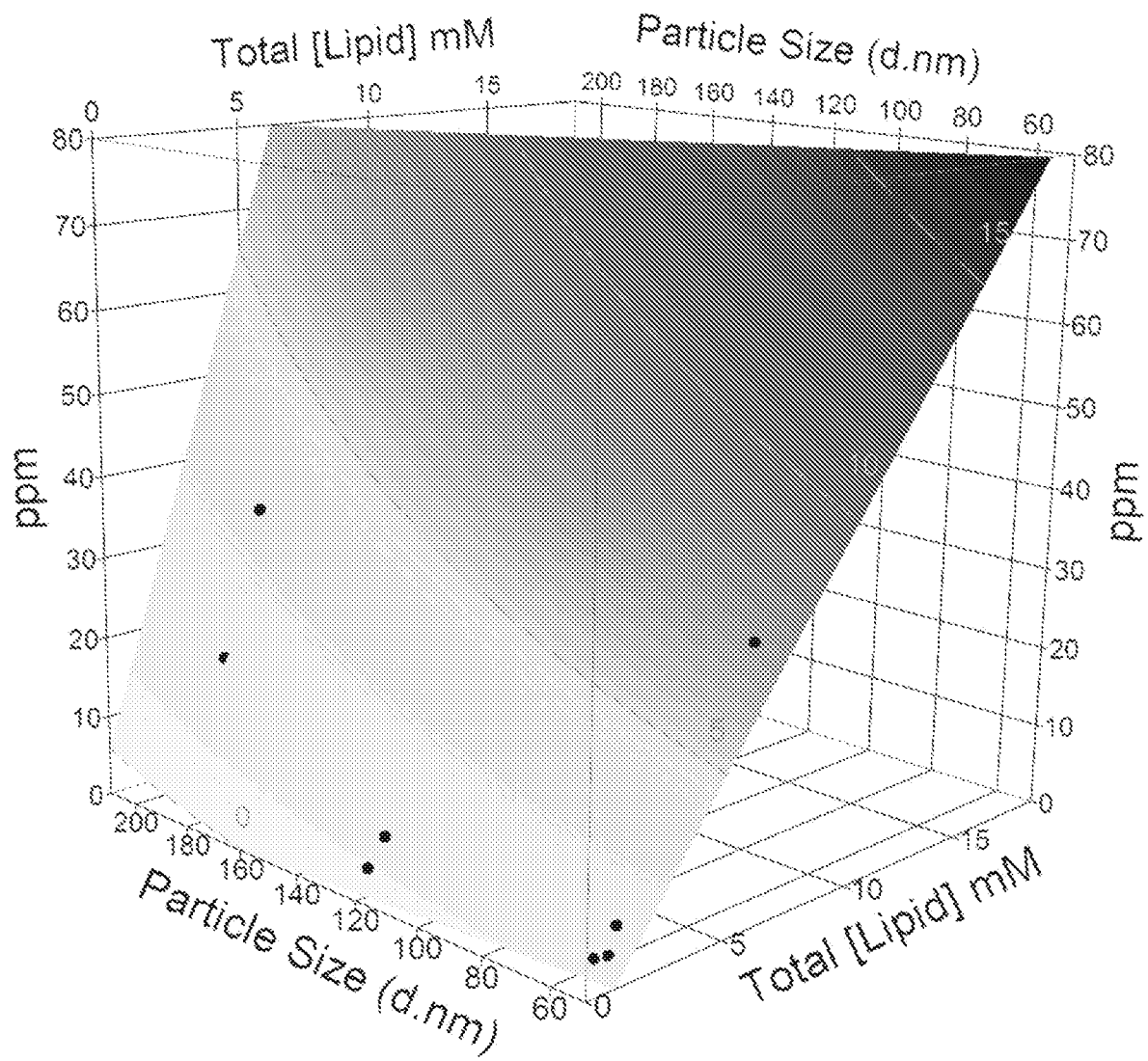
FIG. 40 is a graphical representation of a surface profile plot for the lipid concentration [Lipid] prediction model.

The surface profile for Model 1 is demonstrated in FIG. 40. The profile is of ppm vs. particle size vs. total lipid concentration. As the particle size increases, the ppm vs. [Lipid] slope increases and higher ppm values are reached for lower lipid concentrations. The smaller sized liposomes only reached approximately 30 ppm for the same maximum [Lipid], whereas the large liposomes reached up to 70 ppm. The empirical prediction equation for Model 1 is:

$$[\text{Lipid}] = 9.66 - 49.1 * \left(\frac{\text{Particle Size} - 263}{238}\right) + 10.7 * \left(\frac{ppm - 250}{250}\right) + \\ (-46.9) * \left(\frac{\text{Particle Size} - 263}{238}\right) * \left(\frac{ppm - 250}{250}\right) \quad (1)$$

This equation was implemented into the custom computer program to predict the lipid concentration based on both particle size and turbidity measurements.

For Model 2, the same particle size diameter range was used as outlined in Model 1 above. The total lipid concentration ranged from 0.38 up to 20 mM. Significant terms for Model 2 are listed in FIG. 47, with particle size*ppm and ppm as the most significant. Both the CU and PDI also had statistical significant terms in the model. The R-squared for the actual vs. prediction lipid concentration was 0.987, indicating a linear relationship. The model had 35 observations (with 11 degrees of freedom for the model), a RMSE of 0.527 and an analysis of variance <0.001. The empirical prediction equation for Model 2 is:

$$[Lipid] = -20.1 - 58.7 * \left(\frac{\text{Particle Size} - 263}{238}\right) - \\ 66.0 * \left(\frac{ppm - 250}{250}\right) + 53.5 * \left(\frac{CU - 2}{2}\right) + 76.0 * PDI + \\ 29.9 * \left(\frac{\text{Particle Size} - 263}{238}\right) * \left(\frac{\text{Particle Size} - 263}{238}\right) - \\ 97.0 * \left(\frac{\text{Particle Size} - 263}{238}\right) * \left(\frac{ppm - 250}{250}\right) + \\ 11.6 * \left(\frac{ppm - 250}{250}\right) * \left(\frac{CU - 2}{2}\right) + \\ 86.0 \left(\frac{\text{Particle Size} - 263}{238}\right) * (PDI - 0.102) + \\ 22.0 * \left(\frac{CU - 2}{2}\right) * (PDI - 0.102) + \\ 1290 * \left(\frac{CU - 2}{2}\right) * (PDI - 0.102) * (PDI - 0.102) + \\ 1070 * (PDI - 0.102) * (PDI - 0.102) \quad (2)$$

A validation for both Model 1 and Model 2 was included. The liposomes had a mean particle size of 167±4.40 nm and a PDI of 0.05±0.02 (FIG. 47). The total lipid concentration range measured was from 1.80-7.07 mM. As the PDI was less than 0.1, both models could be used to predict the mean particle size, with the mean error less than equal to 7.5%. When comparing the percent error of the measured [Lipid] to the predicted [Lipid], a two-tailed, paired t-test resulted in a p-value of 0.23, indicating that the differences between the sets of data are insignificant.

Polydispersity on the NIR Signal

Figure 41:
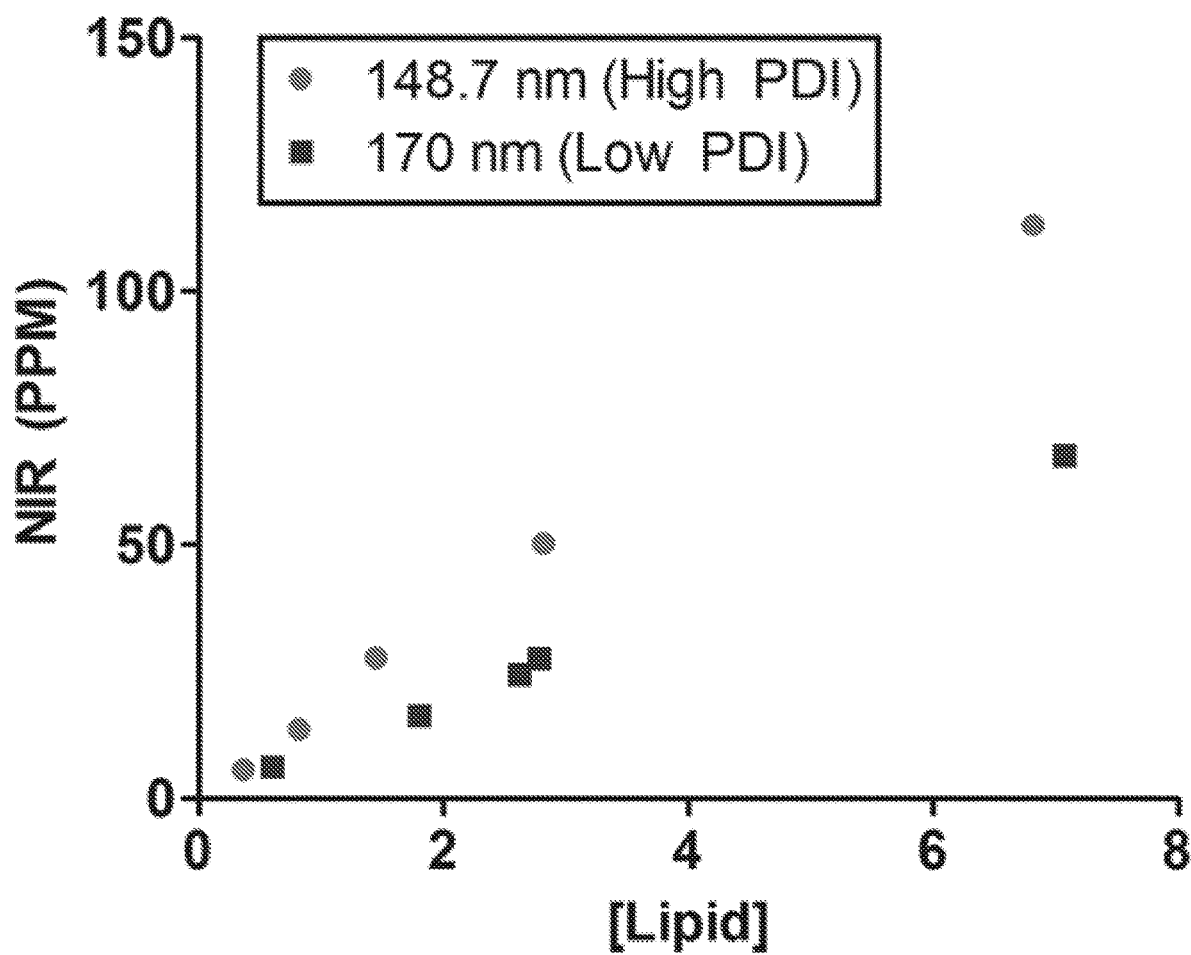
FIG. 41 is a graphical representation of an example of how the NIR signal output in PPM is affected by the polydispersity of a liposomal formation, according to an example embodiment.

A comparison was made between two sets of data for liposomes of a similar particle size but with differences in the PDI. The lower PDI (≤0.1) indicates a single population of particles, whereas a higher PDI indicates multiple populations of particles present. From FIG. 41, it is evident that the PDI is a factor that may preferably be controlled. The liposomes with a mean particle size of 149 nm and a PDI of 0.18 t 0.02 produced a PPM signal greater than those with a mean diameter of 170 nm and a PDI of 0.06±0.02.

Discussion

Lipid Concentration Model

The relationship between scattered light and particle size are explained by Mie scattering theory. The Mie theory explains light scattering by an induced dipole moment from an incident electromagnetic wave. The induced dipole acts as a source of electromagnetic radiation and emits or scatters light at the same frequency as the source, i.e. elastic scattering. This theory provides an angular dependence of the scattered light based on the incident wavelength and the particle size. Relationships between liposomal particle size and light scattering and turbidity have been previously analyzed for liposomes. The theory is based on an approximation of the Mie scattering theory, called the Rayleigh-Gans-Debye approximation. From this approximation, lipid concentration may be estimated at a fixed incident wavelength if additional properties such as the refractive index of the aqueous medium and the refractive index of the lipid bilayer are known. However, this approximation may not be suitable for the current case since the incident radiation is a band of wavelengths covering 730-970 nm. In addition, the liposomes in this study were both monodispersed and polydispersed, which would further cause difficulties in using theoretical approximations to predict the total lipid concentration. For this reason, an empirical model was developed to relate liposomal particle size, PDI and the NIR signals (ppm and CU) to the total lipid concentration.

As expected, smaller particles scatter less light compared to larger particles. For this reason, the ppm/CU increases as the particle size increases. Two predictive models were generated, the first for only monodispersed liposomes (i.e. liposomes with a PDI≤0.10) and the second included liposomal formulations with a higher PDI (PDI>0.10). For the monodispersed liposomal model, detection at 0° (measured in CU) did not appear to have any correlation with particle size and concentration at the concentrations measured. The CU did increase linearly with an increase in lipid concentration, but did not form a correlation when comparing different particle size liposomes. In contrast, the scattered light at 11° (i.e. the ppm) demonstrated a correlation with both liposomal particle size and total lipid concentration. For this reason, only the scattered light was used in the prediction model for monodispersed liposomes. Moreover, since the ppm signal is referenced to the medium, the NIR sensor was able to measure low lipid concentrations and the detection was not affected by additions to the aqueous phase (e.g. ethanol).

For the second model (Model 2), the CU signal and the particle size PDI were added to Model 1. This addition to the model enabled the total lipid concentration to be predicted for both monodispersed and poly dispersed liposomal formulations. The addition of a polydispersity term into the model enhances the overall predictability of the total lipid concentration for both monodispersed and polydispersed systems. The validation sample set demonstrated the robustness of both models. By comparing the mean error for each model, the error was insignificant, indicating that each model could be used for low PDI formulations. However, Model 1 could not be used for higher PDI formulations. These results demonstrated that an empirical model with only 3 degrees of freedom could predict the particle size of monodispersed liposomes; whereas an empirical model with 11 degrees of freedom was required for polydispersed samples. Therefore, when liposomes are formed with a low polydispersity, a relatively simple and low degree of freedom model may be used to predict the total lipid concentration of the liposomes.

Polydispersity on NIR Detection

To emphasize how the polydispersity of the sample negatively impacted the prediction model, two data sets were plotted. The result that a high PDI sample increased the scattered light was expected as multiple populations of liposomes in the same sample will cause large variations in the scattered light. From the Mie theory, large particles will scatter light in the forward direction more than smaller particles. In addition, larger diameter particles scatter more light. The combination of a change in the angular scattering and scattering intensity prevented this model from predicting the lipid concentration. Therefore, a limitation to Model 1 is that it is only applicable to monodispersed liposomes. For polydispersed liposomes, Model 2 should be used to predict the total lipid concentration.

Conclusions:

A tangential flow filtration system was implemented with a continuous liposome formation process to continuously concentrate liposomes in-line. Empirical models were developed for both monodispersed and polydispersed liposomes that had the total lipid concentration as the model response. These models can predict the lipid concentration from 0.38 up to 20 mM total lipid for particle size diameters from approximately 50 nm up to 200 nm. One limitation for Model 1 is that it is only applicable to monodispersed liposomes. Model 2 has predictive power for both monodispersed and polydispersed, but requires a model with 11 degrees of freedom. The implementation of the concentrating system and predictive models into a continuous process for liposomes enhances process control. Moreover, this system results in effectively controlling one quality attribute (i.e. lipid concentration) of liposomal drug products.

Tables:

FIG. 44 illustrates a table showing TSQ HPLC-MS ESI operating conditions used in the analysis of lipid concentration quantitation.

FIG. 45 illustrates a table showing sorted parameter estimates and model terms for Model 1.

FIG. 46 illustrates a table showing sorted parameter estimates and model terms for Model 2.

FIG. 47 illustrates a table showing validation data points for both lipid concentration ([Lipid]) models. Model 1 is based on particle size and ppm, whereas Model 2 includes particle size, polydispersity index (PDI), ppm and CU.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

Since many modifications, variations, and changes in detail can be made to the described example, it is intended that all matters in the preceding description and shown in the accompanying Figures be interpreted as illustrative and not in a limiting sense. Further, it is intended to be understood that the following clauses (and any combination of the clauses) further describe aspects of the present description.

We claim:

1. A system comprising:
one or more containers;
one or more vessels;
an injection port including:
 a first inlet including a first conduit in fluid communication with the one or more containers,
 a second inlet including a second conduit in fluid communication with the one or more vessels, and
 an outlet, wherein the first conduit is positioned concentrically within the second conduit, wherein the first conduit extends through the outlet, wherein the second conduit extends through the outlet, and wherein the first conduit terminates within the second conduit;
a three-way port including a first port in fluid communication with the outlet of the injection port, a second port in fluid communication with the one or more vessels, and a third port comprising an outlet port; and
one or more degassing units positioned between the injection port and the three-way port.

2. The system of claim 1, further comprising:
a first gear pump positioned between a first vessel of the one or more vessels and the injection port;
a second gear pump positioned between a second vessel of the one or more vessels and the three-way port; and
a third gear pump positioned between the one or more containers and the injection port.

3. The system of claim 2, further comprising:
a first flow meter positioned between the first gear pump and the injection port;
a second flow meter positioned between the second gear pump and the three-way port; and
a third flow meter positioned between the third gear pump and the injection port.

4. The system of claim 1, wherein the injection port, the first conduit and the second conduit each comprise stainless steel.

5. The system of claim 1, wherein in the injection port, the first conduit extends between about 0.5 inches to about 24 inches from the outlet, and wherein the second conduit extends between about 0.5 inches to about 24 inches from the outlet.

6. The system of claim 1, further comprising:
a mixer positioned between the one or more containers and the injection port.

7. The system of claim 6, wherein the mixer is a static mixer combines solutions from each of the one or more containers.

8. The system of claim 1, wherein the second conduit of the injection port is in fluid communication with a first vessel of the one or more vessels, and wherein the second port of the three-way port is in fluid communication with a second vessel of the one or more vessels.

9. The system of claim 1, wherein the second conduit of the injection port is in fluid communication with a first vessel of the one or more vessels, and wherein the second port of the three-way port is also in fluid communication with the first vessel of the one or more vessels.

10. The system of claim 1, wherein the system comprises of two or more injection ports, wherein an outlet of each of the two or more injection ports is in fluid communication with the first port of the three-way port.

11. The system of claim 1, further comprising:
a dynamic light scattering particle size analyzer in fluid communication with the third port of the three-way port, wherein the particle size analyzer is configured to determine a size of liposomes; and
a controller configured to:
 determine a difference between a desired size of the liposomes and the determined size of the liposomes; and
 in response to the determined difference, adjust one or more parameters of the system.

12. The system of claim 11, wherein the one or more parameters of the system comprises one or more of (i) a flow rate at which an aqueous solution is supplied from the one or more vessels to the second inlet of the injection port, (ii) a flow rate of an organic lipid solution supplied from the one or more containers to the first inlet of the injection port, (iii) a temperature of the aqueous solution supplied from the one or more vessels to the second inlet of the injection port, (iv) a temperature of the organic lipid solution supplied from the one or more containers to the first inlet of the injection port, (v) a lipid concentration of the organic lipid solution supplied from the one or more containers to the first inlet of the injection port, and (vi) a viscosity of the aqueous solution supplied from the one or more vessels to the second inlet of the injection port.

13. A method for the continuous production of liposomes, the method comprising:
   providing the system of claim 1;
   mixing a solution of lipid and organic solvent from the one or more containers to create an organic solvent-lipid solution;
   providing the organic solvent-lipid solution to the first inlet of the injection port at a first flow rate, wherein the first inlet is in fluid communication with the first conduit;
   providing an aqueous solution to the second inlet of the injection port at a second flow rate, wherein the second inlet is in fluid communication with the second conduit, wherein the first conduit is positioned concentrically within the second conduit at the outlet of the injection port, and wherein the first conduit extends through the outlet of the injection port; and
   mixing the organic lipid solution and the aqueous solution to create a plurality of liposomes.

14. The method of claim 13, the method further comprising:
   determining a size of one or more of the plurality of liposomes.

15. The method of claim 14, wherein the determining is done while the plurality of liposomes move at a constant flow rate.

16. The method of claim 14, wherein the determining comprises:
   momentarily stopping a pump to prevent fluid flow of the one or more of the plurality of liposomes;
   determining the size of one or more of the plurality of liposomes while the plurality of liposomes are at rest; and
   starting the pump to resume fluid flow.

17. The method of claim 13, further comprising:
   determining a difference between a desired size of the one or more liposomes and the determined size of the one or more liposomes; and
   in response to the determined difference, adjusting at least one of the following parameters: aqueous phase flow rate, organic phase flow rate, lipid concentration, aqueous phase temperature, type of lipid and aqueous phase additives, and organic phase temperature.

18. The method of claim 13, further comprising:
   passing the plurality of liposomes to a tangential flow filtration unit;
   determining a total lipid concentration of the plurality of liposomes;
   determining a difference between a desired total lipid concentration of the liposomes and the determined total lipid concentration of the liposomes; and
   in response to the determined difference, adjusting a permeate flow rate of the tangential flow filtration unit and/or adjusting a pressure of the tangential flow filtration unit.

19. The method of claim 13, further comprising:
   passing the plurality of liposomes to a degassing unit the one or more degassing units;
   passing the plurality of liposomes from the degassing unit to the first port of the three-way port;
   providing an aqueous buffer to the second port of the three-way port at a third flow rate; and
   mixing the plurality of liposomes and the aqueous buffer.

* * * * *